(12) United States Patent
Sawyers et al.

(10) Patent No.: US 11,446,400 B2
(45) Date of Patent: Sep. 20, 2022

(54) FREE PSA ANTIBODIES AS DIAGNOSTICS, PROGNOSTICS AND THERAPEUTICS FOR PROSTATE CANCER

(71) Applicant: Memorial Sloan Kettering Cancer Center, New York, NY (US)

(72) Inventors: Charles Sawyers, New York, NY (US); David Ulmert, Brooklyn, NY (US); Jason Lewis, New York, NY (US); Michael Evans, New York, NY (US); Hans Lija, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 16/430,041

(22) Filed: Jun. 3, 2019

(65) Prior Publication Data

US 2019/0381200 A1 Dec. 19, 2019

Related U.S. Application Data

(63) Continuation of application No. 14/353,989, filed as application No. PCT/US2012/061982 on Oct. 25, 2012, now abandoned.

(60) Provisional application No. 61/551,195, filed on Oct. 25, 2011.

(51) Int. Cl.
*A61K 51/10* (2006.01)
*G01N 33/574* (2006.01)
*A61B 5/00* (2006.01)

(52) U.S. Cl.
CPC ........ *A61K 51/1018* (2013.01); *A61B 5/4381* (2013.01); *A61B 5/4833* (2013.01); *A61K 51/1072* (2013.01); *G01N 33/57434* (2013.01); *G01N 2800/52* (2013.01)

(58) Field of Classification Search
CPC ........ A61K 51/00; A61K 51/04; A61K 51/06; A61K 51/065; A61K 51/08; A61K 51/10; A61K 51/1018; A61K 51/1072; A61K 2120/00; A61K 2123/00; A61K 5/145; A61K 49/00; A61K 49/0004; A61K 49/001; A61K 49/22; A61B 5/4381; A61B 5/4833; G01N 33/57434; G01N 2800/52; G01N 2800/00; A61P 43/00; A61P 35/00; A61P 35/04; A61P 13/08
USPC ...... 424/1.11, 1.49, 1.65, 1.69, 9.1, 9.2, 9.3, 424/9.4, 9.5, 9.6; 514/1, 1.1, 19.2, 19.3, 514/19.5, 20.9, 21.1; 530/300, 324, 325, 530/326, 327, 328, 330, 350
See application file for complete search history.

(56) References Cited

U.S. PATENT DOCUMENTS

| | | |
|---|---|---|
| 5,171,741 A | 12/1992 | Dougherty |
| 5,171,749 A | 12/1992 | Levy et al. |
| 5,173,504 A | 12/1992 | Dougherty |
| 5,308,608 A | 5/1994 | Dolphin et al. |
| 5,405,957 A | 4/1995 | Tang et al. |
| 5,512,675 A | 4/1996 | Tang et al. |
| 5,545,806 A | 8/1996 | Lonberg et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,726,304 A | 3/1998 | Tang et al. |
| 5,739,116 A | 4/1998 | Hamann et al. |
| 5,773,001 A | 6/1998 | Hamann et al. |
| 5,831,088 A | 11/1998 | Dolphin et al. |
| 5,877,296 A | 3/1999 | Hamann et al. |
| 5,880,145 A | 3/1999 | Sternberg et al. |
| 5,929,105 A | 7/1999 | Sternberg et al. |
| 6,423,503 B1 * | 7/2002 | Mikolajczyk .... G01N 33/57434 424/9.1 |
| 6,482,599 B1 * | 11/2002 | Mikolajczyk ........ C12N 9/6445 435/4 |
| 2002/0001588 A1 | 1/2002 | Sinha |
| 2004/0101914 A1 * | 5/2004 | Pettersson ........ G01N 33/57434 435/7.23 |

(Continued)

FOREIGN PATENT DOCUMENTS

| | | |
|---|---|---|
| CN | 101137672 A | 3/2008 |
| EP | 1858929 B1 | 4/2013 |

(Continued)

OTHER PUBLICATIONS

Nolting et al, Am. J. Nucl. Med. Mol. Imaging, vol. 2, No. 3, pp. 273-306. (Year: 2012).*
Clegg et al, Cancer Res., vol. 72, No. 6, pp. 1494-1503 (Year: 2012).*
Aboul-Fadl, T., Antisense oligonucleotides: the state of the art, Curr. Med. Chem., 12: 2193-2214 (2005).

(Continued)

*Primary Examiner* — D. L. Jones
(74) *Attorney, Agent, or Firm* — Choate, Hall & Stewart LLP; Brenda Herschbach Jarrell; Michael L. Vetter

(57) ABSTRACT

The present invention provides methods of monitoring and measuring tumor-associated free PSA ("fPSA") with antibody polypeptides as an indication of androgen receptor signaling. In a particular embodiment, the methods may be used to assess the efficacy of anti-androgen and/or general anti-cancer treatments. The present invention also provides various methods and compositions relating to antibodies that are specific for tumor-associated or intratumoral fPSA. For example, the present invention provides compositions, including pharmaceutical compositions, comprising anti-fPSA antibodies, or fragments or characteristic portions thereof. The present invention further provides various therapeutic and/or diagnostic methods of using anti-fPSA antibodies and/or compositions.

8 Claims, 17 Drawing Sheets
Specification includes a Sequence Listing.

(56) References Cited

U.S. PATENT DOCUMENTS

| | | | |
|---|---|---|---|
| 2006/0182682 A1* | 8/2006 | Ulmert | C07K 16/3069 424/1.49 |
| 2006/0199230 A1* | 9/2006 | Mikolajczyk | G01N 33/6893 435/7.23 |
| 2006/0211059 A1 | 9/2006 | Taneja | |
| 2010/0151501 A1 | 6/2010 | Mikolajczyk et al. | |
| 2011/0236903 A1 | 9/2011 | McClelland et al. | |
| 2014/0308204 A1 | 10/2014 | Sawyers et al. | |

FOREIGN PATENT DOCUMENTS

| | | |
|---|---|---|
| JP | 6181059 B2 | 8/2017 |
| WO | WO-92/01936 A1 | 2/1992 |
| WO | WO-96/39185 A1 | 12/1996 |
| WO | WO-2017/087826 A1 | 5/2017 |

OTHER PUBLICATIONS

Alpaugh et al., Superantigen-targeted therapy: phase I escalating repeat dose trial of the fusion protein PNU-214565 in patients with advanced gastrointestinal malignancies, Clin. Cancer Res., 4: 1903-1914 (1998).
Amorino et al., Enhancement of radiation effects by combined docetaxel and carboplatin treatment in vitro, Radiat. Oncol. Investig., 7(6): 343-352 (1999).
Anderson, C.J. et al.. Preparation, biodistribution and dosimetry of copper-64-labeled anti-colorectal carcinoma monoclonal antibody fragments 1A3-F(ab')2, J. Nucl. Med., 36 (5): 850-858 (1995).
Author Not Known, Glutamate carboxypeptidase II, Wikipedia, 6 pages, retrieved on Dec. 2, 2015 <https://en.wikipedia.org/wiki/Glutamate_carboxypeptidase_II>.
Author Not Known, Prostate-specific antigen, Wikipedia, 8 pages, last accessed on Dec. 2, 2015 <https://en.wikipedia.org/wiki/Prostate-specific_antigen>.
Author Not Known, Symbol Report: FOLH1, HUGO Gene Nomenclature Committee, 1 page, last accessed on Jul. 20, 2015 <http://ww.genenames.org/cgi-bin/gene_symbol_report?q=data/hgnc_>.
Bagshawe et al., Developments with targeted enzymes in cancer therapy, Current Opinions in Immunology, 11(5): 579-583 (1999).
Barbas et al., Molecular profile of an antibody response to HIV-1 as probed by combinatorial libraries, J. Mol. Biol., 230(3): 812-823 (1993).
Bi, F. et al., Small interfering RNA: a new tool for gene therapy, Curr. Gene. Ther., 3: 411-417 (2003).
Biroccio et al., The future of antisense therapy: combination with anticancer treatments, Oncogene, 22(42): 6579-6588 (2003).
Bjartell, A. et al., Time-resolved fluorescence in immunocytochemical detection of prostate-specific antigen in prostatic tissue sections, The Histochemical Journal, 31:45-52 (1999).
Brown et al., Tumor-specific genetically engineered murine/human chimeric monoclonal antibody, Cancer Res., 47(13): 3577-3583 (1987).
Brummelkamp, T.R. et al., A system for stable expression of short interfering RNAs in mammalian cells, Science, 296(5567): 550-553 (2002).
Brummelkamp, T.R. et al., Stable suppression of tumorigenicity by virus-mediated RNA interference, Cancer Cell, 2(3): 243-247 (2002).
Buchholz et al., 5-Fluorouracil-radiation interactions in human colon adenocarcinoma cells, Int. J. Radiat. Oncol. Biol. Phys., 32: 1053-1058 (1995).
Cao, X. et al.. The Distribution of Prostate Biopsy Histopathology Types in Different Levels of PSA, Journal of Clinical Urology, 22(2):109-111 (2007). English Abstracts.
Chang, SS, Monoclonal antibodies and prostate-specific membrane antigen, Curr. Opin. Investig. Drugs, 5(6): 611-615 (Abstract) (2004).
Chen, C.D., et al., Molecular Determinants of Resistance to Androgen Therapy, Nat. Med., 10(1) :33-39 (2004).
Cheng et al., Individualized patient dosing in Phase I clinical trials: the role of escalation with overdose control in PNU-214936, J. Clin. Oncol., 22: 602-609 (2004).
Cho-Chung, Y.S., DNA drug design for cancer therapy, Curr. Pharm. Des., 11(22): 2811-2823 (2005).
Chopra. A., N-[N-[(S)-1,3-Dicarboxypropyl}carbamoyl]-S-[$^{11}$C]methyl-L-cysteine, Molecular Imaging and Contrast Agent Database, p. 1-4 (2007).
Choy, H. et al., Weekly Irinotecan and Concurrent Radiation Therapy for Stage III Unresectable NSCLC, Cancer Network, 6 pages (2000) <http://www.cancernetwork.com/review-article/weekly-irinotecan-and-concurrent-ratiation-therapy-stage-iii-unresectable-nsclc>.
Choy, H., Combination Chemoradiotherapy with Gemcitabine: Potential Applications, Oncology, 14(Suppl 4):20-25 (2000), published online: Cancer Network, 8 pages (2000) <http://www.cancernetwork.com/lung-cancer/combination-chemoradiotherapy-gemcitabine-potential-applications>.
Choy, H., Taxanes in Combined-Modality Therapy for Solid Tumors, Oncology, 13: 22-38 [review article, 19 pages] (1999).
Cividalli et al., Radiosensitization by oxaliplatin in a mouse adenocarcinoma: influence of treatment schedule, Radiat. Oncol. Biol. Phys., 52(4): 1092-1098 (2002).
Davies et al., Antibody-antigen complexes, Ann. Rev. Biochem., 59: 439-473 (1990).
De Kruif, et al., Selection and application of human single chain Fv antibody fragments from a semi-synthetic phage antibody display library with designed CDR3 regions, J. Mol. Biol., 248: 97-105 (1995).
Dean, N.M. et al., Antisense oligonucleotide-based therapeutics for cancer, Oncogene, 22(56): 9087-9096 (2003).
Devi, G.R., siRNA-based approaches in cancer therapy, Cancer Gene Ther., 13(9): 819-829 (2006).
Dionet et al., Comparisons of carboplatin and cisplatin as potentiators of 5-fluorouracil and radiotherapy in the mouse L1210 leukemia model, Anticancer Res., 22(2A): 721-725 (2002).
Duan, Y., Androgen Receptor Signaling Channel and Prostate Cancer, Journal of Clinical Urology, 16(1):35-37 (2001) [English Abstract].
Eder, I.E. et al., Inhibition of LNCaP prostate cancer cells by means of androgen receptor anitsense oligonucleotides, Nature, 7(7): 997-1008 (2000).
Elbashir et al., RNA interference is mediated by 21- and 22-nucleotide RNAs, Genes Dev., 15(2): 188-200 (2001).
Evans-Axelsson, S. et al., Targeting Free Prostate-Specific Antigen for In Vivo Imaging of Prostate Cancer Using a Monoclonal Antibody Specific for Unique Epitopes Accessible on Free Prostate-Specific Antigen Alone, Cancer Biotherapy and Radiopharmaceuticals, 27(4):243-251 (2012).
Frankel, S.R., Oblimersen sodium (G3139 Bcl-2 antisense oligonucleotide) therapy in Waldenstrom's macroglobulinemia: a targeted approach to enhance apoptosis, Semin. Oncol., 30(2): 300-304 (2003).
Friedrich, I. et al., RNA molecules as anti-cancer agents, Semin. Cancer Biol., 14(4): 223-230 (2004).
Frydman, B. and Basu, H. S., Prostate-specific antigen: a diagnostic marker and a tool for targeted delivery of drugs to prostate tumors, Expert Opinion on Therapeutic Patents, 12(7):1035-1047 (2005).
Fuh, G., Synthetic antibodies as therapeutics, Expert. Opin. Biol. Ther., 7(1): 73-87 (2007).
Gao, W., Peptide antagonist of the androgen receptor, Curr. Pharm. Des., 16(9): 1106-13 (2010).
Gerhard et al., Repertoire of antiviral antibodies expressed by somatic cell hybrids, Proc. Natl. Acad. Sci. USA, 75(3): 1510-1514 (1978).
Ghosh, A. and Heston, D. W., Tumor Target Prostate Specific Membrane Antigen (PSMA) and its Regulation in Prostate Cancer, Journal of Cellular Biochemistry, 91:528-539 (2004).
Giantonio et al., Superantigen-based immunotherapy: a phase I trial of PNU-214565, a monoclonal antibody-staphylococcal enterotoxin A recombinant fusion protein, in advanced pancreatic and colorectal cancer, J. Clin. Oncol., 15: 1994-2007 (1997).
Gleave, M.E. and Monia, B.P., Antisense therapy for cancer, Nat. Rev. Cancer, 5(6): 468-479 (2005).

(56) References Cited

OTHER PUBLICATIONS

Goel, S. et al., A safety study of a mixed-backbone oligonucleotide (GEM231) targeting the type I regulatory subunit alpha of protein kinase A using a continuous infusion schedule in patients with refractory solid tumors, Clin. Cancer Res., 9(11): 4069-4076 (2003).
Griffiths et al., Isolation of high affinity human antibodies directly from large synthetic repertoires, EMBO J., 13(14): 3245-3260 (1994).
Hemman M.T. et al., An epi-allelic series of p53 hypomorphs created by stable RNAi produces distinct tumor phenotypes in vivo, Nat. Genet., 33(3): 396-400 (2003).
Henry, S.P. et al., Toxicological and pharmacokinetic properties of chemically modified antisense oligonucleotide inhibitors of PKC-alpha and C-raf kinase, Anticancer Drug Des., 12(5): 409-420 (1997).
Holland, J.P. et al., 89Zr-DFO-J591 for immunoPET of prostate-specific membrane antigen expression in vivo, J. Nucl. Med., 51(8):1293-300 (2010).
Holland, J.P. et al., Measuring the pharmacokinetic effects of a novel Hsp90 inhibitor on HER2/neu expression in mice using 89Zr-DFO-trastuzumab, PLoS ONE, 5(1), e8859, 11 pages (2010).
Hoogenboom, H.R. and Winter, G., By-passing immunization. Human antibodies from synthetic repertoires of germline VH gene segments rearranged in vitro, J. Mol. Biol., 227(2): 381-388 (1992).
Huls et al., A recombinant, fully human monoclonal antibody with antitumor activity constructed from phage-displayed antibody fragments, Nat. Biotech., 17(3): 276-281 (1999).
Inanami et al., Hypoxia and etanidazole alter radiation-induced apoptosis in HL60 cells but not in MOLT-4 cells, Int. J. Radiat. Biol., 78(4): 267-274 (2002).
International Search Report for PCT/US2012/061982, 2 pages (dated Jan. 9, 2013).
Izquierdo, M., Short interfering RNAs as a tool for cancer gene therapy, Cancer Gene Ther., 12(3): 217-227 (2005).
Jonak et al., Transfection of primary mouse lymphocytes with human-tumor dna—production of continuous cell-lines producing monoclonal-antibodies, Abstract, Hybridoma, 2(1): 124 (1983).
Jones et al., Replacing the complementarity-determining regions in a human antibody with those from a mouse, Nature, 321(6069): 522-525 (1986).
Kim et al., Antibody engineering for the development of therapeutic antibodies, Mol. Cells, 20(1): 17-29 (2005).
Knappik et al., Fully synthetic human combinatorial antibody libraries (HuCAL) based on modular consensus frameworks and CDRs randomized with trinucleotides, J. Mol. Biol., 296(1): 57-86 (2000).
Kohler et al., Continuous cultures of fused cells secreting antibody of predefined specificity, Nature, 256(5517): 495-497 (1975).
Kozbor et al., Human hybridomas constructed with antigen-specific Epstein-Barr virus-transformed cell lines, Proc. Natl. Acad. Sci. USA, 79: 6651-6655 (1982).
Kurreck, J., Antisense technologies. Improvement through novel chemical modifications, Eur. J. Biochem., 270(8): 1628-1644 (2003).
Lee, Y. et al., GTI-2040, an antisense agent targeting the small subunit component (R2) of human ribonucleotide reductase, shows potent antitumor activity against a variety of tumors, Cancer Res., 63(11): 2802-2811 (2003).
Leinonen, J. et al., Epitope mapping of antibodies against prostate-specific antigen with use of peptide libraries, Clin. Chem., 48(12): 2208-2216 (2002).
Lilja, H. et al., Prostate-specific antigen in serum occurs predominantly in complex with alpha 1-antichymotrypsin, Clin. Chem., 37(9): 1618-1625 (1991).
Lobuglio et al., Mouse/human chimeric monoclonal antibody in man: kinetics and immune response, Proc. Nat. Acad. Sci. USA, 86(11): 4220-4224 (1989).
Lonberg et al., Human antibodies from transgenic mice, Int. Rev. Immunol., 13(1): 65-93 (1995).

Lou, T.F. et al., The reduction of Raf-1 protein by phosphorothioate ODNs and siRNAs targeted to the same two mRNA sequences, Oligonucleotides, 13(5): 313-324 (2003).
Lovgren, J. et al., Production of Recombinant PSA and HK2 and Analysis of Their Immunologic Cross-Reactivity, Biochemical and Biophysical Research Communications, 213(3):888-895 (1995).
Lu, B. et al., Survivin as a therapeutic target for radiation sensitization in lung cancer, Cancer Res., 64(8): 2840-2845 (2004).
Lu, P.Y. et al., In vivo application of RNA interference: from functional genomics to therapeutics, Adv. Genet., 54: 117-142 (2005).
Lu, P.Y. et al., siRNA-mediated antitumorigenesis for drug target validation and therapeutics, Curr. Opin. Mol. Ther., 5: 225-234 (2003).
Masunaga et al., The usefulness of a continuous administration of tirapazamine combined with reduced dose-rate irradiation using {gamma}-rays or reactor thermal neutrons, Br. J. Radiol., 79(948): 991-998 (2006).
McManus et al., Gene silencing in mammals by small interfering RNAs, Nature Rev. Genet., 3(10): 737-747 (2002).
Menez, R., Crystal structure of a ternary complex between human prostate-specific antigen, its substrate acyl intermediate and an activating antibody, J. Mol. Biol., 376(4): 1021-1033 (2008).
Milhavet, O. et al., RNA interference in biology and medicine, Pharmacol. Rev., 55(4): 629-648 (2003).
Monia, B.P. et al., Sequence-specific antitumor activity of a phosphorothioate oligodeoxyribonucleotide targeted to human C-raf kinase supports an antisense mechanism of action in vivo, Proc. Natl. Acad. Sci. USA, 93(26): 15481-15484 (1996).
Mornex, F. and Girard, N., Gemcitabine and radiation therapy in non-small cell lung cancer: state of the art, Annals of Oncology, 17(12): 1743-1747 (2006).
Nissim et al., Antibody fragments from a 'single pot' phage display library as immunochemical reagents, EMBO J., 13(3): 692-698 (1994).
Nurmikko, P. et al., Production and characterization of novel anti-prostate-specific antigen (PSA) monoclonal antibodies that do not detect internally cleaved Lys145-Lys146 inactive PSA, Clin. Chem., 46(10):1610-8 (2000).
Ogreid, P. et al., Tissue Prostate-Specific Antigen and Androgen Receptor Immunoreactivity in Prostate Cancer Biopsies before, during and after Neo-Adjuvant Androgen Deprivation Followed by Radiotherapy, European Urology, 36:116-122 (1999).
Palcic et al., The effect of misonidazole as a hypoxic radiosensitizer at low doses, Radiat. Res., 100:340-347 (1984).
Parracino, A. et al., Arraying prostate specific antigen PSA and Fab anti-PSA using light-assisted molecular immobilization technology, Protein Sci., 19(9):1751-9 (2010).
Partial Supplementary European Search Report for EP12844178.9, 5 pages (dated May 26, 2015).
Peltola, M.T. et al., Immunoassay for the discrimination of free prostate-specific antigen (fPSA) forms with internal cleavages at Lys145 or Lys146 from fPSA without internal cleavages at Lys145 or Lys146, Journal of Immunological Methods, 369:74-80 (2011).
Perabo et al., Preclinical evaluation of superantigen (staphylococcal enterotoxin B) in the intravesical immunotherapy of superficial bladder cancer, Int. J. Cancer, 115:591-598 (2005).
Pettersson, K. et al., Free and Complexed Prostate-Specific Antigen (PSA): In Vitro Stability, Epitope Map, and Development of Immunofluorometric Assays for Specfic and Sensitive Detection of Free PSA and PSA-$\alpha_1$-Antichymotrypsin Complex, 41(10):1480-1488 (1995).
Piironen, T., Determination and analysis of antigenic epitopes of prostate specific antigen (PSA) and human glandular kallikrein 2 (hK2) using synthetic peptides and computer modeling, Protein Sci., 7(2): 259-269 (1998).
Pirollo, K.F. et al., .Antisense therapeutics: from theory to clinical practice, Pharmacol. Ther., 99(1): 55-77 (2003).
Pousette, A. et al., Tissue PSA is the best predicting variable for the outcome of endocrine treatment of prostatic carcinoma, Scand J. Clinc. Lab. Invest, 59(229):27-32 (1999).
Putral, L.N. et al., RNA interference for the treatment of cancer, Drug News Perspect., 19(6): 317-324 (2006).

(56) References Cited

OTHER PUBLICATIONS

Rait, A. et al., HER-2-targeted antisense oligonucleotide results in sensitization of head and neck cancer cells to chemotherapeutic agents, Ann. N. Y. Acad. Sci., 1002: 78-89 (2003).
Rayburn, E. et al., RNA Silencing Technologies in Drug Delivery and Target Validation, Lett. Drug Design and Discov., 2: 1-18 (2005).
Redmond, R.W. et al., A compilation of singlet oxygen yields from biologically relevant molecules, Photochem. Photobiol., 70(4): 391-475 (1999).
Riechmann et al., Reshaping human antibodies for therapy, Nature, 332(6162): 323-327 (1988).
Rischin et al., Phase I Trial of Concurrent Tirapazamine, Cisplatin, and Radiotherapy in Patients With Advanced Head and Neck Cancer, J. Clin. Oncol., 19(2): 535-542 (2001).
Rooseboom et al., Enzyme-catalyzed activation of anticancer prodrugs, Pharmacol. Reviews, 56(1): 53-102 (2004).
Rudin, C.M. et al., Phase I Trial of ISIS 5132, an antisense oligonucleotide inhibitor of c-raf-1, administered by 24-hour weekly infusion to patients with advanced cancer, Clin. Cancer Res., 7(5): 1214-1220 (2001).
Safran et al., Paclitaxel, cisplatin, and concurrent radiation for esophageal cancer, Cancer Invest., 19(1): 1-7 (2001).
Schiavone, N. et al., Antisense oligonucleotide drug design, Curr. Pharm. Des., 10(7): 769-784 (2004).
Shaw et al., Characterization of a mouse/human chimeric monoclonal antibody (17-1 A) to a colon cancer tumor-associated antigen, J. Immunol., 138: 4534-4538 (1987).
Shulman et al., A better cell line for making hybridomas secreting specific antibodies, Nature, 276: 269-270 (1982).
Shulman et al., Phase I trial of the hypoxic cell cytotoxin tirapazamine with concurrent radiation therapy in the treatment of refractory solid tumors, Int. J. Radiat. Oncol. Biol. Phys., 44: 349-353 (1999).
Stahel, R.A. et al., Antisense oligonucleotides for cancer therapy—an overview, Lung Cancer, 41: S81-S88 (2003).
Stein, C.A. et al., Antisense strategies for oncogene inactivation, Semin. Oncol., 32(6): 563-573 (2005).
Stella et al., Prodrugs: A Chemical Approach To Targeted Drug Delivery, in "Directed Drug Delivery", Borchardt et al., (Eds), pp. 247-267 (Humana Press, 1985).
Stenman, U.H. et al., Summary report of the TD-3 workshop: characterization of 83 antibodies against prostate-specific antigen, Tumour Biol., 20: 1-12 (1999).
Stephens, A.C. et al., Antisense oligonucleotide therapy in cancer, Curr. Opin. Mol. Ther., 5(2): 118-122 (2003).
Supplementary European Search Report for EP 12844178.9, 3 pages (dated Sep. 11, 2015).
Søgaard, M. et al., Antibody-targeted superantigens in cancer immunotherapy, Immunotechnology, 2(3):151-62 (1996).
Tamm, I. and Wagner, M., Antisense therapy in clinical oncology: preclinical and clinical experiences, Mol. Biotechnol., 33(3): 221-238 (2006).
Tamulevicius et al., Misonidazole as a radiosensitizer in the radiotherapy of glioblastomas and oesophageal cancer. Pharmacokinetic and clinical studies, Br. J. Radiology, 54(640): 318-324 (1981).
Terman et al., Staphylococcal superantigens of the enterotoxin gene cluster (egc) for treatment of stage IIIb non-small cell lung cancer with pleural effusion, Clin. Chest Med., 27: 321-324 (2006).
Therasse et al., New guidelines to evaluate the response to treatment in solid tumors, J. Natl. Cancer Inst., 92(3): 205-216 (2000).
Thorek, D. L. J. et al, Internalization of secreted antigen-targeted antibodies by the neonatal Fc receptor for precision imaging of the androgen receptor axis, Sci. Transl. Med., 8(367): 367ra167 (2016).
Ulmert, D. et al., Imaging androgen receptor signaling with a radiotracer targeting free prostate-specific antigen, Cancer Discov., 2(4):320-7 (2012).
Vaughan et al., Human antibodies with sub-nanomolar affinities isolated from a large non-immunized phage display library, Nature Biotech., 14(3): 309-314 (1996).
Verel, I. et al., 89Zr-Immuno-PET: Comprehensive Procedures for the Production of 89Zr-Labeled Monoclonal Antibodies, J. Nucl. Med., 44(8): 1271-1281 (2003).
Verhoeyen et al., Reshaping human antibodies: grafting an antilysozyme activity, Science, 239(4847): 1534-1536 (1988).
Vidal L. et al., Making sense of antisense, Eur. J. Cancer, 41(18): 2812-2818 (2005).
Villoutreix, B.O., et al., A structural model for the prostate disease marker, human prostate-specific antigen, Protein Sci., 3(11): 2033-2044 (1994).
Wilman, D.E., Prodrugs in cancer chemotherapy, Biochem. Soc. Trans., 14(2):375-82 (1986).
Winter, G. and Milstein, C., Man-made antibodies, Nature, 349: 293-299 (1991).
Winter, G., Synthetic human antibodies and a strategy for protein engineering, FEBS Letters, 430(1-2): 92-94 (1998).
Written Opinion for PCT/US2012/061982, 8 pages (dated Jan. 9, 2013).
Yang, G. et al., Inhibition of breast and ovarian tumor growth through multiple signaling pathways by using retrovirus-mediated small interfering RNA against Her-2/neu gene expression, J. Biol. Chem., 279(6): 4339-4345 (2004).
Zhang, Y. et al., Reduced expression of the androgen receptor by third generation of antisense shows antitumor activity in models of prostate cancer, Mol. Cancer Therapeutics, 10(12): 2309-2319 (2011).

\* cited by examiner

FREE PSA ANTIBODIES AS DIAGNOSTICS, PROGNOSTICS AND THERAPEUTICS FOR PROSTATE CANCER

CROSS-REFERENCE TO RELATED APPLICATIONS

This application is a continuation of U.S. application Ser. No. 14/353,989, filed Apr. 24, 2014, which is a U.S. National Phase Application under 35 U.S.C. § 371 of International PCT application No. PCT/US2012/061982, filed Oct. 25, 2012, which claims the benefit of and priority to U.S. Provisional Application No. 61/551,195, filed Oct. 25, 2011. The entire contents of each of these applications are hereby incorporated herein by reference.

SEQUENCE LISTING

The instant application contains a Sequence Listing which has been submitted electronically in ASCII format and is hereby incorporated by reference in its entirety. Said ASCII copy, created on Aug. 19, 2016, is named 2003080-0676_SL.txt and is 864 bytes in size.

BACKGROUND

Prostate cancer is one of the most frequently diagnosed cancers in men, and is the most common cause of cancer-related death after lung cancer. The risk of developing prostate cancer increases dramatically with age, particularly for men over 50. With an aging population and increases in life expectancy that have marked the last thirty years, the incidence rate of prostate cancer in the United States may be approaching one in six men.

Despite considerable research into the molecular causes of prostate cancer, it remains difficult to treat. The current gold standard for treatment is surgery, typically removal of the prostate, followed by radiation or chemotherapy treatment. However, these methods are not entirely effective and compromise an individual's chances of recovering sexual function. In addition, prostate cancer cells and metastatic prostate cancer cells can compensate for treatment-reduced androgen levels by overexpressing androgen receptors or other adaptive mutations that mimic activated androgen receptor signaling. Moreover, current methods are inadequate to identify and treat metastatic prostate cancer cells that have infiltrated other tissues, for example the lymph nodes and bones. Like the prostate tumor from which they are derived, metastatic prostate cancer cells remain androgen-sensitive, and the presence of androgens drives metastatic tumor growth.

SUMMARY

Embodiments of the present invention are based on the surprising discovery that monoclonal antibodies and antibody polypeptides specific to free PSA ("fPSA") can bind to intratumoral fPSA or fPSA otherwise closely associated with prostate tumors. Tumor-associated fPSA levels can provide a highly specific and quantifiable measure of androgen receptor signaling at the tumor itself. Therefore, according to the present invention, binding of monoclonal antibodies or antibody polypeptides to tumor-associated fPSA facilitates the monitoring and/or visualization of androgen receptor signaling in situ and provides a superior measure of the efficacy of anti-cancer treatments.

Monitoring of androgen receptor signaling in situ via fPSA provides dramatically superior results compared to conventional serum PSA tests. For example, in situ fPSA levels are prostate cancer-specific and, as demonstrated herein, are directly correlated with androgen responsiveness and treatment efficacy. Therefore, embodiments of the invention disclosed herein provide non-invasive methods of measuring tumor-associated fPSA expression to more clearly reflect androgen receptor-driven changes in PSA expression. Moreover, monoclonal antibodies and antibody polypeptides are capable of detecting metastatic lesions in patients with diffuse disease and are capable of distinguishing between malignant and non-malignant disease. In addition, the binding specificity of monoclonal antibodies and antibody polypeptides for tumor-associated fPSA can serve to target therapies (e.g., chemotherapy, delivery of radioisotopes or genetic therapy) directly to prostatic tumors or metastatic sites.

Embodiments of the invention provide methods for monitoring in situ responses to prostate cancer treatment or therapy. In particular embodiments, the methods comprise administering an antibody polypeptide that binds to an epitope of free PSA ("fPSA"); determining a pretreatment level of expression or activity of fPSA in a tumor or tissue of the subject; administering a prostate cancer treatment or therapy to the subject; readministering the antibody polypeptide that binds to the epitope of fPSA; determining a post-treatment level of expression or activity of fPSA in the tumor or tissue of the subject; comparing the post-treatment level of expression or activity of fPSA in the tumor or tissue with the pretreatment level; and based on the comparing, determining whether the therapy or treatment is effective as demonstrated by a decrease of in situ fPSA activity or expression. In a particular embodiment, the epitope of fPSA is within or adjacent to the catalytic cleft. In another particular embodiment, the prostate cancer treatment or therapy is an anti-androgen therapy.

In certain embodiments, the antibody polypeptide is a monoclonal antibody. Some embodiments further comprise, prior to the administration step, combining the antibody polypeptide with a detection entity. In particular embodiments, the detection entity is selected from a group consisting of zirconium-89 ($^{89}$Zr), iodine-124 ($^{124}$I), iodine-131 ($^{131}$I), iodine-125 ($^{125}$I), bismuth-212 ($^{212}$Bi), bismuth-213 ($^{213}$Bi), astatine-211 ($^{211}$At), copper-67 ($^{67}$Cu), copper-64 ($^{64}$Cu), rhenium-186 ($^{186}$Re), rhenium-188 ($^{188}$Re), phosphorus-32 ($^{32}$P), samarium-153 ($^{153}$Sm), lutetium-177 ($^{177}$Lu), technetium-99m ($^{99m}$Tc), gallium-67 ($^{67}$Ga), indium-111 ($^{111}$In), and thallium-201 ($^{201}$Tl).

In some embodiments, the determining step comprises detection by Single Photon Emission Computed Tomography (SPECT), Position Emission Tomography (PET), or Magnetic Resonance Imaging (MRI).

In particular embodiments, the prostate cancer treatment or therapy is selected from a group comprising castration, RU58642, LG120907, LG105, RD162, MDV3100, BMS-641988, CH5137291, atraric acid, N-butylbenzenesulfonamide, cyproterone acetate, hydroxyflutamide, bicalutamide, nilutamide, peptide antagonists, TAK700, ARN-509 (abiraterone acetate), cabozantimib, ipilimumab, custirsen, BPX-101, alpharadin, denosumab and Protsvac-VF. Additional prostate cancer treatments for use in embodiments of the invention include Radium-223 chloride, cabozantinib and bicalutamide (Casodex). In certain embodiments, an efficacious treatment is indicated by a reduction in the post-treatment level of expression or activity of fPSA relative to the pretreatment level of expression or activity of fPSA.

In additional embodiments of the method, there is provided methods of monitoring in situ androgen receptor signaling in a subject. In particular embodiments, the methods comprise administering an antibody polypeptide to the subject that binds to at least one epitope within a catalytic cleft of PSA, wherein the antibody polypeptide is complexed with a detection entity; by an imaging protocol, detecting a presence of the detection entity in a prostatic tumor or metastatic cell thereof; wherein the presence of the detection entity is correlated with androgen receptor signaling. In a particular embodiment, androgen receptor signaling is imaged in vitro. In another embodiment, the androgen receptor signaling is imaged in vivo. Additional embodiments further comprise quantifying the presence of the detection entity to determine a measure of fPSA expression or activity, wherein the measure of fPSA expression is quantitatively correlated with androgen receptor signaling. In particular embodiments, the imaging protocol is selected from a group comprising Single Photon Emission Computed Tomography (SPECT), Position Emission Tomography (PET), or Magnetic Resonance Imaging (MRI).

Some embodiments of the invention provide methods of treating prostate cancer or metastatic disease thereof in a subject. In certain embodiments, the methods comprise administering to the subject a targeting entity comprising an antibody polypeptide specific to fPSA combined with or conjugated to an anti-cancer agent. As discussed throughout the application, the fPSA is substantially intratumoral or associated with prostate cancer cells. In some embodiments, an antibody or antigen-binding fragment thereof specific for fPSA is used in the manufacture of a pharmaceutical treatment or medicament for prostate cancer. In some embodiments, the antibody or antigen-binding fragment thereof is a human or mouse monoclonal antibody. In certain embodiments, the antibody is 5A10. Exemplary anti-cancer agents may be selected from the group comprising photosensitizers, nucleic acids, radiosensitizers, radioisotopes, superantigens, prodrugs, prodrug-activating enzymes, antiangiogenic agents and anti-androgen therapies. In some embodiments, the anti-cancer agents may be MDV3100, ARN-509 and doxorubicin. In some embodiments, the anti-fPSA antibody polypeptides are specific for an epitope within or adjacent to the catalytic cleft of fPSA.

Additional embodiments of the invention provide pharmaceutical compositions comprising a monoclonal antibody or fragment thereof specific to fPSA.

In another embodiment of the invention, there is provided a kit for monitoring in situ androgen receptor signaling comprising an antibody polypeptide specific for fPSA; an agent capable of detecting the level of fPSA expression or activity; a control; and instructions to provide guidance for carrying out an assay embodied by the kit and for making a determination of androgen receptor signaling based upon that assay.

DESCRIPTION OF THE DRAWING

The Figures described below, that together make up the Drawing, are for illustration purposes only, not for limitation.

FIG. 3a depicts biodistribution data of selected tissues from intact male mice bearing LNCaPAR xenografts at multiple time points show that peak intratumoral uptake of $^{89}$Zr-5A10 is observed at 24 h. Over time, activity depleted from the blood pool, represented by the blood and heart, and like many monoclonal antibodies, persistently high uptake was observed in the liver. FIG. 3b depicts representative transverse (Trans.) and coronal PET slices of intact male mice bearing LNCaPAR xenografts shows localization of $^{89}$Zr-5A10 to the tumor (T) and uptake in the murine liver (L). FIG. 3c depicts biodistribution data showing tumor associated $^{89}$Zr-5A10 in multiple s.c. prostate cancer models and several treatment conditions in intact male mice. The localization of $^{89}$Zr-5A10 to LNCaP-AR was entirely competed by co-injection with excess unlabeled 5A10 (1 mg unlabeled mAb). The non-specific radiotracer $^{89}$Zr-IgG did not localize to LNCaP-AR, and $^{89}$Zr-5A10 did not localize to PC3, an AR- and PSA-null model of prostate cancer. Intermediate localization of $^{89}$Zr-5A10 to CWR22Rv1 xenografts was observed, consistent with the lower basal expression of PSA in this model compared to LNCaP-AR. *P<0.01 compared to all conditions. "P<0.01 compared to PC3. FIG. 3d depicts surgical implantation of a s.c. testosterone pellet in castrate mice bearing LNCaP-AR tumors resulted in increased tumor-associated $^{89}$Zr-5A10, while uptake in other organs was unchanged. Biodistribution data was acquired at 24 h post injection. *P<0.01 compared to no treatment (No Tx). Error bars represent the standard deviation from mean.

FIG. 10$a$ depicts biodistribution data from castrate male mice bearing LNCaP-AR xenografts shows that MDV3100 inhibits localization of $^{89}$Zr-5A10 to tumor. Animals were treated with vehicle, or the indicated dose of MDV3100 for 7 d, at which time $^{89}$Zr-5A10 was injected, and animals were harvested for biodistribution studies 24 p.i. *P<0.01 for the 40 mg/kg and 80 mg/kg dose of MDV3100 compared to vehicle or 10 mg/kg MDV3100. FIG. 10$b$ depicts representative transverse (Trans.) and coronal PET slices of intact male mice bearing LNCaP-AR xenografts on the right flank, and imaged with $^{89}$Zr-5A10 24 h p.i. after manipulation with an s.c. testosterone pellet, or a daily oral gavage of vehicle or MDV3100 (80 mg/kg) for 7 d. Clear visual differences in tumor-associated $^{89}$Zr-5A10 can be seen between the groups. Arrows indicate the position of the tumor (T) and the murine liver (L). In FIG. 10$c$, region-of-interest analysis of the tumors from the PET study shows statistically significant changes in tumor-associated $^{89}$Zr-5A10. *P<0.01 compared to vehicle. "P<0.05 compared to vehicle. Error bars represent the standard deviation from mean.

In FIG. 14$a$, a co-registered three dimensional, volume rendered PET/CT image shows that $^{89}$Zr-5A10 localizes to an osseous LNCaP-AR graft located in the left tibia of an intact male mouse. The PET data, rendered in a blue-green color scale, shows a greater amount of activity on the animal's left (tumor-bearing) tibia compared to the right (normal) tibia. In FIG. 14$b$, a co-registered PET/MRI image shows the co-localization of positron emissions from $^{89}$Zr-5A10 with the tumor-associated contrast detected by MRI. In FIG. 14$c$ intact male mice received a fracture in the tibia, and ten days post surgery, bone remodeling was evaluated with $^{18}$F-NaF. A clear region of contrast was identified in the fractured tibia by PET. Two days after the first image, animals received a co-injection of $^{99m}$Tc-MDP and $^{89}$Zr-5A10. SPECT imaging showed that $^{99m}$Tc-MDP also localized to the region of healing bone, as expected. In contrast, PET imaging showed no detectable $^{89}$Zr-5A10 at the wound site, pointing to the high specificity of this reagent for prostate cancer compared to contemporary clinical radiotracers.

DEFINITIONS

Figure 1:
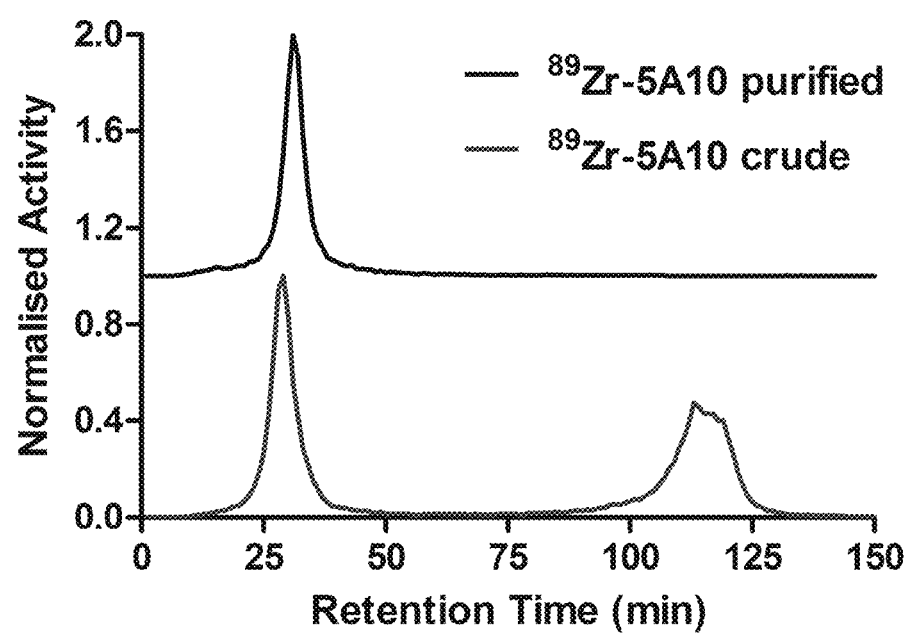
FIG. 1 depicts typical radio-ITLC chromatograms of the crude (grey) and purified (black) $^{89}$Zr-5A10. The eluant was 50 mM DTPA, pH7. The $^{89}$Zr-5A10 remains at the baseline ($R_f$=0.0) and impurities run with the solvent front ($R_f$=1.0).

Animal: As used herein, the term "animal" refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In certain embodiments, the animal is susceptible to infection by HCV. In some embodiments, an animal may be a transgenic animal, genetically engineered animal, and/or a clone.

Antagonist: As used herein, the term "antagonist" refers to an agent that i) inhibits, decreases or reduces the effects of another agent, for example that inactivates a receptor; and/or ii) inhibits, decreases, reduces, or delays one or more biological events, for example, activation of one or more receptors or stimulation of one or more biological pathways. In particular embodiments, an antagonist inhibits activation and/or activity of one or more androgen receptors. Antagonists may be or include agents of any chemical class including, for example, small molecules, polypeptides, nucleic acids, carbohydrates, lipids, metals, and/or any other entity that shows the relevant inhibitory activity. An antagonist may be direct (in which case it exerts its influence directly upon the receptor) or indirect (in which case it exerts its influence by other than binding to the receptor; e.g., altering expression or translation of the receptor; altering signal transduction pathways that are directly activated by the receptor, altering expression, translation or activity of an agonist of the receptor). In particular embodiments, androgen receptor antagonists may be selected from the group consisting of small molecule antagonists (e.g., RU58642, LG120907, LG105, RD162, MDV3100, BMS-641988, CH5137291, atraric acid, N-butylbenzenesulfonamide), steroidal compounds (e.g., cyproterone acetate), non-steroidal compounds (e.g., hydroxyflutamide, bicalutamide, nilutamide), peptide antagonists, and combinations thereof. Alternatively or additionally, anti-androgen therapies for use in embodiments of the invention include, but are not limited to TAK700, ARN-509, cabozantimib, ipilimumab, custirsen, BPX-101, alpharadin, denosumab, Protsvac-VF, and combinations thereof.

Antibody polypeptide: As used herein, the terms "antibody polypeptide" or "antibody", or "antigen-binding fragment thereof", which may be used interchangeably, refer to polypeptide(s) capable of binding to an epitope. In some embodiments, an antibody polypeptide is a full-length antibody, and in some embodiments, is less than full length but includes at least one binding site (comprising at least one, and preferably at least two sequences with structure of antibody "variable regions"). In some embodiments, the term "antibody polypeptide" encompasses any protein having a binding domain which is homologous or largely homologous to an immunoglobulin-binding domain. In particular embodiments, "antibody polypeptides" encompasses polypeptides having a binding domain that shows at least 99% identity with an immunoglobulin binding domain. In some embodiments, "antibody polypeptide" is any protein having a binding domain that shows at least 70%, 80%, 85%, 90%, or 95% identity with an immuglobulin binding domain, for example a reference immunoglobulin binding domain. An included "antibody polypeptide" may have an amino acid sequence identical to that of an antibody that is found in a natural source. Antibody polypeptides in accordance with the present invention may be prepared by any available means including, for example, isolation from a natural source or antibody library, recombinant production in or with a host system, chemical synthesis, etc., or combinations thereof. An antibody polypeptide may be monoclonal or polyclonal. An antibody polypeptide may be a member of any immunoglobulin class, including any of the human classes: IgG, IgM, IgA, IgD, and IgE. In certain embodiments, an antibody may be a member of the IgG immunoglobulin class. As used herein, the terms "antibody polypeptide" or "characteristic portion of an antibody" are used interchangeably and refer to any derivative of an antibody that possesses the ability to bind to an epitope of interest. In certain embodiments, the "antibody polypeptide" is an antibody fragment that retains at least a significant portion of the full-length antibody's specific binding ability. Examples of antibody fragments include, but are not limited to, Fab, Fab', F(ab')2, scFv, Fv, dsFv diabody, and Fd fragments. Alternatively or additionally, an antibody fragment may comprise multiple chains that are linked together, for example, by disulfide linkages. In some embodiments, an antibody polypeptide may be a human antibody. In some embodiments, the antibody polypeptides may be a humanized. Humanized antibody polypeptides include may be chimeric immunoglobulins, immunoglobulin chains or antibody polypeptides (such as Fv, Fab, Fab', F(ab')2 or other antigen-binding subsequences of antibodies) that contain minimal sequence derived from non-human immunoglobulin. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In particular embodiments, antibody polyeptides for use in accordance with the present invention bind to particular epitopes of fPSA or PSA (for example, in the catalytic cleft); in some embodiments, antibody polypeptides for use in accordance with the present invention are specific for particular epitopes of fPSA or PSA (for example, within or adjacent to the catalytic cleft). Particular exemplary antibodies are disclosed in Stenman U H et al., "*Summary report of the TD-3 workshop: characterization of* 83 *antibodies against prostate-specific antigen*", *Tumour Biol.*, 1999, 20:1-12, incorporated by reference herein. In some embodiments, an antibody polypeptides is a 5A10 or 4G10 monoclonal antibody or antigen-binding fragment thereof.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any substance that has activity in a biological system (e.g., cell culture, organism, etc.). For instance, a substance that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Characteristic portion: As used herein, the term a "characteristic portion" of a substance, in the broadest sense, is one that shares some degree of sequence or structural identity with respect to the whole substance. In certain embodiments, a characteristic portion shares at least one functional characteristic with the intact substance. For example, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance; epitope-binding specificity is one example. In some embodiments, a characteristic portion may be biologically active.

Combination therapy: The term "combination therapy", as used herein, refers to those situations in which two or more different pharmaceutical agents for the treatment of disease are administered in overlapping regimens so that the subject is simultaneously exposed to at least two agents. In some embodiments, the different agents are administered simultaneously. In some embodiments, the administration of one agent overlaps the administration of at least one other agent. In some embodiments, the different agents are administered sequentially such that the agents have simultaneous biologically activity with in a subject.

Detection entity: The term "detection entity" as used herein refers to any element, molecule, functional group, compound, fragments thereof or moiety that facilitates detection of an agent (e.g., an antibody) to which it is joined. Examples of detection entities include, but are not limited to: various ligands, radionuclides (e.g., $^{3}H$, $^{14}C$, $^{18}F$, $^{19}F$, $^{32}P$, $^{35}S$, $^{135}I$, $^{125}I$, $^{123}I$, $^{64}Cu$, $^{187}Re$, $^{111}In$, $^{90}Y$, $^{99m}Tc$, $^{177}Lu$, $^{89}Zr$ etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

Diagnostic information: As used herein, diagnostic information or information for use in diagnosis is any information that is useful in determining whether a patient has a disease or condition and/or in classifying the disease or condition into a phenotypic category or any category having significance with regard to prognosis of the disease or condition, or likely response to treatment (either treatment in general or any particular treatment) of the disease or condition. Similarly, diagnosis refers to providing any type of diagnostic information, including, but not limited to, whether a subject is likely to have a disease or condition (such as prostate cancer), state, staging or characteristic of the disease or condition as manifested in the subject, information related to the nature or classification of a tumor, information related to prognosis and/or information useful in selecting an appropriate treatment. Selection of treatment may include the choice of a particular therapeutic (e.g., chemotherapeutic) agent or other treatment modalitiy such as surgery, radiation, etc., a choice about whether to withhold or deliver therapy, a choice relating to dosing regimen (e.g., frequency or level of one or more doses of a particular therapeutic agent or combination of therapeutic agents), etc.

Dosage form: As used herein, the terms "dosage form" and "unit dosage form" refer to a physically discrete unit of a therapeutic composition to be administered to a subject. Each unit contains a predetermined quantity of active material (e.g., a therapeutic agent such as an anti-fPSA antibody).

In some embodiments, the predetermined quantity is one that has been correlated with a desired therapeutic effect when administered as a dose in a dosing regimen. Those of ordinary skill in the art appreciate that the total amount of a therapeutic composition or agent administered to a particular subject is determined by one or more attending physicians and may involve administration of multiple dosage forms Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses. In some embodiments, a dosing regimen is or has been correlated with a desired therapeutic outcome, when administered across a population of patients.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Free PSA: the term "free PSA" or "fPSA", as used herein, refers to any form of PSA or precursor of PSA that is not bound by protease inhibitors such as example alpha1-antichymotrypsin, and is in close proximity to or associated with prostate cancer cells or metastatic diseases thereof (i.e., is not a serum marker).

Functional: As used herein, a "functional" biological molecule is a biological molecule in a form in which it exhibits a property and/or activity by which it is characterized. A biological molecule may have two functions (i.e., bifunctional) or many functions (i.e., multifunctional).

Gene: As used herein, the term "gene" has its meaning as understood in the art. In some embodiments, the term "gene" may include gene regulatory sequences (e.g., promoters, enhancers, etc.) and/or intron sequences. In some embodiments, the term refers to nucleic acids that do not encode proteins but rather encode functional RNA molecules such as tRNAs, RNAi-inducing agents, etc. Alternatively or additionally, in many embodiments, the term "gene", as used in the present application, refers to a portion of a nucleic acid that encodes a protein. Whether the term encompasses other sequences (e.g., non-coding sequences, regulatory sequences, etc) will be clear from context to those of ordinary skill in the art.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Homology: As used herein, the term "homology" refers to the overall relatedness between polymeric molecules, e.g., between polypeptide molecules. In some embodiments, polymeric molecules such as antibodies are considered to be "homologous" to one another if their sequences are at least 80%, 85%, 90%, 95%, or 99% identical. In some embodiments, polymeric molecules are considered to be "homologous" to one another if their sequences are at least 80%, 85%, 90%, 95%, or 99% similar.

Marker: A marker, as used herein, refers to an agent whose presence or level is a characteristic of a particular tumor or metastatic disease thereof. For example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present invention a useful marker need not distinguish tumors of a particular subclass with 100% accuracy.

Patient: As used herein, the term "patient" or "subject" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, such cancer or tumor is or comprises a cancer of the prostate, or tumor in the prostate. In some embodiments, the disorder or condition is metastatic prostate cancer.

Peptide: The term "peptide" refers to two or more amino acids joined to each other by peptide bonds or modified peptide bonds. In particular embodiments, "peptide" refers to a polypeptide having a length of less than about 100 amino acids, less than about 50 amino acids, less than 20 amino acids, or less than 10 amino acids.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Prognostic and predictive information: As used herein, the terms prognostic and predictive information are used interchangeably to refer to any information that may be used to indicate any aspect of the course of a disease or condition either in the absence or presence of treatment. Such information may include, but is not limited to, the average life expectancy of a patient, the likelihood that a patient will survive for a given amount of time (e.g., 6 months, 1 year, 5 years, etc.), the likelihood that a patient will be cured of a disease, the likelihood that a patient's disease will respond to a particular therapy (wherein response may be defined in any of a variety of ways). Prognostic and predictive information are included within the broad category of diagnostic information.

Protein: As used herein, the term "protein" refers to a polypeptide (i.e., a string of at least 3-5 amino acids linked to one another by peptide bonds). Proteins may include moieties other than amino acids (e.g., may be glycoproteins, proteoglycans, etc.) and/or may be otherwise processed or modified. In some embodiments "protein" can be a complete polypeptide as produced by and/or active in a cell (with or without a signal sequence); in some embodiments, a "protein" is or comprises a characteristic portion such as a polypeptide as produced by and/or active in a cell. In some embodiments, a protein includes more than one polypeptide chain. For example, polypeptide chains may be linked by one or more disulfide bonds or associated by other means. In some embodiments, proteins or polypeptides as described herein may contain L-amino acids, D-amino acids, or both, and/or may contain any of a variety of amino acid modifications or analogs known in the art. Useful modifications include, e.g., terminal acetylation, amidation, methylation, etc. In some embodiments, proteins or polypeptides may comprise natural amino acids, non-natural amino acids, synthetic amino acids, and/or combinations thereof. In some embodiments, proteins are or comprise antibodies, antibody polypeptides, antibody fragments, biologically active portions thereof, and/or characteristic portions thereof.

Response: As used herein, a response to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a tumor's response. Tumor or subject response may be measured according to a wide variety of criteria, including clinical criteria and objective criteria. Techniques for assessing response include, but are not limited to, clinical examination, positron emission tomatography, chest X-ray CT scan, MRI, ultrasound, endoscopy, laparoscopy, presence or level of tumor markers in a sample obtained from a subject, cytology, and/or histology. Many of these techniques attempt to determine the size of a tumor or otherwise determine the total tumor burden. Methods and guidelines for assessing response to treatment are discussed in Therasse et. al., "New guidelines to evaluate the response to treatment in solid tumors", European Organization for Research and Treatment of Cancer, National Cancer Institute of the United States, National Cancer Institute of Canada, *J. Natl. Cancer Inst.*, 2000, 92(3):205-216. The exact response criteria can be selected in any appropriate manner, provided that when comparing groups of tumors and/or patients, the groups to be compared are assessed based on the same or comparable criteria for determining response rate. One of ordinary skill in the art will be able to select appropriate criteria.

Sample: As used herein, a sample obtained from a subject may include, but is not limited to, any or all of the following: a cell or cells, a portion of tissue, blood, serum, ascites, urine, saliva, and other body fluids, secretions, or excretions. The term "sample" also includes any material derived by processing such a sample. Derived samples may include nucleotide molecules or polypeptides extracted from the sample or obtained by subjecting the sample to techniques such as amplification or reverse transcription of mRNA, etc.

Specific binding: As used herein, the terms "specific binding" or "specific for" or "specific to" refer to an interaction (typically non-covalent) between a target entity (e.g., a target protein or polypeptide) and a binding agent (e.g., an antibody, such as a provided antibody). As will be understood by those of ordinary skill, an interaction is considered to be "specific" if it is favored in the presence of alternative interactions. In many embodiments, an interaction is typically dependent upon the presence of a particular structural feature of the target molecule such as an antigenic determinant or epitope recognized by the binding molecule. For example, if an antibody is specific for epitope A, the presence of a polypeptide containing epitope A or the presence of free unlabeled A in a reaction containing both free labeled A and the antibody thereto, will reduce the amount of labeled A that binds to the antibody. It is to be understood that specificity need not be absolute. For example, it is well known in the art that numerous antibodies cross-react with other epitopes in addition to those present in the target molecule. Such cross-reactivity may be acceptable depending upon the application for which the antibody is to be used. In particular embodiments, an antibody specific for fPSA has less than 10% cross-reactivity with PSA bound to protease inhibitors (e.g., ACT). One of ordinary skill in the art will be able to select antibodies having a sufficient degree of specificity to perform appropriately in any given application (e.g., for detection of a target molecule, for therapeutic purposes, etc.). Specificity may be evaluated in the context of additional factors such as the affinity of the binding molecule for the target molecule versus the affinity of the binding molecule for other targets (e.g., competitors). If a binding molecule exhibits a high affinity for a target molecule that it is desired to detect and low affinity for non-target molecules, the antibody will likely be an acceptable reagent for immunodiagnostic purposes. Once the specificity of a binding molecule is established in one or more contexts, it may be employed in other, preferably similar, contexts without necessarily re-evaluating its specificity.

Stage of cancer: As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition (prostate cancer) has been diagnosed with and/or exhibits one or more symptoms of the disease, disorder, or condition. Prostate tumors are frequently asymptomatic. In some embodiments, an individual who is suffering from prostate cancer prostrate tumors, but does not display any symptoms of prostate cancer and/or has not been diagnosed with prostate cancer. In some embodiments, an individual who is suffering from prostate cancer is an individual who has increased tumor-associated or intra-tumoral fPSA or PSA relative to an individual who does not have prostate cancer.

Symptoms are reduced: According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom. Many prostate cancer patients with smaller tumors have no symptoms. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutic agent: As used herein, the phrase "therapeutic agent" refers to any agent that has a therapeutic effect and/or elicits a desired biological and/or pharmacological effect, when administered to a subject.

Therapeutically effective amount: As used herein, the term "therapeutically effective amount" refers to an amount of a therapeutic protein (e.g., fPSA antibody) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating") refers to any administration of a substance (e.g., anti-fPSA antibodies or AR antagonists) that partially or completely alleviates, ameliorates, relives, inhibits, delays onset of, reduces severity of, and/or reduces incidence of one or more symptoms, features, and/or causes of a particular disease, disorder, and/or condition (e.g., prostate cancer). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION OF CERTAIN EMBODIMENTS

Clinical markers are frequently used for diagnosis of prostate cancer as well as assessments of treatment efficacy. The most widespread clinical marker of prostate cancer is prostate specific antigen ("PSA"). PSA is a serine protease and member of the tissue kallikrein family of proteases. It is produced primarily by prostate ductal and acinar epithelium and is secreted into the lumen, where its function is to cleave semenogelin I and II in the seminal coagulum. However, both cancer and a number of more benign conditions change the architecture of the prostate gland, allowing PSA to leak into the perivascular space and escape into the bloodstream.

PSA, though abundantly expressed within the prostate tissue, is almost undetectable in the serum of men with healthy prostates. The presence of elevated PSA levels, often indicates prostate trauma or disease. Serum PSA exists in two forms: a free-floating, catalytically active form and a form that is complexed or bound with other proteins. Standard PSA tests measure the relative or qualitative amounts of both forms, which can help differentiate whether the cause of elevated PSA is prostate cancer or some other condition. The serum PSA test determines the ratio between free or uncomplexed PSA ("fPSA") in the blood and the total PSA (free plus bound PSA). A lower ratio of fPSA to total PSA indicates a higher potential that the individual does, in fact, have prostate cancer. Total serum PSA levels above 10 ng/ml also indicate more than a 50% chance of prostate cancer according to clinical practice guidelines. Serum PSA levels between 4-10 ng/ml are a clinical indication of need for a prostate biopsy to verify whether cancer is in fact present.

Nonetheless, even the more refined levels of serum testing demonstrate significant limitations, particularly in regard assessing the efficacy of treatment. The more removed a biomarker or antigen becomes from the focus of treatment (i.e., tumor), the more difficult it becomes to assess whether fluctuations in the levels of the biomarker or antigen are truly the result of treatments or represent artifacts caused by intervening phenomena. In short, it is harder to determine the correlation between cause and effect. Furthermore, because all serum markers are separated from the origin of disease, the correlation between quantified levels and disease severity or progression is necessarily imperfect. Moreover, information regarding stage, tumor characteristics, the likelihood of recovery and therapeutic assessments typically require either advanced imaging or invasive biopsy. No serum-based marker can truly provide the specific, real-time information, including potentially morphology, which can be derived from intratumoral diagnostics.

PSA is expressed at a high level in the luminal epithelial cells of the prostate and is absent or expressed at very low levels in other tissues. PSA expression is increased by androgens via several androgen-responsive gene regulatory elements, and the development of prostate cancer is particularly driven by androgens, specifically testosterone. Thus, therapies that counter the effects of androgen (i.e., anti-androgen therapies), including removal of androgen-producing tissues, represent attractive targets for treatment of prostate cancer. Traditional anti-androgen therapeutics work directly upon the androgen receptor to block activation by androgens.

PSA is far from a perfect serum marker for prostate cancer. The fact that it can be present in serum due to a number of more benign conditions significantly raises the risk of false-positive results. Prostate inflammation, infection, and benign prostatic hyperplasia ("BPH") can all increase levels of serum PSA. In other words, there is no form of serum PSA that is actually specific for prostate cancer. Moreover, serum PSA levels are imperfectly correlated with disease and therapeutic efficacy. For example, the fact that PSA levels are reduced by half following a course of treatment is not correlated with, and does not suggest, that the number of cancerous cells in the body is reduced by half. The ability to detect PSA in serum not only requires expression but also secretion and leakage into the circulation, which are two processes that are poorly understood. Additional difficulties arise from the fact that only a very small percentage of tumor-generated PSA is secreted into the perivascular space, and the rate-determining step to serum circulation is undefined.

Standard serum total PSA tests also lack the sensitivity and specificity to detect a large fraction of early-stage tumors and are wholly inadequate for detection of prostate cancer-derived metastatic tumors. For example, bone is the most common site of metastatic spread in prostate cancer, but it is particularly challenging to characterize because most detection technologies (e.g., nuclear medicine technologies such as $^{99m}$Tc-MDP, $^{18}$F-NaF) do not directly image the metastatic disease but, rather, target nearby normal bone repair. Therefore, existing technologies cannot distinguish between malignant and non-malignant disease. Furthermore, responses to anti-androgen therapy cannot be efficiently assessed since resolution of tumor-induced bone repair can lag clinical responses by months or years.

Embodiments of the present invention are drawn to antibody-based monitoring and quantification of androgen receptor ("AR") signaling via tumor-associated or intratumoral fPSA and antibody-based targeting of intratumoral fPSA for therapeutic applications. The inventions disclosed herein are facilitated in part by the surprising discovery that antibodies and antibody polypeptides specific for the catalytic cleft PSA selectively bind fPSA, including and preferentially as disclosed for the first time herein, tumor-associated and intratumoral fPSA. The abilities of catalytic cleft-specific antibodies to bind fPSA at tumors in situ enables numerous diagnostic and therapeutic applications. For example, labeled antibody that quantitatively binds tumor-associated fPSA can directly monitor responses to anti-androgen therapy in situ rather than indirectly through serum levels of PSA. Successful treatments result in a reduction in AR signaling (e.g., through pharmaceutical compounds that block activation of the receptor), which may be reflected in a detectable decrease in the signal of the labeled antibody. It will be apparent to those of skill in the art that embodiments of the invention are applicable to any therapy that blocks androgen receptors or causes apoptosis (e.g., chemotherapy), as well as any treatment that directly or indirectly reduces AR levels (i.e., siRNA).

In addition, methods disclosed herein possess the ability to diagnose and treat diffuse prostate disease; i.e., metastatic disease in which prostate-derived cancer cells have metastasized to other organs or tissues of the body. As discussed above, detection, monitoring and treatment of metastatic prostate cancer has proven particularly difficult. Surgical excision of metastatic lymph nodes, for example, frequently fails to remove all of the cancerous cells that may be present, greatly increasing the chances of recurrence. Moreover, current methods of monitoring of bone metastases are wholly inadequate as they image nearby normal bone repair rather than directly imaging the tumor, meaning that most scans cannot distinguish between malignant and non-malignant disease (i.e., other diseases that result in bone remodeling).

PSA in the serum is largely covalently attached to the serum protease inhibitor alpha1-antichymotrypsin (ACT) and is referred to complexed PSA ("cPSA"). A relatively minor portion is present as non-complexed fPSA. However, it has been discovered that a much greater proportion of fPSA is associated in close proximity to prostate tumors or even intratumoral. fPSA contains different molecular forms of active and inactive PSA. Subforms of fPSA, as defined herein, include BPSA and pro-PSA ("pPSA"). BPSA is identical to native mature PSA but has 2 internal peptide bond cleavages at Lys182 and Lys145. It is associated with nodular hyperplasia within the inner portion, or "transition zone" of the prostate, while cancers typically develop within the outer portion, or "peripheral zone". BPSA is elevated in the prostate transition zone and is associated with pathologic BPH. pPSA is associated with prostate tumor itself. Together these forms represent individual forms of fPSA that are highly disease-specific.

Capabilities of fPSA in the evaluation and treatment of prostate cancer and diffuse disease are particularly evident when used in conjunction with molecular imaging. Molecular imaging in oncology is the noninvasive imaging of key molecules and molecular-based events that are fundamental to human tumor biology. It can provide previously unavailable information regarding detection, differential diagnosis, tumor biology indicating proper therapeutic course, staging, reoccurrence and response to therapy. Nuclear medicine techniques in particular lend themselves to molecular imaging. Via radioactivity detectors, biomolecular radiotracers may be used to detect the real-time biochemistry of tumors, cancerous cells, and differentiated normal tissues, thereby providing qualitative or quantitative biochemical or functional information about human tumors and tissues.

Advances in molecular imaging have been facilitated through the development and improvement of monoclonal antibody technology. In addition to their recognized potential for cancer-targeted pharmaceuticals, monoclonal antibodies can be used as disease-specific contrast agents for diagnostic imaging. For example, by combining the high sensitivity and resolution of a positron emission tomography ("PET") camera with the specificity of a monoclonal antibody, immuno-PET, the combination of PET with monoclonal antibodies, is an attractive, novel option to improve diagnostic tumor characterization. It will be appreciated, however, that concepts disclosed herein are not based on any single imaging technology. In fact, it is a protean technology adaptable to the use of almost any imaging parameter to infer qualitative or quantitative biochemical or functional information about human tumors and tissues. Molecular imaging methods encompassed by the present disclosure include gamma camera imaging, single-photon emission computed tomography, positron emission tomography, magnetic resonance spectroscopy, magnetic resonance imaging, optical imaging (macroscopic spectral imaging), and ultrasound.

Immuno-PET is equivalent to comprehensive immunohistochemical staining in vivo, for which purpose the monoclonal antibody must be labeled with a positron emitter to enable visualization with a PET camera. However, there remains a need for the development of a new generation of monoclonal antibody-based imaging probes or novel radiotracers in addition to existing PET tracers, of which the non-tumor-specific metabolic tracer 18-fluoro-2-deoxy-D-glucose ($^{18}FDG$) is currently used in >90% of all PET imaging procedures.

Deliberately engineering radiotracers to achieve success in tumors has proven challenging, resulting in the high attrition rate of novel radiotracers in the clinic. The target of a radiotracer necessarily frames its potential context of use (i.e. detection, response indicator), and candidates are often selected on the basis of preclinical evidence pointing to an upregulation in cancer. In this regard, it can be challenging to appropriately evaluate novel radiotracers in patients without a thorough appreciation of the patho-biological mechanism of target upregulation.

A particular embodiment of this invention has achieved success in this regard by demonstrating that changes in prostate-specific, androgen receptor-regulated gene expression and resulting translational products can be measured non-invasively with novel radiotracers derived from appropriately labeled antibodies specific to tumor-associated fPSA. Radiotracers disclosed herein are highly specific for prostate cancer cells in an androgen receptor-dependent manner and can detect androgen-regulated elevations in fPSA expression, demonstrating their ability to reflect intratumoral androgen receptor signaling. In conjunction with imaging technologies known to those of skill in the art, the novel radiotracers disclosed herein allow for in situ quantification of androgen receptor signaling via changes in fPSA synthesis in response to pharmacological inhibition of the androgen receptor. Moreover, the radiotracers possess unique specificity for metastatic prostate cancer tumors in bone and can clearly distinguish between a true skeletal prostate cancer lesion and bone remodeling.

The ability of embodiments of the invention to monitor and image androgen receptor signaling is applicable in a wide range of diagnostic methods. Embodiments of the invention can provide diagnostic information, and prognostic and predictive information related to prostate cancer and metastisis of prostate cancer cells. As mentioned previously, the ability to monitor tumor-associated androgen receptor signaling facilitates extremely accurate measurements of therapeutic efficacy, particularly when anti-androgen treatments are used. In this capacity, embodiments of the invention can indicate when cancerous cells have developed adaptive mutations that render the cells unresponsive to androgen receptor signaling. Furthermore, embodiments of the invention can be used to assess the stage of cancer and/or to provide information on the likely outcome of treatment. Embodiments of the invention can also predict whether a given course of therapy will be successful. For example, an elevated level of androgen receptor signaling relative to a baseline reference may suggest a particularly aggressive course of anti-androgen treatment.

It is also appreciated that the tumor-associated and intratumoral specificity of the anti-fPSA antibodies and antibody polypeptides disclosed herein permit targeting of anti-androgen and anti-cancer treatments to cells that express and/or display fPSA. Tumor-associated fPSA antibodies may be coupled to radioactive elements, cytotoxic nucleic acid analogues, apoptosis-inducing agents, and potentially any therapy now known or later developed that could benefit from accurate delivery to a specific population of cells. By binding solely to the catalytic cleft of PSA, which is blocked by ACT in serum, the fPSA antibodies and antibody polypeptides disclosed herein have the ability to target therapies directly to prostate-specific tumors and prostate cancer cells (e.g., prostate cancer-derived metastatic bone disease). Without being bound by any particular theory, it is believed that fPSA transiently exists as a proteolytically active integral membrane protein, then is transiently present in the pericellular space prior to sequestration by extracellular binding proteins (e.g., ACT) that preclude recognition by catalytic cleft-specific antibodies.

Embodiments of the present invention and methods disclosed herein can include any antibody now known or later discovered that is capable of specific binding to fPSA, particularly tumor-associated fPSA. As described above, the present invention also encompasses antibody fragments and characteristic portions of antibodies (e.g., 5A10) capable of specific binding to fPSA. Select antibodies and antibody fragments may be used individually or in combination. When used in combination, the select antibodies and antibody fragments may be used simultaneously or sequentially. Antibodies and antibody fragments of the invention demonstrate peak tumor associate between approximately about 12-48 hours post-administration, and in a particular embodiments within 20-30 post-administration. In specific embodiments, peak tumor-associated activity is observed at approximately about 24 hours post-administration.

Some embodiments of the invention utilize a monoclonal or polyclonal antibody (or characteristic fragment thereof) capable of specifically binding to a PSA epitope that is only accessible when the PSA is not complexed (e.g., is not bound by ACT or other protein). Antibodies for use in embodiments of the invention may be from any species, e.g., human, mouse, rabbit, etc. As described above, the accessibility of the epitopes within or nearby (e.g., adjacent to) the catalytic cleft is as important distinguishing characteristic between fPSA (particularly intratumoral or cell-associated fPSA) and serum PSA. In some embodiments of the invention, the epitope is within the catalytic cleft. In some embodiments of the invention, the epitope is adjacent to the catalytic cleft. One such antibody for use in embodiments of the invention is 5A10, a mouse monoclonal antibody that specifically recognizes an epitope adjacent to the catalytic cleft of fPSA. 5A10 was raised against seminal plasma PSA, and its epitope is almost inaccessible PSA is complexed to ACT. See, e.g., Lilja, H. et al., *Clin. Chem.*, 1991, 37:1618-1625. In some embodiments of the invention, the antibody is 4G10.

In some embodiments, antibodies for use in the present invention may bind linear epitopes comprising amino acids 80-91 in fPSA, which form part of the so-called kallikrein loop. In some embodiments, the antibodies bind fPSA sequence SWGSEPC (SEQ ID NO: 2) (amino acids 204-210 in PSA). This SWG site forms part of the epitope of MAbs specific for fPSA. Amino acids 204-207 (SWGS) (SEQ ID NO: 3) form the edge of the groove containing the active site residues of PSA opposite the region 80-91 on the other side of the groove. In some embodiments, the antibodies bind fPSA sequence HPQKV (SEQ ID NO: 4) (amino acids 164-168 in PSA), which is located adjacent to amino acids 204-207 and may form part of the epitope for monoclonal antibodies specific for fPSA. In some embodiments, the antibodies bind in the region of amino acids 164-168 in fPSA. In a particular embodiment, the antibody that binds in the region of amino acids 164-168 is 5A10. In some embodiments, antibodies specifically bind residues on at least one of three different conformational loops fof PSA, i.e., amino acids 80-91, 164-168, and 204-207. See, Leinonen, J. et al, *Clin. Chem.*, 2002, 48(12): 2208-2216.

The development of additional fPSA-specific antibodies is within the capabilities of one of ordinary skill in the art based upon published PSA epitope characterization/structure analyses and the methods discussed immediately below. Exemplary PSA epitope characterizations are described in: Lilja, H. et al., *Clin. Chem.*, 1991, 37:1618-1625; Pettersson, K. et al., *Clin. Chem.*, 1995, 41: 1480-1488; Piironen, T., *Protein Sci.*, 1998, 7: 259-269; and Menez, R., *J. Mol. Biol.*, 2008, 376(4): 1021-1033; Leinonen, J. et al, *Clin. Chem.*, 2002, 48(12): 2208-2216, and Villoutreix B. O., et al., *Protein Sci.*, 1994, 3:2033-2044, each of which is incorporated herein by reference in their entirety.

Humanized and Veneered Antibodies

Monoclonal antibodies for use in embodiments of the invention may be developed by conventional means well known to those of skill in the art; hybridoma technology is but one example. See, e.g., G. Kohler and C. Milstein, *Nature*, 1975, 256: 495-497. Protocols for production of monoclonal antibodies and the cell lines that produce them are well known in the art. See, e.g., Gerhard et al, *Proc. Natl. Acad. Sci. USA*, 1978, 75:1510; *Monoclonal Antibodies* (R. Kennett, T. McKeam, & K. Bechtol eds. 1980); *Monoclonal Antibodies and T-Cell Hybridomas* (G. Hammerling, U. Hammerling, & J. Kearney eds. 1981); Kozbor et al, *Proc. Natl. Acad. Sci. USA*, 1982, 79:6651; Jonak et al, *Hybridoma*, 1983, 2:124; *Monoclonal Antibodies and Functional Cell Lines* (R. Kennett, K. Bechtol, & T. McKearn eds. 1983); and Shulman et al, *Nature*, 1982, 276:269-270.

In certain embodiments, particularly when using an anti-fPSA antibody for therapeutic purposes, a humanized or veneered antibody may be used to reduce any potential immunogenic reaction. In general, humanized or veneered antibodies minimize unwanted immunological responses that limit the duration and effectiveness of therapeutic applications of non-human antibodies in human recipients.

A number of methods for preparing humanized antibodies comprising an antigen-binding portion derived from a non-human antibody have been described in the art. In particular, antibodies with rodent variable regions and their associated complementarity-determining regions (CDRs) fused to human constant domains have been described (e.g., see Winter et al., *Nature*, 1991, 349:293; Lobuglio et al., *Proc. Nat. Acad. Sci. USA*, 1989, 86:4220; Shaw et al., *J. Immunol.*, 1987, 138:4534; and Brown et al., *Cancer Res.*, 1987, 47:3577). Rodent CDRs grafted into a human supporting framework region (FR) prior to fusion with an appropriate human antibody constant domain (e.g., see Riechmann et al., *Nature*, 1988, 332:323; Verhoeyen et al., *Science*, 1988, 239:1534; and Jones et al. *Nature*, 1986, 321:522) and rodent CDRs supported by recombinantly veneered rodent FRs have also been described (e.g., see EPO Patent Pub. No. 519,596).

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes (e.g., see Lonberg and Huszar, *Int. Rev. Immunol.*, 1995, 13:65-93 and U.S. Pat. Nos. 5,545,806; 5,569, 825; 5,625,126; 5,633,425; and 5,661,016).

Completely human antibodies or antigen-binding fragments thereof can also be identified and isolated from human antibody libraries. For example, expression products of a polynucleotide library encompassing the theoretical diversity of human antibodies ($10^{12th}$ different antibodies), or physically realizable subportion thereof, can be screened with the totality and/or antigenic portions of the catalytic cleft to identify novel interacting antibodies or fragments. Exemplary libraries include phage-display libraries from immunized individuals (see, e.g., Barbas et al., *J. Mol. Biol.*, 1993, 230:812-823), libraries of germline sequences (Griffiths et al., *EMBO J.,* 1994, 13: 3245-3260) or naïve B-cell repertoires (Vaughan et al., *Nature Biotech.,* 1996, 14:309-314). In particular embodiments, a library derived from a donor suffering from prostate cancer may be used. In such libraries, PSA antigen stimulation increases mRNA production in B cells, which contributes to the isolation of heavy and light variable genes that are predisposed to PSA binding.

Synthetic libraries, in which germline antibody gene segments (VH, DH, and JH or Vκ/λ and Jκ/λ) are cloned and arranged combinatorially in vitro so as to reconstitute genes encoding complete VH and VL chains (see, e.g., Winter, *FEBS Letters,* 1998, 430:92-94), may also be used. See, e.g., de Kruif et al., *J. Mol. Biol.,* 1995, 248: 97-105; Griffiths et al., *EMBO J,* 1994, 13: 3245-3260; Hoogenboom and Winter, *J. Mol. Biol.,* 1992, 227:381-388; and Nissim et al., *EMBO J.,* 1994, 13:692-698. Semi-synthetic libraries, which are generated by selecting one or more antibody frameworks as a scaffold and randomizing sequences within the CDR loops, may also be used. Particular libraries may have fully or partially randomized CDR3 hypervariable regions of the heavy and/or light chains (see, e.g., Huls et al., *Nat. Biotech.,* 1999, 17:276-281; Knappik et al. (*J. Mol. Biol.,* 2000, 296: 57-86). See generally, Fuh, G. *Expert. Opin. Biol. Ther.,* 2007, 7(1): 73-87; Kim et al., *Mol. Cells,* 2005, 20(1): 17-29. Phage, yeast, *E. coli* and ribosome display technologies may be used for library screening.

Veneered versions of anti-fPSA antibodies may also be used in the methods of the present invention. The process of veneering involves selectively replacing FR residues from, e.g., a murine heavy or light chain variable region, with human FR residues in order to provide an antibody that comprises an antigen-binding portion that retains substantially all of the native FR protein folding structure. Veneering techniques are based on the understanding that antigen-binding characteristics are determined primarily by the structure and relative disposition of the heavy and light chain CDR sets within the antigen-association surface (e.g., see Davies et al., *Ann. Rev. Biochem.,* 1990, 59:439). Thus, antigen association specificity can be preserved in a humanized antibody only wherein the CDR structures, their interaction with each other and their interaction with the rest of the variable region domains are carefully maintained. By using veneering techniques, exterior (e.g., solvent-accessible) FR residues that are readily encountered by the immune system are selectively replaced with human residues to provide a hybrid molecule that comprises either a weakly immunogenic, or substantially non-immunogenic veneered surface.

Diagnostic Applications

In some embodiments, provided antibodies are used for diagnostic applications. By virtue of the tumor-associated fPSA specificity of the antibodies disclosed herein, diagnostic assays may be employed to monitor the effects of various therapies upon androgen receptor signaling in situ at the actual location of the tumor, as opposed to indirectly through serum PSA. For example, the production of PSA gene products is positively regulated by the androgen receptor ("AR"). The AR is a nuclear receptor that is activated by binding of androgenic hormones in the cytoplasm. Activated ARs translocate into the nucleus where they can bind androgen response elements in the regulatory regions of target genes. Thus, prostate cancer treatments that block or reduce androgen levels or AR activation are reflected in a corresponding decrease in androgen regulated gene products such as fPSA. Some embodiments of the inventor monitor this effect in situ.

Diagnostic applications may also be able to detect the presence or absence of metastatic prostate cancer disease, for example in the liver, lymph nodes or bone. In general the fPSA-specific antibodies provided herein may be administered before, during, or after any prostate cancer-related treatment (e.g., anti-androgen treatments) to assess the effects of the treatment upon androgen-receptor signaling relative to a subject-specific baseline or a baseline derived from a population of patients. In particular embodiments, a population-derived baseline may comprise the mean or median of androgen receptor signaling levels of fPSA expression or activity in a group of patient or subjects that is not suffering from prostate cancer.

In certain embodiments, binding can be detected by adding a detection entity to a provided antibody as discussed in the following section. In certain embodiments, the detection techniques of the present invention will include a negative control, which can involve applying the test to a control sample (e.g., from a normal non-cancerous tissue) so that the signal obtained thereby can be compared with the signal obtained from the sample being tested.

Particular diagnostic techniques for use in embodiments of the invention include, but are not limited to, enzyme linked immunosorbent assays ("ELISA"), positron emission tomography, Western blotting, immunohistochemistry, and magnetic resonance imaging.

Detection Entities

In some embodiments, anti-fPSA specific antibodies are used for and with detection applications. Multifunctional agents described herein may be used which comprise at least one detection entity, in addition to a provided antibody as described herein.

A detection entity may be any entity that allows detection of fPSA antibody or antibody polypeptides after binding to a fPSA in a tissue of interest; e.g., prostate cancer cells or bone. Any of a wide variety of detectable agents can be used as detection entity (e.g., labeling moieties) in multifunctional antibody agents of the provided antibodies. A detection entity may be directly detectable or indirectly detectable. Examples of detection entities include, but are not limited to: various ligands, radionuclides (e.g., $^{3}H$, $^{14}C$, $^{18}F$, $^{19}F$, $^{32}P$, $^{35}S$, $^{135}I$, $^{125}I$, $^{123}I$, $^{64}Cu$, $^{187}Re$, $^{111}In$, $^{90}Y$, $^{99m}Tc$, $^{177}Lu$, $^{89}Zr$, etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

In certain embodiments, a detection entity comprises a fluorescent label. Numerous known fluorescent labeling moieties of a wide variety of chemical structures and physical characteristics are suitable for use in the present invention. Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, β carboxyfluorescein or FAM, etc.), carbocyanine, merocyanine, styryl dyes, oxonol dyes, phycoerythrin, erythrosin, eosin, rhodamine dyes (e.g., carboxytetramethyl-rhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514, etc.), Texas Red, Texas Red-X, Spectrum Red™, Spectrum Green™, cyanine dyes (e.g., Cy-3™, Cy-5™, Cy-3.5™, Cy-5.5™ etc.), Alexa Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660, Alexa Fluor 680, etc.), BODIPY dyes (e.g., BODIPY FL, BODIPY R6G, BODIPY TMR, BODIPY TR, BODIPY 530/550, BODIPY 558/568, BODIPY 564/570, BODIPY 576/5$^{89}$, BODIPY 581/591, BODIPY 630/650, BODIPY 650/665, etc.), IRDyes (e.g., IRD40, IRD 700, IRD 800, etc.), and the like. For more examples of suitable fluorescent dyes and methods for coupling fluorescent dyes to other chemical entities such as proteins and peptides, see, for example, "The Handbook of Fluorescent Probes and Research Products", 9111 Ed., Molecular Probes, Inc., Eugene, Oreg.

Favorable properties of fluorescent labeling agents include high molar absorption coefficient, high fluorescence quantum yield, and photostability. In certain embodiments, labeling fluorophores desirably exhibit absorption and emission wavelengths in the visible (i.e., between 400 and 750 nm) rather than in the ultraviolet range of the spectrum (i.e., lower than 400 nm).

In certain embodiments, a detection entity comprises an enzyme. Examples of suitable enzymes include, but are not limited to, those used in an ELISA, e.g., horseradish peroxidase, beta-galactosidase, luciferase, alkaline phosphatase, etc. Other examples include beta-glucuronidase, beta-D-glucosidase, urease, glucose oxidase, etc. An enzyme may be conjugated to a targeting entity (e.g., chlorotoxin moiety) using a linker group such as a carbodiimide, a diisocyanate, a glutaraldehyde, and the like. More detailed description of suitable linkers is provided elsewhere herein.

In certain embodiments, a detection entity comprises a radioisotope that is detectable by Single Photon Emission Computed Tomography (SPECT) or Position Emission Tomography (PET). The high resolution and quantitative imaging of PET is particularly suited to certain embodiments of the invention. Examples of such radionuclides include, but are not limited to, zirconium-89 ($^{89}$Zr), iodine-124 ($^{124}$I), iodine-131 ($^{131}$I), iodine-125 ($^{125}$I), bismuth-212 ($^{212}$Bi), bismuth-213 ($^{213}$Bi), astatine-211 ($^{211}$At), copper-67 ($^{67}$Cu), copper-64 ($^{64}$Cu), rhenium-186 ($^{186}$Re), rhenium-188 ($^{188}$Re), phosphorus-32 ($^{32}$P), samarium-153 ($^{153}$Sm), lutetium-177 ($^{177}$Lu), technetium-99m ($^{99m}$Tc), gallium-67 ($^{67}$Ga), indium-111 ($^{111}$In), and thallium-201 ($^{201}$Tl). Particular procedures for the production and use of $^{89}$Zr-labeled monoclonal antibodies are disclosed in Verel, I. et al. "$^{89}$Zr-Immuno-PET: Comprehensive Procedures for the Production of $^{89}$Zr-Labeled Monoclonal Antibodies", J. Nucl. Med. 2003; 44:1271-1281, incorporated by reference herein.

In certain embodiments, a labeling moiety comprises a radioisotope that is detectable by Gamma camera. Examples of such radioisotopes include, but are not limited to, iodine-131 ($^{131}$I), and technetium-99m ($^{99m}$Tc).

In certain embodiments, a detection entity comprises a paramagnetic metal ion that is a good contrast enhancer in Magnetic Resonance Imaging (MRI). Examples of such paramagnetic metal ions include, but are not limited to, gadolinium III (Gd3+), chromium III (Cr3+), dysprosium III (Dy3+), iron III (Fe3+), manganese II (Mn2+), and ytterbium III (Yb3+). In certain embodiments, the detection entity comprises gadolinium III (Gd3+). Gadolinium is an FDA-approved contrast agent for MRI, which accumulates in abnormal tissues causing these abnormal areas to become very bright (enhanced) on the magnetic resonance image. Gadolinium is known to provide great contrast between normal and abnormal tissues in different areas of the body, in particular in the brain.

In certain embodiments, a labeling moiety comprises a stable paramagnetic isotope detectable by nuclear magnetic resonance spectroscopy (MRS). Examples of suitable stable paramagnetic isotopes include, but are not limited to, carbon-13 ($^{13}$C) and fluorine-19 ($^{19}$F).

Pharmaceutical Compositions

The present invention also provides compositions comprising one or more provided antibodies, fragments or characteristic portions thereof. In some embodiments, the present invention provides at least one antibody and at least one pharmaceutically acceptable excipient. Such pharmaceutical compositions may optionally comprise and/or be administered in combination with one or more additional therapeutically or biologically active substances. In some embodiments, provided pharmaceutical compositions are useful in medicine or the manufacture of medicaments. In some embodiments, provided pharmaceutical compositions are useful as prophylactic agents (i.e., vaccines) in the treatment or prevention of prostate cancer and metastases thereof. In some embodiments, provided pharmaceutical compositions are useful in therapeutic applications, for example in individuals suffering from prostate cancer; e.g., as delivery vehicles capable of specifically targeting cytotoxic agents or compounds that block androgen receptor signaling. In some embodiments, the pharmaceutical compositions are simultaneously useful in diagnostic applications and therapeutic applications. In some embodiments, pharmaceutical compositions are formulated for administration to humans. In some embodiments, the pharmaceutical compositions comprise an anti-fPSA antibody in combination with or conjugated to an anti-cancer agent as defined herein.

For example, pharmaceutical compositions may be provided in a sterile injectable form (e.g., a form that is suitable for subcutaneous injection or intravenous infusion). In some embodiments, pharmaceutical compositions are provided in a liquid dosage form that is suitable for injection. In some embodiments, pharmaceutical compositions are provided as powders (e.g., lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

In some embodiments, provided pharmaceutical compositions comprise one or more pharmaceutically acceptable excipients (e.g., preservative, inert diluent, dispersing agent, surface active agent and/or emulsifier, buffering agent, etc.). In some embodiments, pharmaceutical compositions comprise one or more preservatives. In some embodiments, pharmaceutical compositions comprise no preservatives.

In some embodiments, pharmaceutical compositions are provided in a form that can be refrigerated and/or frozen. In some embodiments, pharmaceutical compositions are provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer). In some embodiments, storage of antibody compositions for longer than the specified time results in antibody degradation.

Liquid dosage forms and/or reconstituted solutions may comprise particulate matter and/or discoloration prior to administration. In some embodiments, a solution should not be used if discolored or cloudy and/or if particulate matter remains after filtration.

Pharmaceutical compositions described herein may be prepared by any method known or hereafter developed in the art of pharmacology. In some embodiments, such preparatory methods include the step of bringing active ingredient into association with one or more excipients and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient; for example, an anti-fPSA antibody and an anti-androgen therapy. The amount of the active ingredient is generally equal to a dose that would be administered to a subject and/or a convenient fraction of such a dose such as, for example, one-half or one-third of such a dose.

Relative amounts of active ingredient, pharmaceutically acceptable excipient, and/or any additional ingredients in a pharmaceutical composition in accordance with the invention may vary, depending upon the identity, size, and/or condition of the subject treated and/or depending upon the route by which the composition is to be administered. By way of example, the composition may comprise between 0.1% and 100% (w/w) active ingredient.

Pharmaceutical compositions of the present invention may additionally comprise a pharmaceutically acceptable excipient, which, as used herein, may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

Conjugates Generally

Multifunctional agents described herein comprise multiple entities, each having at least one function (e.g., a monoclonal antibody specific for an epitope in or near the catalytic cleft of fPSA conjugated to a chemotherapeutic agent). Certain embodiments of contemplated multifunctional agents comprise a targeting entity and at least one of the following entities: a detection entity, a therapeutic entity, and a diagnostic entity. In some embodiments, a multifunctional agent comprising an anti-fPSA antibody contains a targeting entity and a therapeutic entity but not a detection entity. In some embodiments, a multifunctional agent comprising an anti-fPSA antibody contains a targeting entity and a detection entity but not a therapeutic entity. In some embodiments, a multifunctional agent of the invention contains a targeting entity, a therapeutic entity and a detection entity. In some embodiments, the entities of an agent may be conjugated to one another. Conjugation of various entities to form a multifunctional agent is not limited to particular modes of conjugation. For example, two entities may be covalently conjugated directly to each other. Alternatively, two entities may be indirectly conjugated to each other, such as via a linker entity. In some embodiments, a multifunctional agent may include different types of conjugation within the agent, such that some entities of the agent are conjugated via direct conjugation while other entities of the agent are indirectly conjugated via one or more linkers. In some embodiments, a multifunctional agent of the invention comprises a single type of a linker entity. In other embodiments, a multifunctional agent of the invention comprises more than one type of linker entities. In some embodiments, a multifunctional agent includes a single type of linker entities but of varying length.

In some embodiments, there is a covalent association between or among entities contained in a multifunctional agent. As will be appreciated by one skilled in the art, the moieties may be attached to each other either directly or indirectly (e.g., through a linker, as described below).

In some embodiments, where one entity (such as a targeting entity) and a second entity of a multifunctional agent are directly covalently linked to each other, such direct covalent conjugation can be through a linkage (e.g., a linker or linking entity) such as an amide, ester, carbon-carbon, disulfide, carbamate, ether, thioether, urea, amine, or carbonate linkage. Covalent conjugation can be achieved by taking advantage of functional groups present on the first entity and/or the second entity of the multifunctional agent. Alternatively, a non-critical amino acid may be replaced by another amino acid that will introduce a useful group (such as amino, carboxy or sulfhydryl) for coupling purposes. Alternatively, an additional amino acid may be added to at least one of the entities of the multifunctional agent to introduce a useful group (such as amino, carboxy or sulfhydryl) for coupling purposes. Suitable functional groups that can be used to attach moieties together include, but are not limited to, amines, anhydrides, hydroxyl groups, carboxy groups, thiols, and the like. An activating agent, such as a carbodiimide, can be used to form a direct linkage. A wide variety of activating agents are known in the art and are suitable for conjugating one entity to a second entity.

In other embodiments, entities of a multifunctional agent embraced by the present invention are indirectly covalently linked to each other via a linker group. Such a linker group may also be referred to as a linker or a linking entity. This can be accomplished by using any number of stable bifunctional agents well known in the art, including homofunctional and heterofunctional agents (for examples of such agents, see, e.g., *Pierce Catalog and Handbook*). The use of a bifunctional linker differs from the use of an activating agent in that the former results in a linking moiety being present in the resulting conjugate (agent), whereas the latter results in a direct coupling between the two moieties involved in the reaction. The role of a bifunctional linker may be to allow reaction between two otherwise inert moieties. Alternatively or additionally, the bifunctional linker that becomes part of the reaction product may be selected such that it confers some degree of conformational flexibility to the anti-fPSA antibody (e.g., the bifunctional linker comprises a straight alkyl chain containing several atoms, for example, the straight alkyl chain contains between 2 and 10 carbon atoms). Alternatively or additionally, the bifunctional linker may be selected such that the linkage formed between a provided antibody and therapeutic agent is cleavable, e.g., hydrolysable (for examples of such linkers, see e.g. U.S. Pat. Nos. 5,773,001; 5,739,116 and 5,877,296, each of which is incorporated herein by reference in its entirety). Such linkers, for example, may be used when higher activity of certain entities, such as a targeting agent (e.g., the provided fPSA-specific antibodies) and/or of a therapeutic entity is observed after hydrolysis of the conjugate. Exemplary mechanisms by which an entity may be cleaved from a multifunctional agent include hydrolysis in the acidic pH of the lysosomes (hydrazones, acetals, and cis-aconitate-like amides), peptide cleavage by lysosomal enzymes (the capthepsins and other lysosomal enzymes), and reduction of disulfides). Another mechanism by which such an entity is cleaved from the multifunctional agent includes hydrolysis at physiological pH extra- or intracellularly. This mechanism applies when the crosslinker used to couple one entity to another entity is a biodegradable/bioerodible component, such as polydextran and the like.

For example, hydrazone-containing multifunctional agents can be made with introduced carbonyl groups that provide the desired release properties. Multifunctional agents can also be made with a linker that comprises an alkyl chain with a disulfide group at one end and a hydrazine derivative at the other end. Linkers containing functional groups other than hydrazones also have the potential to be cleaved in the acidic milieu of lysosomes. For example, multifunctional agents can be made from thiol-reactive linkers that contain a group other than a hydrazone that is cleavable intracellularly, such as esters, amides, and acetals/ketals.

Another example of class of pH sensitive linkers are the cis-aconitates, which have a carboxylic acid group juxtaposed to an amide group. The carboxylic acid accelerates amide hydrolysis in the acidic lysosomes. Linkers that achieve a similar type of hydrolysis rate acceleration with several other types of structures can also be used.

Another potential release method for conjugates of the anti-fPSA antibodies is the enzymatic hydrolysis of peptides by the lysosomal enzymes. In one example, a provided antibody is attached via an amide bond to para-aminobenzyl alcohol and then a carbamate or carbonate is made between the benzyl alcohol and the therapeutic agent. Cleavage of the peptide leads to collapse of the amino benzyl carbamate or carbonate, and release of the therapeutic agent. In another example, a phenol can be cleaved by collapse of the linker instead of the carbamate. In another variation, disulfide reduction is used to initiate the collapse of a para-mercaptobenzyl carbamate or carbonate.

Useful linkers which may be used as a linking entity of a multifunctional agent provided herein include, without limitation: polyethylene glycol, a copolymer of ethylene glycol, a polypropylene glycol, a copolymer of propylene glycol, a carboxymethylcellulose, a polyvinyl pyrrolidone, a poly-1,3-dioxolane, a poly-1,3,6-trioxane, an ethylene/maleic anhydride copolymer, a polyaminoacid, a dextran n-vinyl pyrrolidone, a poly n-vinyl pyrrolidone, a propylene glycol homopolymer, a propylene oxide polymer, an ethylene oxide polymer, a polyoxyethylated polyol, a polyvinyl alcohol, a linear or branched glycosylated chain, a polyacetal, a long chain fatty acid, a long chain hydrophobic aliphatic group.

Some embodiments of the invention utilize multifunctional agents that include at least one non-covalently associated entity. Examples of non-covalent interactions include, but are not limited to, hydrophobic interactions, electrostatic interactions, dipole interactions, van der Waals interactions, and hydrogen bonding. Irrespective of the nature of the binding, interaction, or coupling, the association between a first entity and a second entity is, in some embodiments, selective, specific and strong enough so that the second entity contained in the agent does not dissociate from the first entity before or during transport/delivery to and into the target. Thus, association among multiple entities of a multifunctional agent may be achieved using any chemical, biochemical, enzymatic, or genetic coupling known to one skilled in the art.

Therapeutic Conjugates

As described herein, anti-fPSA antibodies may comprise part of multifunctional agents with therapeutic utility related to prostate cancer. Examples of therapeutic utilities in the context of the present disclosure include, without limitation, utility associated with targeting (e.g., fPSA-specific monoclonal antibody), utility associated with therapeutic effects (e.g., cytotoxic and/or cytostatic effects, anti-proliferative effects, anti-angiogenic effects, reducing symptoms etc.), and utility associated with diagnosis, detection or labeling, etc.

A targeting entity is a molecular structure that can be contained in an agent which affects or controls the site of action by specifically interacting with, or has affinity for, a target of interest. As an example, a target may be a molecule or molecular complex present on a cell surface, e.g., certain cell types, tissues, etc. In some embodiments of the invention, the target is tumor-associated or intratumoral fPSA and the targeting entity is an anti-fPSA antibody. The anti-fPSA targeting entities disclosed herein can, by virtue of their affinity for epitopes that are only available in uncomplexed PSA, specifically or preferentially interact with fPSA. Use of targeting moieties for agents such as therapeutic agents is known in the art. In the context of the present application, primary or metastatic prostate cancer cells are the target. That is, at the molecular level, a target is a molecule or cellular constituent that is present (e.g., preferentially expressed) on a prostate cancer cell, such that it can specifically or preferentially bind to an anti-fPSA antibody upon contact. The anti-fPSA antibodies of the invention exert specificity for their target (e.g., fPSA of prostate cancer cells) and are able to localize to and bind to the target. In some embodiments, anti-fPSA antibody targeting entities localize to prostate cancers cells and retain their association over a period of time. In some embodiments, the fPSA targets are intratumoral and/or integral membrane proteins.

In some embodiments, the anti-fPSA antibodies are multifunctional agents comprising a fPSA targeting entity, which essentially consists of a fPSA-specific antibodies or antigen-binding fragment thereof, conjugated to one or more anti-cancer agents. In such embodiments, therefore, the multifunctional agents are antibody conjugates. Non-limiting embodiments of useful conjugates of anti-fPSA antibodies that may be used in the diagnosis or assessment of, treatment of and the manufacture of medicaments for prostate cancer are provided below.

In some embodiments, anti-fPSA antibodies are conjugated to a nucleic acid molecule that is useful as a therapeutic (e.g., anti-cancer) agent. A variety of chemical types and structural forms of nucleic acid can be suitable for such strategies. These include, by way of non-limiting example, DNA, including single-stranded (ssDNA) and double-stranded (dsDNA); RNA, including, but not limited to ssRNA, dsRNA, tRNA, mRNA, rRNA, enzymatic RNA;

RNA:DNA hybrids, triplexed DNA (e.g., dsDNA in association with a short oligonucleotide), and the like.

In some embodiments, the nucleic acid agent is between about 5 and 2000 nucleotides long. In some embodiments, the nucleic acid agent is at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides long. In some embodiments, the nucleic acid agent is less than about 2000, 1900, 1800, 1700, 1600, 1500, 1400, 1300, 1200, 1100, 1000, 900, 800, 700, 600, 500, 450, 400, 350, 300, 250, 200, 150, 100, 50, 45, 40, 35, 30, 25, 20 or fewer nucleotides long.

In some embodiments, the nucleic acid agent comprises a promoter and/or other sequences that regulate transcription. Such embodiments may comprise, for example, nucleotides sequences corresponding to androgen response elements (e.g., PSA androgen response element AGCACT TGC TGTTCT (SEQ ID NO: 1)), which can thereby function as a decoy to bind activated ARs. In some embodiments, the nucleic acid agent comprises an origin of replication and/or other sequences that regulate replication. In some embodiments, the nucleic acid agent does not include a promoter and/or an origin of replication.

Nucleic acid anti-cancer agents suitable for use in the practice of the present invention include those agents that target genes associated with tumorigenesis and cell growth or cell transformation (e.g., proto-oncogenes, which code for proteins that stimulate cell division), angiogenic/anti-angiogenic genes, tumor suppressor genes (which code for proteins that suppress cell division), genes encoding proteins associated with tumor growth and/or tumor migration, and suicide genes (which induce apoptosis or other forms of cell death), especially suicide genes that are most active in rapidly dividing cells.

Examples of genes associated with tumorigenesis and/or cell transformation include androgen receptor genes, MLL fusion genes, BCR-ABL, TEL-AML1, EWS-FLI1, TLS-FUS, PAX3-FKHR, Bcl-2, AML1-ETO, AML1-MTG8, Ras, Fos PDGF, RET, APC, NF-1, Rb, p53, MDM2 and the like; overexpressed genes such as multidrug resistance genes; cyclins; beta-Catenin; telomerase genes; c-myc, n-myc, Bcl-2, Erb-B1 and Erb-B2; and mutated genes such as Ras, Mos, Raf, and Met. Examples of tumor suppressor genes include, but are not limited to, p53, p21, RB1, WT1, NF1, VHL, APC, DAP kinase, p16, ARF, Neurofibromin, and PTEN. Examples of genes that can be targeted by nucleic acid agents useful in anti-cancer therapy include genes encoding proteins associated with tumor migration such as integrins, selectins, and metalloproteinases; anti-angiogenic genes encoding proteins that promote formation of new vessels such as Vascular Endothelial Growth Factor (VEGF) or VEGFr; anti-angiogenic genes encoding proteins that inhibit neovascularization such as endostatin, angiostatin, and VEGF-R2; and genes encoding proteins such as interleukins, interferon, fibroblast growth factor (α-FGF and β-FGF), insulin-like growth factor (e.g., IGF-1 and IGF-2), Platelet-derived growth factor (PDGF), tumor necrosis factor (TNF), Transforming Growth Factor (e.g., TGF-α and TGF-β, Epidermal growth factor (EGF), Keratinocyte Growth Factor (KGF), stem cell factor and its receptor c-Kit (SCF/c-Kit) ligand, CD40L/CD40, VLA-4 VCAM-1, ICAM-1/LFA-1, hyalurin/CD44, and the like.

Nucleic acid agents suitable for conjugation with anti-fPSA antibodies may have any of a variety of uses including, for example, use as anti-cancer or other therapeutic agents, probes, primers, etc. Nucleic acid agents may have enzymatic activity (e.g., ribozyme activity), gene expression inhibitory activity (e.g., as antisense or siRNA agents, etc), and/or other activities. Nucleic acids agents may be active themselves or may be vectors that deliver active nucleic acid agents (e.g., through replication and/or transcription of a delivered nucleic acid). For purposes of the present specification, such vector nucleic acids are considered "therapeutic agents" if they encode or otherwise deliver a therapeutically active agent, even if they do not themselves have therapeutic activity.

In certain embodiments, conjugates of anti-fPSA antibodies comprise a nucleic acid therapeutic agent that comprises or encodes an antisense compound. The terms "antisense compound or agent," "antisense oligomer," "antisense oligonucleotide," and "antisense oligonucleotide analog" are used herein interchangeably, and refer to a sequence of nucleotide bases and a subunit-to-subunit backbone that allows the antisense compound to hybridize to a target sequence in an RNA by Watson-Crick base pairing to form an RNA oligomer heteroduplex within the target sequence. The oligomer may have exact sequence complementarity within the target sequence or near complementarity. Such antisense oligomers may block or inhibit translation of the mRNA containing the target sequence, or inhibit gene transcription. Antisense oligomers may bind to double-stranded or single-stranded sequences.

Examples of antisense oligonucleotides suitable for use in the practice of the present invention include, for example, those mentioned in the following reviews: R. A Stahel et al., *Lung Cancer*, 2003, 41: S81-S88; K. F. Pirollo et al., *Pharmacol. Ther.*, 2003, 99: 55-77; A. C. Stephens and R. P. Rivers, *Curr. Opin. Mol. Ther.*, 2003, 5: 118-122; N. M. Dean and C. F. Bennett, *Oncogene*, 2003, 22: 9087-9096; N. Schiavone et al., *Curr. Pharm. Des.*, 2004, 10: 769-784; L. Vidal et al., *Eur. J Cancer*, 2005, 41: 2812-2818; T. Aboul-Fadl, *Curr. Med. Chem.*, 2005, 12: 2193-2214; M. E. Gleave and B. P. Monia, *Nat. Rev. Cancer*, 2005, 5: 468-479; Y. S. Cho-Chung, *Curr. Pharm. Des.*, 2005, 11: 2811-2823; E. Rayburn et al., *Lett. Drug Design & Discov.*, 2005, 2: 1-18; E. R. Rayburn et al., *Expert Opin. Emerg. Drugs*, 2006, 11: 337-352; I. Tamm and M. Wagner, *Mol. Biotechnol.*, 2006, 33: 221-238 (each of which is incorporated herein by reference in its entirety).

Examples of suitable antisense oligonucleotides include EZN-4176, a nucleic acid-based antisense oligonucleotide that downregulates AR mRNA (Zhang, Y. et al., *Mol. Cancer Therapeutics*, 2011, 10:2309); AR oligodeoxynucleotides that inhibit the cell growth of LNCaP protate tumor cells (Eder, I. E. et al., *Nature*, 2000, 7(7): 997-1008); and oblimersen sodium (also known as G31239, developed by Genta, Inc., Berkeley Heights, N.J.), a phosphorothioate oligomer targeted towards the initiation codon region of the bcl-2 mRNA. Bcl-2 is a potent inhibitor of apoptosis and is overexpressed in many cancer including follicular lymphomas, breast cancer, colon cancer, prostate cancer, and intermediate/high-grade lymphomas (C. A. Stein et al., *Semin. Oncol.*, 2005, 32: 563-573; S. R. Frankel, *Semin. Oncol.*, 2003, 30: 300-304). Other suitable antisense oligonucleotides include GEM-231 (HYB0165, Hybridon, Inc., Cambridge, Mass.), which is a mixed backbone oligonucleotide directed against cAMP-dependent protein kinase A (PKA) (S. Goel et al., *Clin. Cancer Res.*, 2003, 9: 4069-4076); Affinitak (ISIS 3521 or aprinocarsen, ISIS pharmaceuticals, Inc., Carlsbad, Calif.), an antisense inhibitor of PKCalpha; OGX-011 (Isis 112989, Isis Pharmaceuticals, Inc.), a 2'-methoxyethyl modified antisense oligonucleotide against clusterin, a glycoprotein implicated in the regulation of the cell cycle, tissue remodeling, lipid transport, and cell death and which is overexpressed in cancers of breast, prostate and colon; ISIS 5132 (Isis 112989, Isis Pharmaceuticals, Inc.), a phosphorothioate oligonucleotide complementary to a sequence of the 3'-unstranslated region of the c-raf-1 mRNA (S. P. Henry et al., *Anticancer Drug Des.*, 1997, 12: 409-420; B. P. Monia et al., Proc. Natl. Acad. Sci. USA, 1996, 93: 15481-15484; C. M. Rudin et al., *Clin. Cancer Res.*, 2001, 7: 1214-1220); ISIS 2503 (Isis Pharmaceuticals, Inc.), a phosphorothioate oligonucleotide antisense inhibitor of human H-ras mRNA expression (J. Kurreck, *Eur. J. Biochem.*, 2003, 270: 1628-1644); oligonucleotides targeting the X-linked inhibitor of apoptosis protein (XIAP), which blocks a substantial portion of the apoptosis pathway, such as GEM 640 (AEG 35156, Aegera Therapeutics Inc. and Hybridon, Inc.) or targeting survivin, an inhibitor of apoptosis protein (IAP), such as ISIS 23722 (Isis Pharmaceuticals, Inc.), a 2'-O-methoxyethyl chimeric oligonucleotide; MG98, which targets DNA methyl transferase; and GTI-2040 (Lorus Therapeutics, Inc. Toronto, Canada), a 20-mer oligonucleotide that is complementary to a coding region in the mRNA of the R2 small subunit component of human ribonucleotide reductase.

Other suitable antisense oligonucleotides include antisense oligonucleotides that are being developed against Her-2/neu, c-Myb, c-Myc, and c-Raf (see, for example, A. Biroccio et al., *Oncogene*, 2003, 22: 6579-6588; Y. Lee et al., *Cancer Res.*, 2003, 63: 2802-2811; B. Lu et al., *Cancer Res.*, 2004, 64: 2840-2845; K. F. Pirollo et al., *Pharmacol. Ther.*, 2003, 99: 55-77; and A. Rait et al., *Ann. N.Y. Acad. Sci.*, 2003, 1002: 78-89).

In certain embodiments, conjugates of anti-fPSA antibodies comprise a nucleic acid anti-cancer agent that comprises or encodes an interfering RNA molecule. The terms "interfering RNA" and "interfering RNA molecule" are used herein interchangeably, and refer to an RNA molecule that can inhibit or downregulate gene expression or silence a gene in a sequence-specific manner, for example by mediating RNA interference (RNAi). RNA interference (RNAi) is an evolutionarily conserved, sequence-specific mechanism triggered by double-stranded RNA (dsRNA) that induces degradation of complementary target single-stranded mRNA and "silencing" of the corresponding translated sequences (McManus and Sharp, 2002, *Nature Rev. Genet.*, 2002, 3: 737). RNAi functions by enzymatic cleavage of longer dsRNA strands into biologically active "short-interfering RNA" (siRNA) sequences of about 21-23 nucleotides in length (Elbashir et al., *Genes Dev.*, 2001, 15: 188). RNA interference has emerged as a promising approach for therapy of cancer.

An interfering RNA suitable for use in the practice of the present invention can be provided in any of several forms. For example, an interfering RNA can be provided as one or more of an isolated short interfering RNA (siRNA), double-stranded RNA (dsRNA), micro-RNA (miRNA), or short hairpin RNA (shRNA).

Examples of interfering RNA molecules suitable for use in the present invention include, for example, the iRNAs cited in the following reviews: O. Milhavet et al., *Pharmacol. Rev.*, 2003, 55: 629-648; F. Bi et al., *Curr. Gene. Ther.*, 2003, 3: 411-417; P. Y. Lu et al., *Curr. Opin. Mol. Ther.*, 2003, 5: 225-234; I. Friedrich et al., *Semin. Cancer Biol.*, 2004, 14: 223-230; M. Izquierdo, *Cancer Gene Ther.*, 2005, 12: 217-227; P. Y. Lu et al., *Adv. Genet.*, 2005, 54: 117-142; G. R. Devi, *Cancer Gene Ther.*, 2006, 13: 819-829; M. A. Behlke, *Mol. Ther.*, 2006, 13: 644-670; and L. N. Putral et al., *Drug News Perspect.*, 2006, 19: 317-324 (the contents of each of which are incorporated herein by reference in their entirety).

Other examples of suitable interfering RNA molecules include, but are not limited to, p53 interfering RNAs (e.g., T. R. Brummelkamp et al., *Science*, 2002, 296: 550-553; M. T. Hemman et al., *Nat. Genet.*, 2003, 33: 396-400); interfering RNAs that target oncogenes, such as Raf-1 (T. F. Lou et al., *Oligonucleotides*, 2003, 13: 313-324), K-Ras (T. R. Brummelkamp et al., *Cancer Cell*, 2002, 2: 243-247), and erbB-2 (G. Yang et al., *J Biol. Chem.*, 2004, 279: 4339-4345).

In certain embodiments, conjugates of anti-fPSA antibodies comprise a nucleic acid therapeutic agent that is a ribozyme. As used herein, the term "ribozyme" refers to a catalytic RNA molecule that can cleave other RNA molecules in a target-specific marmer Ribozymes can be used to downregulate the expression of any undesirable products of genes of interest. Examples of ribozymes that can be used in the practice of the present invention include, but are not limited to, those specific for androgen receptor mRNA.

In certain embodiments, entities or moieties within conjugates of the anti-fPSA antibodies comprise a photosensitizer used in photodynamic therapy (PDT). In PDT, local or systemic administration of a photosensitizer to a patient is followed by irradiation with light that is absorbed by the photosensitizer in the tissue or organ to be treated. Light absorption by the photosensitizer generates reactive species (e.g., radicals) that are detrimental to cells. For maximal efficacy, a photosensitizer typically is in a form suitable for administration, and also in a form that can readily undergo cellular internalization at the target site, often with some degree of selectivity over normal tissues.

Conjugates of anti-fPSA antibodies associated with a photosensitizer can be used as new delivery systems in PDT. In addition to reducing photosensitizer aggregation, delivery of photosensitizers according to the present invention exhibits other advantages such as increased specificity for target tissues/organ and cellular internalization of the photosensitizer.

Photosensitizers suitable for use in the present invention include any of a variety of synthetic and naturally occurring molecules that have photosensitizing properties useful in PDT. In certain embodiments, the absorption spectrum of the photosensitizer is in the visible range, typically between 350 nm and 1200 nm, preferably between 400 nm and 900 nm, e.g., between 600 nm and 900 nm. Suitable photosensitizers that can be coupled to toxins according to the present invention include, but are not limited to, porphyrins and porphyrin derivatives (e.g., chlorins, bacteriochlorins, isobacteriochlorins, phthalocyanines, and naphthalocyanines); metalloporphyrins, metallophthalocyanines, angelicins, chalcogenapyrrillium dyes, chlorophylls, coumarins, flavins and related compounds such as alloxazine and riboflavin, fullerenes, pheophorbides, pyropheophorbides, cyanines (e.g., merocyanine 540), pheophytins, sapphyrins, texaphyrins, purpurins, porphycenes, phenothiaziniums, methylene blue derivatives, naphthalimides, nile blue derivatives, quinones, perylenequinones (e.g., hypericins, hypocrellins, and cercosporins), psoralens, quinones, retinoids, rhodamines, thiophenes, verdins, xanthene dyes (e.g., eosins, erythrosins, rose bengals), dimeric and oligomeric forms of porphyrins, and prodrugs such as 5-aminolevulinic acid (R. W. Redmond and J. N. Gamlin, *Photochem. Photobiol.*, 1999, 70: 391-475).

Exemplary photosensitizers suitable for use in the present invention include those described in U.S. Pat. Nos. 5,171, 741; 5,171,749; 5,173,504; 5,308,608; 5,405,957; 5,512,675; 5,726,304; 5,831,088; 5,929,105; and 5,880,145 (the contents of each of which are incorporated herein by reference in their entirety).

In certain embodiments, conjugates of anti-fPSA specific antibodies comprise a radiosensitizer. As used herein, the term "radiosensitizer" refers to a molecule, compound or agent that makes tumor cells more sensitive to radiation therapy. Administration of a radiosensitizer to a patient receiving radiation therapy generally results in enhancement of the effects of radiation therapy. The advantage of coupling a radiosensitizer to a targeting entity (e.g., anti-fPSA antibodies capable of targeting intratumoral fPSA) is that the radiosensitize effects only on target cells. For ease of use, a radiosensitizer should also be able to find target cells even if it is administered systemically. However, currently available radiosensitizers are typically not selective for tumors, and they are distributed by diffusion in a mammalian body. fPSA antibody conjugates of the present invention can be used as a new delivery system for radiosensitizers.

A variety of radiosensitizers are known in the art. Examples of radiosensitizers suitable for use in the present invention include, but are not limited to, paclitaxel (TAXOL®), carboplatin, cisplatin, and oxaliplatin (Amorino et al., *Radiat. Oncol. Investig.,* 1999, 7: 343-352; Choy, *Oncology,* 1999, 13: 22-38; Safran et al., *Cancer Invest.,* 2001, 19: 1-7; Dionet et al., *Anticancer Res.,* 2002, 22: 721-725; Cividalli et al., *Radiat. Oncol. Biol. Phys.,* 2002, 52: 1092-1098); gemcitabine (Gemzar®) (Choy, *Oncology,* 2000, 14: 7-14; Mornex and Girard, *Annals of Oncology,* 2006, 17: 1743-1747); etanidazole (Nitrolmidazole®) (Inanami et al., *Int. J. Radiat. Biol.,* 2002, 78: 267-274); misonidazole (Tamulevicius et al., *Br. J. Radiology,* 1981, 54: 318-324; Palcic et al., *Radiat. Res.,* 1984, 100: 340-347), tirapazamine (Masunaga et al., *Br. J. Radiol.,* 2006, 79: 991-998; Rischin et al., *J. Clin. Oncol.,* 2001, 19: 535-542; Shulman et al., *Int. J. Radiat. Oncol. Biol. Phys.,* 1999, 44: 349-353); and nucleic acid base derivatives, e.g., halogenated purines or pyrimidines, such as 5-fluorodeoxyuridine (Buchholz et al., *Int. J. Radiat. Oncol. Biol. Phys.,* 1995, 32: 1053-1058).

In certain embodiments, conjugates of anti-fPSA antibodies comprise a radioisotope. Examples of suitable radioisotopes include any α-, β- or γ-emitter, which, when localized at a tumor site, results in cell destruction (S. E. Order, "Analysis, Results, and Future Prospective of the Therapeutic Use of Radiolabeled Antibody in Cancer Therapy", Monoclonal Antibodies for Cancer Detection and Therapy, R. W. Baldwin et al. (Eds.), Academic Press, 1985). Examples of such radioisotopes include, but are not limited to, iodine-131 ($^{131}$I), iodine-125 ($^{125}$I), bismuth-212 ($^{212}$Bi), bismuth-213 ($^{213}$Bi), astatine-211 ($^{211}$At), rhenium-186 ($^{186}$Re), rhenium-188 ($^{188}$Re), phosphorus-32 ($^{32}$P), yttrium-90 ($^{90}$Y), samarium-153 ($^{153}$Sm), and lutetium-177 ($^{177}$Lu).

In certain embodiments, conjugates of anti-fPSA antibodies comprise a superantigen or biologically active portion thereof. Superantigens constitute a group of bacterial and viral proteins that are extremely efficient in activating a large fraction of the T-cell population. Superantigens bind directly to the major histocompatibility complex (MHC) without being processed. In fact, superantigens bind unprocessed outside the antigenbinding groove on the MHC class II molecules, thereby avoiding most of the polymorphism in the conventional peptide-binding site.

A superantigen-based tumor therapeutic approach has been developed for the treatment of solid tumors. In this approach, a targeting moiety (e.g., an anti-fPSA antibody or antigen-binding fragment thereof) is conjugated to a superantigen, providing a targeted superantigen. If the antibody, or antibody fragment, recognizes a tumor-associated antigen, the targeted superantigen, bound to tumors cells, can trigger superantigen-activated cytotoxic T-cells to kill the tumor cells directly by superantigen-dependent cell mediated cytotoxicity. (See, e.g., Søgaard et al., (1996) "Antibody-targeted superantigens in cancer immunotherapy," *Immunotechnology,* 2(3): 151-162, the entire contents of which are herein incorporated by reference.)

Examples of superantigens for use in embodiments of the invention include, fusion proteins with wild-type staphylococcal enterotoxin A (SEA) (Giantonio et al., *J. Clin. Oncol.,* 1997, 15: 1994-2007; Alpaugh et al., *Clin. Cancer Res.,* 1998, 4: 1903-1914; Cheng et al., *J. Clin. Oncol.,* 2004, 22: 602-609; the entire contents of each of which are herein incorporated by reference); staphylococcal superantigens of the enterotoxin gene cluster (egc) (Terman et al., *Clin. Chest Med.,* 2006, 27: 321-324, the entire contents of which are herein incorporated by reference), and staphylococcal enterotoxin B (SEB) (Perabo et al., *Int. J Cancer,* 2005, 115: 591-598, the entire contents of which are herein incorporated by reference). A superantigen, or a biologically active portion thereof, can be associated to anti-fPSA antibodies to form a conjugate comprising the antibody and a superantigen. Additional examples of superantigens suitable for use in the present invention include, but are not limited to, staphylococcal enterotoxin E (SEE)), *Streptococcus pyogenes* exotoxin (SPE), *Staphylococcus aureus* toxic shock-syndrome toxin (TSST-1), streptococcal mitogenic exotoxin (SME), and streptococcal superantigen (SSA).

In certain embodiments, conjugates of the anti-fPSA antibodies may be used in directed enzyme prodrug therapy. In a directed enzyme prodrug therapy approach, a directed/targeted enzyme and a prodrug are administered to a subject, wherein the targeted enzyme is specifically localized to a portion of the subject's body where it converts the prodrug into an active drug. The prodrug can be converted to an active drug in one step (by the targeted enzyme) or in more than one step. For example, the prodrug can be converted to a precursor of an active drug by the targeted enzyme. The precursor can then be converted into the active drug by, for example, the catalytic activity of one or more additional targeted enzymes, one or more non-targeted enzymes administered to the subject, one or more enzymes naturally present in the subject or at the target site in the subject (e.g., a protease, phosphatase, kinase or polymerase), by an agent that is administered to the subject, and/or by a chemical process that is not enzymatically catalyzed (e.g., oxidation, hydrolysis, isomerization, epimerization, etc.).

Some embodiments of the invention utilize antibody-directed enzyme prodrug therapy (ADEPT), wherein an anti-fPSA antibody is linked to an enzyme and injected in a subject, resulting in selective binding of the enzyme to tumor-associated or metstatic fPSA. As discussed above, the anti-fPSA antibodies disclosed herein (e.g., 5A10) can sufficiently discriminate between intratumoral fPSA and serum PSA. Subsequently, a prodrug is administered to the subject. The prodrug is converted to its active form by the enzyme only within or nearby the prostate cancer cells. Selectivity is achieved by the specificity of the anti-fPSA antibody and by delaying prodrug administration until there is a large differential between prostate cancer and normal tissue enzyme levels. Prostate cancer cells may also be targeted with the genes encoding for prodrug activating enzymes. This approach has been called virus-directed enzyme prodrug therapy (VDEPT) or more generally GDEPT (gene-directed enzyme prodrug therapy, and has shown good results in laboratory systems. Other versions of directed enzyme prodrug therapy include PDEPT (polymer-directed enzyme prodrug therapy), LEAPT (lectin-directed enzyme-activated prodrug therapy), and CDEPT (clostridial-directed enzyme prodrug therapy).

Nonlimiting examples of enzyme/prodrug/active drug combinations suitable for use in the present invention are described, for example, in Bagshawe et al., *Current Opinions in Immunology*, 1999, 11: 579-583; Wilman, "Prodrugs in Cancer Therapy", *Biochemical Society Transactions*, 14: 375-382, 615th Meeting, Belfast, 1986; Stella et al., "Prodrugs: A Chemical Approach To Targeted Drug Delivery", in "Directed Drug Delivery", Borchardt et al., (Eds), pp. 247-267 (Humana Press, 1985). Nonlimiting examples of enzyme/prodrug/active anti-cancer drug combinations are described, for example, in Rooseboom et al., *Pharmacol. Reviews*, 2004, 56: 53-102.

Examples of prodrug activating enzymes include, but are not limited to, nitroreductase, cytochrome P450, purine-nucleoside phosphorylase, thymidine kinase, alkaline phosphatase, β-glucuronidase, carboxypeptidase, penicillin amidase, β-lactamase, cytosine deaminase, and methionine γ-lyase.

Examples of anti-cancer drugs that can be formed in vivo by activation of a prodrug by a prodrug activating enzyme include, but are not limited to, 5-(aziridin-1-yl)-4-hydroxyl-amino-2-nitro-benzamide, isophosphoramide mustard, phosphoramide mustard, 2-fluoroadenine, 6-methylpurine, ganciclovir-triphosphate nucleotide, etoposide, mitomycin C, p-[N,N-bis(2-chloroethyl)amino]phenol (POM), doxorubicin, oxazolidinone, 9-aminocamptothecin, mustard, methotrexate, benzoic acid mustard, adriamycin, daunomycin, carminomycin, bleomycins, esperamicins, melphalan, palytoxin, 4-desacetylvinblastine-3-carboxylic acid hydrazide, phenylenediamine mustard, 4'-carboxyphthalato(1,2-cyclohexane-diamine) platinum, taxol, 5-fluorouracil, methylselenol, and carbonothionic difluoride.

In certain embodiments, a therapeutic (e.g., anti-cancer) agent comprises a conjugate of one or more anti-fPSA antibodies and an anti-angiogenic agent. Antiangiogenic agents suitable for use in the present invention include any molecule, compound, or factor that blocks, inhibits, slows down, or reduces the process of angiogenesis, or the process by which new blood vessels form by developing from preexisting vessels. Such a molecule, compound, or factor can block angiogenesis by blocking, inhibiting, slowing down, or reducing any of the steps involved in angiogenesis, including (but not limited to) steps of (1) dissolution of the membrane of the originating vessel, (2) migration and proliferation of endothelial cells, and (3) formation of new vasculature by migrating cells.

Examples of anti-angiogenic agents include, but are not limited to, bevacizumab (AVASTIN®), celecoxib (CELEBREX®), endostatin, thalidomide, EMD121974 (Cilengitide), TNP-470, squalamine, combretastatin A4, interferon-α, anti-VEGF antibody, SU5416, SU6668, PTK787/2K 22584, Marimistal, AG3340, COL-3, Neovastat, and BMS-275291.

In some embodiments, a therapeutic agent comprises a conjugate of one or more anti-fPSA antibodies and an anti-androgen therapy, such as an androgen receptor ("AR") antagonist. AR antagonists for use in these and other embodiments of the invention include small molecule antagonists (e.g., RU58642, LG120907, LG105, RD162, MDV3100, BMS-641988, CH5137291, atraric acid, N-butylbenzenesulfonamide), steroidal compounds (e.g., cyproterone acetate), non-steroidal compounds (e.g., hydroxyflutamide, bicalutamide, nilutamide), and peptide antagonists. Other anti-androgen therapies for use in embodiments of the invention include TAK700, ARN-509, cabozantimib, ipilimumab, custirsen, BPX-101, alpharadin, denosumab and Protsvac-VF.

Additional prostate cancer therapeutic agenst for use in particular embodiments of the invention include Radium-223 chloride, cabozantinib, anti-OX40 antibodies, and bicalutamide (Casodex).

Administration fPSA monoclonal antibodies and/or antibody polypeptides in accordance with the invention and pharmaceutical compositions of the present invention may be administered according to any appropriate route and regimen. In some embodiments, a route or regimen is one that has been correlated with a positive therapeutic benefit.

In some embodiments, the exact amount administered may vary from subject to subject, depending on one or more factors as is well known in the medical arts. Such factors may include, for example, one or more of species, age, general condition of the subject, the particular composition to be administered, its mode of administration, its mode of activity, the severity of the prostate cancer; the activity of the specific fPSA antibody employed; the specific pharmaceutical composition administered; the half-life of the composition after administration; the age, body weight, general health, sex, and diet of the subject; the time of administration, route of administration, and rate of excretion of the specific compound employed; the duration of the treatment; drugs used in combination or coincidental with the specific compound employed and the like. Pharmaceutical compositions may be formulated in dosage unit form for ease of administration and uniformity of dosage. It will be understood, however, that the total daily usage of the compositions of the present invention will be decided by an attending physician within the scope of sound medical judgment.

Compositions of the present invention may be administered by any route, as will be appreciated by those skilled in the art. In some embodiments, compositions of the present invention are administered by oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical (e.g., by powders, ointments, creams, gels, lotions, and/or drops), mucosal, intranasal, buccal, enteral, vitreal, sublingual; by intratracheal instillation, bronchial instillation, and/or inhalation; as an oral spray, nasal spray, and/or aerosol, and/or through a portal vein catheter.

In specific embodiments, fPSA antibodies in accordance with the present invention and/or pharmaceutical compositions thereof may be administered intravenously, for example, by intravenous infusion. In specific embodiments, fPSA antibodies in accordance with the present invention and/or pharmaceutical compositions thereof may be administered by intramuscular injection. In specific embodiments, fPSA antibodies in accordance with the present invention and/or pharmaceutical compositions thereof may be administered by intraprostate injection. In specific embodiments, fPSA antibodies in accordance with the present invention and/or pharmaceutical compositions thereof may be administered by subcutaneous injection. In specific embodiments, fPSA antibodies in accordance with the present invention and/or pharmaceutical compositions thereof may be administered via portal vein catheter. However, the invention encompasses the delivery of fPSA antibodies in accordance with the present invention and/or pharmaceutical compositions thereof by any appropriate route taking into consideration likely advances in the sciences of drug delivery.

In certain embodiments, fPSA antibodies in accordance with the present invention and/or pharmaceutical compositions thereof may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg of subject body weight per day to obtain the desired therapeutic effect. The desired dosage may be delivered more than three times per day, three times per day, two times per day, once per day, every other day, every third day, every week, every two weeks, every three weeks, every four weeks, every two months, every six months, or every twelve months. In certain embodiments, the desired dosage may be delivered using multiple administrations (e.g., two, three, four, five, six, seven, eight, nine, ten, eleven, twelve, thirteen, fourteen, or more administrations).

Prophylactic Applications

In some embodiments, fPSA antibodies in accordance with the invention may be utilized for prophylactic applications. In some embodiments, prophylactic applications involve systems and methods for preventing, inhibiting progression of, and/or delaying the onset of prostate cancer, and/or any other fPSA-associated condition in individuals susceptible to and/or displaying symptoms of prostate cancer.

Combination Therapy

It will be appreciated that fPSA antibodies and therapeutically active conjugates thereof in accordance with the present invention and/or pharmaceutical compositions thereof can be employed in combination therapies to aid in diagnosis and/or treatment. "In combination" is not intended to imply that the agents must be administered at the same time and/or formulated for delivery together, although these methods of delivery are within the scope of the invention. Compositions can be administered concurrently with, prior to, or subsequent to, one or more other desired therapeutics or medical procedures. In will be appreciated that therapeutically active agents utilized in combination may be administered together in a single composition or administered separately in different compositions. In general, each agent will be administered at a dose and/or on a time schedule determined for that agent.

In particular embodiments, the fPSA-specific antibodies disclosed herein are administered before, after, or in conjunction with an anti-cancer agent or anti-androgen therapy. Anti-androgen therapies include surgery (e.g., castration), chemotherapy, radiation therapy and androgen receptor ("AR") antagonists. AR antagonists for use in these and other embodiments of the invention include small molecule antagonists (e.g., RU58642, LG120907, LG105, RD162, MDV3100, BMS-641988, CH5137291, atraric acid, N-butylbenzenesulfonamide), steroidal compounds (e.g., cyproterone acetate), non-steroidal compounds (e.g., hydroxyflutamide, bicalutamide, nilutamide), and peptide antagonists. Other anti-androgen therapies for use in embodiments of the invention include TAK700, ARN-509 (abiraterone), cabozantimib, ipilimumab, custirsen, BPX-101, alpharadin, denosumab and Protsvac-VF. Additional prostate cancer therapeutic agents for use in particular embodiments of the invention include Radium-223 chloride, cabozantinib, anti-OX40 antibodies, and bicalutamide (Casodex).

The particular combination of therapies (e.g., therapeutics or procedures) to employ in a combination regimen will take into account compatibility of the desired therapeutics and/or procedures and the desired therapeutic effect to be achieved. It will also be appreciated that pharmaceutical compositions of the anti-fPSA antibodies disclosed herein can be employed in combination therapies (e.g., combination chemotherapeutic therapies), that is, the pharmaceutical compositions can be administered concurrently with, prior to, or subsequent to, one or more other desired therapeutic and/or chemotherapeutic procedures.

anti-fPSA antibodies, or a pharmaceutically acceptable composition thereof, may be administered in combination with chemotherapeutic agents to treat primary or metastatic prostate cancer. In some embodiments, an active ingredient is a chemotherapeutic agent, such as, but not limited to, Adriamycin, dexamethasone, vincristine, cyclophosphamide, fluorouracil, topotecan, taxol, interferons, platinum derivatives, taxane (e.g., paclitaxel), *vinca* alkaloids (e.g., vinblastine), anthracyclines (e.g., doxorubicin), epipodophyllotoxins (e.g., etoposide), cisplatin, methotrexate, actinomycin D, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, metronidazole, imatinib, Gleevec™, sunitinib and Sutent® and combinations thereof.

In certain embodiments, anti-fPSA antibodies, conjugates thereof, or a pharmaceutically acceptable composition thereof, are administered in combination with an antiproliferative or chemotherapeutic agent selected from any one or more of Abarelix, aldesleukin, Aldesleukin, Alemtuzumab, Alitretinoin, Allopurinol, Altretamine, Amifostine, Anastrozole, Arsenic trioxide, Asparaginase, Azacitidine, BCG Live, Bevacuzimab, Avastin, Fluorouracil, Bexarotene, Bleomycin, Bortezomib, Busulfan, Calusterone, Capecitabine, Camptothecin, Carboplatin, Carmustine, Celecoxib, Cetuximab, Chlorambucil, Cisplatin, Cladribine, Clofarabine, Cyclophosphamide, Cytarabine, Dactinomycin, Darbepoetin alfa, Daunorubicin, Denileukin, Dexrazoxane, Docetaxel, Doxorubicin (neutral), Doxorubicin hydrochloride, Dromostanolone Propionate, Epirubicin, Epoetin alfa, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin Acetate, Hydroxyurea, Ibritumomab, Idarubicin, Ifosfamide, Imatinib Mesylate, Interferon Alfa-2a, Interferon Alfa-2b, Irinotecan, Lenalidomide, Letrozole, Leucovorin, Leuprolide Acetate, Levamisole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard, Valrubicin, Vinblastine, Vincristine, Vinorelbine, Zoledronate, or Zoledronic acid.

The particular combination of therapies (e.g., Doxorubicin, ARN-509 and therapeutic antibodies to fPSA, etc.) to employ in a combination regimen will generally take into account compatibility of the desired therapeutics and/or procedures and the desired therapeutic effect to be achieved. It will also be appreciated that the therapies and/or chemotherapeutics employed may achieve a desired effect for the same disorder (for example, an inventive antigen may be administered concurrently with another chemotherapeutic), or they may achieve different effects. It will be appreciated that the therapies employed may achieve a desired effect for the same purpose (for example, fPSA-specific antibodies useful for treating, preventing, and/or delaying the onset of prostate cancer may be administered concurrently with another agent useful for treating, preventing, and/or delaying the onset of prostate cancer), or they may achieve different effects (e.g., control of any adverse effects). The invention encompasses the delivery of pharmaceutical compositions in combination with agents that may improve their bioavailability, reduce and/or modify their metabolism, inhibit their excretion, and/or modify their distribution within the body.

In particular embodiment anti-fPSA antibodies are administered in combination with or conjugated to ARN-509 (abiraterone) and/or Doxorubicin. Additional prostate cancer therapeutic agenst for use in such embodiments of the invention include Radium-223 chloride, cabozantinib, anti-OX40 antibodies, and bicalutamide (Casodex).

In some embodiments, agents utilized in combination with be utilized at levels that do not exceed the levels at which they are utilized individually. In some embodiments, the levels utilized in combination will be lower than those utilized individually.

In some embodiments, combination therapy may involve administrations of a plurality of antibodies directed to a single epitope (e.g., a single conformational epitope). In some embodiments, combination therapy can comprise a plurality of antibodies that recognize distinct epitopes.

Kits

The invention provides a variety of kits for conveniently and/or effectively carrying out methods in accordance with the present invention. Kits typically comprise one or more fPSA-specific antibodies or antibody polypeptides in accordance with the invention (e.g., 5A10). In some embodiments, kits comprise a collection of different fPSA-specific antibodies to be used for different purposes (e.g., diagnostics, treatment, and/or prophylaxis). Typically kits will comprise sufficient amounts of fPSA-specific antibodies to allow a user to perform multiple administrations to a subject(s) and/or to perform multiple experiments. In some embodiments, kits are supplied with or include one or more fPSA-specific antibodies that have been specified by the purchaser.

In certain embodiments, kits for use in accordance with the present invention may include one or more reference samples; instructions (e.g., for processing samples, for performing tests, for interpreting results, for solubilizing fPSA-specific antibodies, for storage of fPSA-specific antibodies, etc.); buffers; and/or other reagents necessary for performing tests. In certain embodiments kits can comprise panels of antibodies. Other components of kits may include cells, cell culture media, tissue, and/or tissue culture media.

In some embodiments, kits include a number of unit dosages of a pharmaceutical composition comprising fPSA-specific antibodies. A memory aid may be provided, for example in the form of numbers, letters, and/or other markings or with a calendar insert, designating the days/times in the treatment schedule in which dosages can be administered. Placebo dosages, and/or calcium dietary supplements, either in a form similar to or distinct from the dosages of the pharmaceutical compositions, may be included to provide a kit in which a dosage is taken every day.

Kits may comprise one or more vessels or containers so that certain of the individual components or reagents may be separately housed. Kits may comprise a means for enclosing the individual containers in relatively close confinement for commercial sale, e.g., a plastic box, in which instructions, packaging materials such as styrofoam, etc., may be enclosed.

In some embodiments, kits are used in the treatment, diagnosis, and/or prophylaxis of a subject suffering from and/or susceptible to prostate cancer. In some embodiments, such kits comprise (i) at least one fPSA-specific antibodies antibody; (ii) a syringe, needle, applicator, etc. for administration of the at least one fPSA-specific antibody to a subject; and (iii) instructions for use.

These and other aspects of the present invention will be further appreciated upon consideration of the following Examples, which are intended to illustrate certain particular embodiments of the invention but are not intended to limit its scope, as defined by the claims.

EXAMPLES

General Details

All chemicals, unless otherwise stated, were purchased from Sigma Aldrich (St. Louis, Mo.) and used without further purification. fPSA-specific 5A10 monoclonal antibody was purchased from the University of Turku, Finland, and used without further purification. Water (>18.2 MΩ·2 cm at 25° C., Milli-Q, Millipore, Billerica, Mass.) was purified by passing through a 10 cm column of chelex resin (Bio-Rad Laboratories, Hercules, Calif.) at a flow rate <1.0 mL/min. All instruments were calibrated and maintained in accordance with previously reported routine quality-control procedures. Radioactivity was measured by using a Capintec CRC-15R Dose Calibrator (Capintec, Ramsey, N.J.) with a calibration factor of 465 for $^{89}$Zr. For accurate quantification of radioactivities, experimental samples were counted for 1 min on a calibrated Perkin Elmer (Waltham, Mass.) Automatic Wizard$^2$ Gamma Counter using a dynamic energy window of 800-1000 keV for $^{89}$Zr (909 keV emission). $^{89}$Zr-radiolabeling reactions were monitored by using silica-gel impregnated glass-fibre instant thin-layer chromatography (ITLC-SG) paper (Pall Corp., East Hills, N.Y.) and analyzed on a radio-TLC plate reader (Bioscan System 200 Imaging Scanner coupled to a Bioscan Autochanger 1000 (Bioscan Inc., Washington, D.C., using Win-Scan Radio-TLC software version 2.2). Solvent systems included diethylene triamine pentaacetic acid in water (DTPA, 50 mM, pH7) and phosphate buffered saline (PBS). MDV3100 was prepared by the Organic Synthesis Core Facility at MSKCC, and reconstituted in DMSO without further purification. Testosterone pellets were purchased from Innovative Res. of America.

Example 1: Production of $^{89}$Zr-Labeled Monoclonal fPSA Antibodies

Protein Conjugation

The monoclonal antibody 5A10 and murine IgG$_1$ were conjugated to desferrioxamine B (DFO; Calbiochem, Spring Valley, Calif.) and radiolabeled with $^{89}$Zr-oxalate to give $^{89}$Zr-5A10, using procedures derived from previous studies on radiolabeled monoclonal antibodies for immuno-PET; for example, Holland, J. P. et al., $^{89}$Zr-DFO-J591 for immuno-

*PET of prostate-specific membrane antigen expression in vivo, J Nucl. Med.,* 2010, 51 (8), 1293-1300, incorporated by reference herein. Purity of the labeled antibody was assessed by radio-ITLC. FIG. 1 illustrates typical radio-ITLC chromatograms of the crude (red) and purified (blue) $^{89}$Zr-5A10. The eluant was 50 mM DTPA, pH7. The $^{89}$Zr-5A10 remains at the baseline ($R_f$=0.0) and impurities run with the solvent front ($R_f$=1.0).

DFO Conjugation to Proteins

DFO was conjugated to the proteins as follows 5A10 was added to centrifuge vials (3 mg/mL, 1 mL) and the pH adjusted to 9.5-10.0 by using aliquots of 1.0 M and 0.1 M $Na_2CO_3$(aq.). Then 4 equivalents of [Fe(N-succDFO-TFP)] was added and solution mixed gently using an automated pipette. The reaction was allowed to proceed at room temperature without agitation for 1 h before the pH was adjusted to 3.9-4.2 by the slow addition of <10 μL aliquots of 0.25 M $H_2SO_4$(aq.). Then a >10-fold excess of ethylenediaminetetraacetic acid disodium salt with (EDTA$^{2-}$.2Na$^+$ (aq.), 0.0674 mol dm$^{-3}$ in chelex 100 resin treated deionised water) with respect to [Fe(N-succDFO-TFP)] was added. The reaction was incubated in a water bath at 38° C. for 1 h during which time the solution changed from clear yellow to colourless. The DFO-conjugated 5A10 was purified by size-exclusion chromatography (Sephadex G-25 M, PD-10 column, >30 kDa, GE Healthcare; dead-volume=2.5 mL, eluted with 200 μL fractions of sterile saline to a total volume of 1.8 mL of isolated protein). DFO-murine IgG was prepared using the same procedure.

Radiolabeling

Zirconium-89 (Zr-89) was produced via the $^{89}$Y(p,n)$^{89}$Zr transmutation reaction on an EBCO TR19/9 variable beam energy cyclotron (Ebco Industries Inc., Richmond, British Columbia, Canada) in accordance with previously reported methods. $^{89}$Zr-oxalate was isolated in high radionuclidic and radiochemical purity (RCP) >99.9%, with an effective specific-activity of 195-497 MBq/μg, (5.27-13.31 mCi/μg).

$^{89}$Zr-5A10 and $^{89}$Zr-IgG were prepared by the complexation reaction of $^{89}$Zr-oxalate with DFO-conjugated 5A10 and IgG, respectively. Typical radiolabeling reactions were conducted in accordance with previously reported methods used for labeling monoclonal antibodies with $^{89}$Zr. As an example, typical conditions used to produce $^{89}$Zr-5A10 are presented. The same methods were used to produce $^{89}$Zr-IgG. Briefly, $^{89}$Zr-oxalate (429 MBq, [11.6 mCi]) in 1.0 M oxalic acid (250 μL) was adjusted to pH7.1-7.7 with 1.0 M $Na_2CO_3$(aq.). CAUTION: Acid neutralization releases $CO_2$ (g) and care should be taken to ensure that no radioactivity escapes the microcentrifuge vial. After $CO_2$ evolution ceased, DFO-conjugated 5A10 (500 μL, 2.0 mg/mL [1.0 mg of protein], in sterile saline) was added and the reaction was mixed gently by aspirating with a pipette. The reaction was incubated at room temperature for between 1-2 h and complexation progress was monitored with respect to time by ITLC (DTPA, 50 mM, pH7). After 2 h, crude radiolabeling yields and RCP were typically >80-90%. $^{89}$Zr-5A10 was purified by using spin-column centrifugation (4 mL total volume, >30 kDa particle retention, Amicon Ultra-4, Millipore, Billerica, Mass.; washed with 4×3 mL sterile saline). The radiochemical purity (RCP) of the final $^{89}$Zr-5A10 (formulation: pH5.5-6.0; <500 μL; sterile saline) was measured by ITLC and size-exclusion chromatography. In the ITLC experiment the $^{89}$Zr-5A10, $^{89}$Zr-IgG and $^{89}$Zr-DFO remain at the baseline ($R_f$=0.0), whereas $^{89}$Zr$^{4+}$ (aq.) ions and the complex $^{89}$Zr-DTPA elute with the solvent front ($R_f$=1.0). The final radiochemical yield of the purified $^{89}$Zr-5A10 was typically >70% and the product was formulated in sterile saline with RCP >99% (n=5) and a specific-activity of 195.0±8.0 MBq/mg (5.27±0.2 mCi/mg) of protein. FIG. 1 shows a typical radio-ITLC chromatogram of the crude and purified (formulated) $^{89}$Zr-5A10.

Chelate Number

The number of accessible DFO chelates conjugated to 5A10 or IgG was measured by radiometric isotopic dilution assays following methods known to those of skill in the art (e.g., Holland, J. P. et al., *Measuring the pharmacokinetic effects of a novel Hsp90 inhibitor on HER2/neu expression in mice using $^{89}$Zr-DFO-trastuzumab,* PLoS ONE, 2010, 5 (1), e8859; Anderson, C. J. et al., *Preparation, biodistribution and dosimetry of copper-64-labeled anti-colorectal carcinoma monoclonal antibody fragments 1A3-F(ab')2, J. Nucl. Med.,* 1995, 36 (5), 850-858. From a stock solution, aliquots of $^{89}$Zr-chloride (5 μL, 370 kBq [10 μCi], pH7.7-8.1 pH adjusted using 1.0 M $Na_2CO_3$]) were added to 12 solutions containing 1:2 serial dilutions of non-radioactive $ZrCl_4$(aq.) (50 μL fractions; 1000-0.5 pmol, pH7.7-8.1). The mixture was vortexed for 30 s before adding 5 μL aliquots of 5A10 (1.36 mg/mL, 6.8 μg of mAb, 0.045 nmol; sterile saline). The reactions were incubated at room temperature for 2 h before quenching with DTPA (20 μL, 50 mM, pH7). Control experiments confirmed that $^{89}$Zr complexation to DFO-conjugated protein was complete within <2 h. The extent of complexation was assessed by developing ITLC strips (DTPA, 50 mM) and counting the activity at the baseline and solvent front. The fraction of $^{89}$Zr-radiolabeled protein ($A_b$) was plotted versus the amount of non-radioactive $ZrCl_4$ added. The number of chelates was calculated by measuring the concentration of $ZrCl_4$ at which only 50% of the protein was labeled, multiplying by a factor of 2, and then dividing by the moles of protein present in the reaction. Isotopic dilution assays revealed an average of 2-3 accessible chelates per protein molecule for 5A10 and $IgG_1$, respectively.

Affinity Tests of $^{89}$Zr-Labeled 5A10

To determine the affinity of $^{89}$Zr-5A10 for fPSA, competition binding assays were conducted. The relative affinity of $^{89}$Zr-5A10 for fPSA was determined by incubating $^{89}$Zr-5A10 and variable concentrations of unlabeled 5A10 in wells coated with immobilized fPSA. The capture mAb was immobilized onto microtiter plates through physical adsorption by using low-fluorescence Maxisorp strips (Nunc, Roskilde, Denmark). The wells were coated with 1 μg of the mAb H117 in 100 L of buffer containing 0.2 mol/L $NaH_2PO_4$ buffer overnight at 35° C. Coated wells were washed twice with DELFIA wash solution, and were then saturated for 3 h at room temperature (RT) with 300 μL of a solution containing diethylenetriaminepentaacetic acid (DTPA)-treated BSA (1 g/L), sorbitol (60 g/L), Germall II (1 g/L), and 50 mmol of $NaH_2PO_4$. After saturation, the wells were aspirated, dried, and stored at 4° C. sealed plastic bags with desiccant until use.

Using a fresh sample of $^{89}$Zr-5A10, affinity assays were conducted by adding a solution of fPSA (25 μL, 47.7 ng/mL) in 100 μL of DELFIA assay buffer to each well from the previously prepared plates. After incubation for 1 h at room temperature, the solution was aspirated, and the wells were washed twice with assay buffer. The binding assay was initiated with the addition of 200 μL aliquots of assay buffer containing 20 μg of $^{89}$Zr-5A10, and 0.0, 0.002, 0.02, 0.2, 0.5, 1, 2, 4, 6, 8, or 10 μg of unlabeled 5A10. All reactions were conducted in duplicate. The reactions were incubated, with slow shaking, for 2 h at which time the wells were aspirated and rinsed four times with DELFIA wash solution. The bound activity was determined in a NaI (Tl)-well counter (Perkin Elmer 2480 Automatic Gamma Counter).

Figure 2:
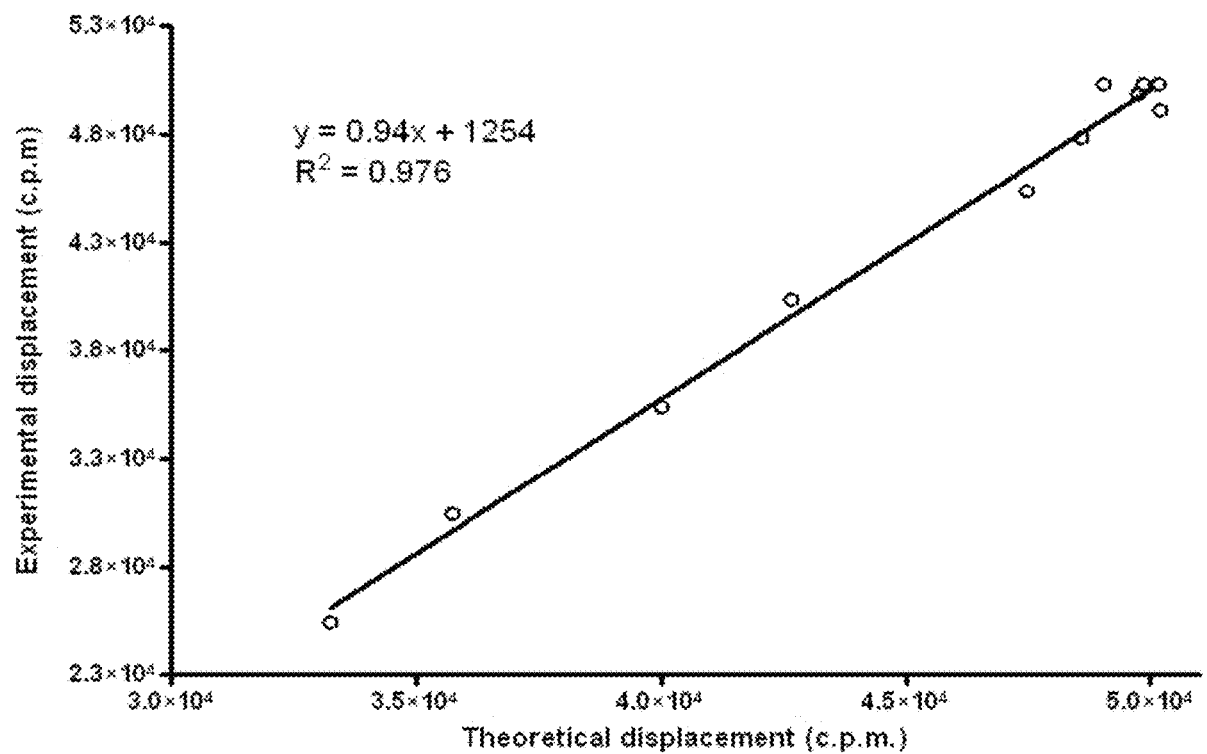
FIG. 2 depicts a competitive binding assay to determine the relative affinity of $^{89}$Zr-5A10 for fPSA. Relative affinity of $^{89}$Zr-5A10 for fPSA was determined by incubating $^{89}$Zr-5A10 and variable concentrations of unlabeled 5A10 in wells coated with immobilized fPSA. Activity retained in the well after incubation was interpreted as specific binding of $^{89}$Zr-5A10 to fPSA. Experimental values were plotted against ideal (theoretical) values, calculated on the assumption that conjugation of DFO and $^{89}$Zr to 5A10 results in no change in affinity of the mAb for fPSA. Linear regression was used to determine the deviation from linearity (y=x), and representative data from one preparation of $^{89}$Zr-5A10 is shown. Assays were conducted in duplicate, using two independent concentration ranges of 5A10 (n=4 total).

Activity retained in the well after incubation was interpreted as specific binding of $^{89}$Zr-5A10 to fPSA. The experimental values were plotted against ideal (theoretical) values, calculated on the assumption that conjugation of DFO and $^{89}$Zr to 5A10 results in no change in affinity of the mAb for fPSA. Linear regression was used to determine the deviation from linearity (y=x), and representative data from one preparation of $^{89}$Zr-5A10 is shown. Assays were conducted in duplicate, using two independent concentration ranges of 5A10 (n=4 total). The results presented in FIG. 2 demonstrate that bioconjugation of $^{89}$Zr-DFO to 5A10 resulted in no loss of affinity for purified fPSA, and that $^{89}$Zr-5A10 remained specific for fPSA.

Example 2: $^{89}$Zr-5A10 Binding In Vivo

In vivo studies were conducted by administering $^{89}$Zr-5A10 to intact male mice inoculated with subcutaneous (s.c.) xenografts of LNCaP-AR, a PSA-positive human prostate cancer model derived from parental prostate cancer cells overexpressing wild-type Androgen Receptor, as described (Chen, C. D., et al., *Molecular Determinants of Resistance to Androgen Therapy, Nat. Med.*, 2004, 10:33-39). All animal experiments were conducted in compliance with Institutional Animal Care and Use Committee (IACUC) guidelines and the *Guide for the Care and Use of Laboratory Animals*. Male CB-17 SCID mice (6-8 weeks old) were obtained from Taconic Farms Inc. (Hudson, N.Y.), LNCaP-AR, 22Rv1, and PC3 tumors were inoculated in the right flank by sub-cutaneous (s.c.) injection of $1.0 \times 10^6$ cells in a 200 µL cell suspension of a 1:1 v/v mixture of media with reconstituted basement membrane (BD Matrigel™, Collaborative Biomedical Products Inc., Bedford, Mass.). Palpable tumors (50-250 mm³) developed after a period of 3-7 weeks. Surgical castration and pellet implantation were performed according to known protocols under anesthesia with isoflurane. Tumor volume (V/mm³) was estimated by external vernier caliper measurements in accordance with previously reported methods (Holland, J. P. et al., *Measuring the pharmacokinetic effects of a novel Hsp90 inhibitor on HER2/neu expression in mice using $^{89}$Zr-DFO-trastuzumab, PLoS ONE*, 2010, 5 (1), e8859).

Figure 3:
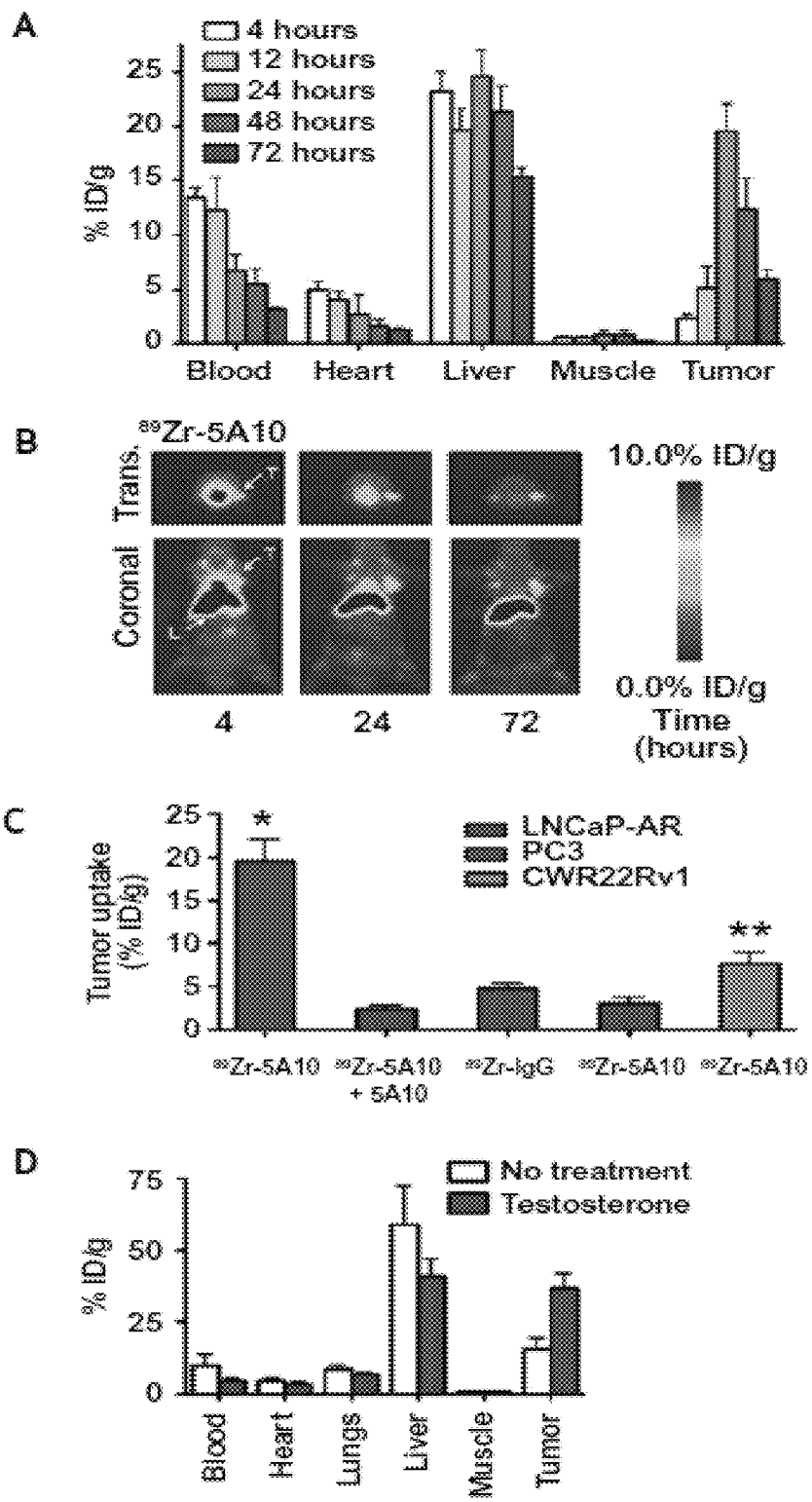
FIG. 3 depicts $^{89}$Zr-5A10 specifically localizing to multiple preclinical models of AR- and fPSA-positive prostate cancer.

Tissues were harvested at multiple time points post-injection (p.i.) to determine the kinetics of radiotracer biodistribution (FIG. 3a). Biodistribution studies were conducted to evaluate the uptake of $^{89}$Zr-5A10 in the human prostate cancer xenograft models. Mice were warmed gently with a heat lamp 5 min. before administering $^{89}$Zr-5A10 (1.11-1.85 MBq, [30-50 µCi], 5.7-9.5 µg of protein, in 200 µL sterile saline for injection) via intravenous (i.v.) tail-vein injection (t=0 h). Animals (n=4-5, per group) were euthanized by $CO_2$(g) asphyxiation at 1, 4, 12, 24, 48, 72, 96, and 120 h post-injection and 16 tissues (including the tumor) were removed, rinsed in water, dried in air for 5 min., weighed and counted on a gamma-counter for accumulation of $^{89}$Zr-radioactivity. The mass of $^{89}$Zr-5A10 formulation injected into each animal was measured and used to determine the total number of counts (counts per minute, [c.p.m.]) by comparison to a standard syringe of known activity and mass. Count data were background- and decay-corrected and the tissue uptake measured in units of percentage injected dose per gram (% ID/g) for each sample was calculated by normalization to the total amount of activity injected.

Figure 4:
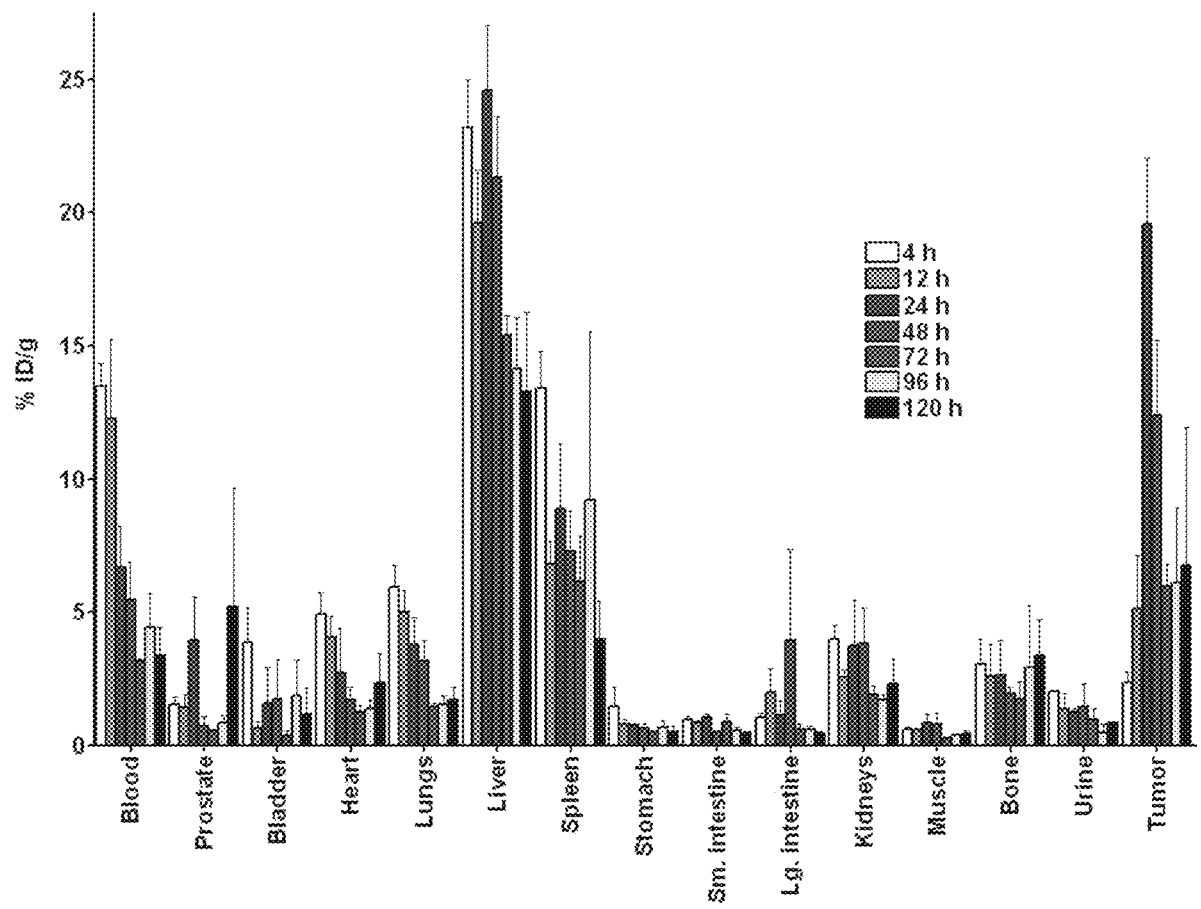
FIG. 4 depicts a biodistribution plot of intact male mice bearing LNCaP-AR xenografts injected with $^{89}$Zr-5A10. Tumor-bearing mice were treated with $^{89}$Zr-5A10, and at the indicated time post injection, were sacrificed and blood and tissues were harvested for biodistribution studies. Data are reported as mean % ID/g±one standard deviation.

Peak tumor associated activity was observed at approximately 24 hours post-injection (19.59±4.9% ID/g), and with few exceptions, little $^{89}$Zr-5A10 accumulation was observed in host tissues (FIG. 3a; FIG. 4). As shown in FIG. 4, Tumor-bearing mice were treated with $^{89}$Zr-5A10, and at the indicated time post injection, were sacrificed and blood and tissues were harvested for biodistribution studies. Data are reported as mean % ID/g±one standard deviation. Table 1 shows the ex vivo biodistribution data for $^{89}$Zr-5A10 (n=4) at multiple time points post-i.v. administration in intact male SCID mice bearing subcutaneous LNCaP-AR tumors in the right shoulder. The data are expressed as the mean % ID/g±one standard deviation (S.D.). Errors for the tumor-to-tissue ratios and tissue-to-muscle ratios are calculated as the geometric mean of the standard deviations.

TABLE 1

| Organ | 4 h (n = 4) | 12 h (n = 4) | 24 h (n = 4) | 48 h (n = 4) | 72 h (n = 4) | 96 h (n = 4) | 120 h (n = 4) |
|---|---|---|---|---|---|---|---|
| Blood | 13.49 ± 1.74 | 12.28 ± 5.93 | 6.67 ± 3.08 | 5.44 ± 2.85 | 3.16 ± 0.14 | 4.44 ± 2.55 | 3.39 ± 2.09 |
| Prostate | 1.56 ± 0.48 | 1.40 ± 0.74 | 3.95 ± 2.82 | 0.73 ± 0.49 | 0.57 | 0.86 ± 0.50 | 5.23 ± 8.82 |
| Bladder | 3.88 ± 2.55 | 0.63 ± 0.37 | 1.59 ± 1.87 | 1.75 ± 2.07 | 0.38 ± 0.25 | 1.87 ± 1.86 | 1.19 ± 1.35 |
| Heart | 4.93 ± 1.58 | 4.06 ± 1.54 | 2.74 ± 2.83 | 1.69 ± 0.95 | 1.24 ± 0.49 | 1.37 ± 0.66 | 2.36 ± 2.19 |
| Lungs | 5.94 ± 1.63 | 5.00 ± 1.61 | 3.79 ± 2.05 | 3.19 ± 1.52 | 1.46 ± 0.23 | 1.52 ± 0.66 | 1.71 ± 0.95 |
| Liver | 23.20 ± 3.55 | 19.61 ± 4.00 | 24.56 ± 4.91 | 21.30 ± 4.58 | 15.40 ± 1.47 | 14.16 ± 3.79 | 13.28 ± 5.96 |
| Spleen | 13.42 ± 2.71 | 6.80 ± 1.46 | 8.90 ± 4.19 | 7.28 ± 3.00 | 6.15 ± 3.37 | 9.19 ± 10.99 | 4.01 ± 2.46 |
| Stomach | 1.49 ± 1.49 | 0.83 ± 0.30 | 0.75 ± 0.11 | 0.64 ± 0.30 | 0.51 ± 0.04 | 0.70 ± 0.41 | 0.54 ± 0.33 |
| Sm. Intestine | 0.97 ± 0.27 | 0.83 ± 0.21 | 1.07 ± 0.22 | 0.53 ± 0.08 | 0.90 ± 0.57 | 0.56 ± 0.19 | 0.49 ± 0.05 |
| Lg. intestine | 1.07 ± 0.30 | 2.01 ± 1.77 | 1.14 ± 1.04 | 3.93 ± 6.85 | 0.59 ± 0.35 | 0.62 ± 0.19 | 0.45 ± 0.16 |
| Kidney | 3.98 ± 1.08 | 2.57 ± 0.51 | 3.74 ± 3.43 | 3.81 ± 2.72 | 1.90 ± 0.66 | 1.71 ± 0.41 | 2.33 ± 1.87 |
| Muscle | 0.59 ± 0.15 | 0.59 ± 0.14 | 0.86 ± 0.66 | 0.80 ± 0.79 | 0.28 ± 0.02 | 0.41 ± 0.09 | 0.45 ± 0.24 |
| Bone | 3.06 ± 1.82 | 2.58 ± 2.07 | 2.63 ± 2.28 | 1.94 ± 0.40 | 1.76 ± 1.30 | 2.94 ± 3.23 | 3.39 ± 2.33 |
| Tumor | 2.34 ± 0.84 | 5.13 ± 3.95 | 19.59 ± 4.99 | 12.38 ± 5.63 | 5.99 ± 1.57 | 6.10 ± 3.99 | 6.74 ± 7.36 |
| Tumor-to-tissue ratio | | | | | | | |
| Blood | 0.2 ± 0.1 | 0.4 ± 0.4 | 2.9 ± 1.5 | 2.3 ± 1.6 | 1.9 ± 0.5 | 1.4 ± 1.2 | 2.0 ± 2.5 |
| Prostate | 1.5 ± 0.7 | 3.7 ± 3.4 | 4.9 ± 3.8 | 17.0 ± 13.8 | 10.5 | 7.1 ± 6.2 | 1.3 ± 2.6 |
| Bladder | 0.6 ± 0.3 | 8.2 ± 8.9 | 12.3 ± 4.5 | 7.1 ± 4.5 | 15.9 ± 5.9 | 3.3 ± 3.0 | 5.7 ± 8.8 |
| Heart | 0.5 ± 0.4 | 1.3 ± 1.2 | 7.1 ± 8.6 | 7.3 ± 9.3 | 4.8 ± 3.5 | 4.5 ± 5.3 | 2.9 ± 4.5 |
| Lungs | 0.4 ± 0.2 | 1.0 ± 0.9 | 5.2 ± 5.5 | 3.9 ± 2.8 | 4.1 ± 1.9 | 4.0 ± 3.3 | 3.9 ± 5.7 |
| Liver | 0.1 ± 0.0 | 0.3 ± 0.2 | 0.8 ± 0.5 | 0.6 ± 0.4 | 0.4 ± 0.1 | 0.4 ± 0.3 | 0.5 ± 0.6 |
| Spleen | 0.2 ± 0.1 | 0.8 ± 0.6 | 2.2 ± 0.7 | 1.7 ± 0.9 | 1.0 ± 0.3 | 0.7 ± 0.5 | 1.7 ± 2.0 |
| Stomach | 1.6 ± 0.7 | 6.2 ± 5.0 | 25.9 ± 13.9 | 19.3 ± 11.8 | 11.7 ± 7.1 | 8.7 ± 11.9 | 12.6 ± 15.8 |
| Sm. Intestine | 2.4 ± 2.6 | 6.2 ± 5.3 | 18.2 ± 5.4 | 23.5 ± 15.5 | 6.7 ± 1.8 | 10.9 ± 9.6 | 13.7 ± 17.2 |
| Lg. intestine | 2.2 ± 1.0 | 2.6 ± 2.1 | 17.1 ± 5.6 | 3.1 ± 1.5 | 10.2 ± 7.1 | 9.9 ± 7.3 | 15.0 ± 16.5 |

TABLE 1-continued

| Organ | 4 h (n = 4) | 12 h (n = 4) | 24 h (n = 4) | 48 h (n = 4) | 72 h (n = 4) | 96 h (n = 4) | 120 h (n = 4) |
|---|---|---|---|---|---|---|---|
| Kidney | 0.6 ± 0.3 | 2.0 ± 2.3 | 5.2 ± 4.9 | 3.2 ± 5.8 | 3.2 ± 2.0 | 3.6 ± 2.6 | 2.9 ± 3.3 |
| Muscle | 4.0 ± 1.8 | 8.8 ± 7.0 | 22.8 ± 21.7 | 15.5 ± 13.1 | 21.5 ± 9.3 | 15.0 ± 10.5 | 15.0 ± 20.3 |
| Bone | 0.8 ± 0.3 | 2.0 ± 1.6 | 7.4 ± 6.1 | 6.4 ± 7.0 | 3.4 ± 0.9 | 2.1 ± 1.4 | 2.0 ± 2.4 |
| | | | Tissue-to-muscle ratio | | | | |
| Prostate | 2.6 ± 1.1 | 2.4 ± 1.4 | 4.6 ± 4.9 | 0.9 ± 1.1 | 2.1 | 2.1 ± 1.3 | 11.6 ± 20.6 |
| Bladder | 6.6 ± 4.6 | 1.1 ± 0.7 | 1.9 ± 2.6 | 2.2 ± 3.4 | 1.4 ± 0.9 | 4.6 ± 4.7 | 2.6 ± 3.3 |
| Heart | 8.3 ± 3.4 | 6.9 ± 3.1 | 3.2 ± 4.1 | 2.1 ± 2.4 | 4.4 ± 1.8 | 3.4 ± 1.8 | 5.3 ± 5.6 |
| Lungs | 10.0 ± 3.8 | 8.5 ± 3.4 | 4.4 ± 4.2 | 4.0 ± 4.4 | 5.2 ± 0.9 | 3.8 ± 1.9 | 3.8 ± 2.9 |
| Liver | 39.2 ± 11.8 | 33.5 ± 10.6 | 28.7 ± 22.9 | 26.9 ± 27.1 | 55.3 ± 7.1 | 34.9 ± 12.3 | 29.5 ± 20.7 |
| Spleen | 22.7 ± 7.5 | 11.6 ± 3.7 | 10.4 ± 9.4 | 9.1 ± 9.8 | 22.1 ± 12.3 | 22.6 ± 27.6 | 8.9 ± 7.3 |
| Stomach | 2.5 ± 2.6 | 1.4 ± 0.6 | 0.9 ± 0.7 | 0.8 ± 0.9 | 1.8 ± 0.2 | 1.7 ± 1.1 | 1.2 ± 1.0 |
| Sm. Intestine | 1.6 ± 0.6 | 1.4 ± 0.5 | 1.3 ± 1.0 | 0.7 ± 0.7 | 3.2 ± 2.1 | 1.4 ± 0.6 | 1.1 ± 0.6 |
| Lg. intestine | 1.8 ± 0.7 | 3.4 ± 3.1 | 1.3 ± 1.6 | 4.9 ± 9.9 | 2.1 ± 1.3 | 1.5 ± 0.6 | 1.0 ± 0.6 |
| Kidney | 6.7 ± 2.5 | 4.4 ± 1.4 | 4.9 ± 5.2 | 4.8 ± 5.8 | 6.8 ± 2.4 | 4.2 ± 1.4 | 5.2 ± 5.0 |
| Bone | 5.2 ± 3.4 | 4.4 ± 3.7 | 3.1 ± 3.6 | 2.4 ± 2.5 | 6.3 ± 4.7 | 7.2 ± 8.1 | 7.5 ± 6.6 |
| Tumor | 4.0 ± 1.7 | 8.8 ± 7.1 | 22.8 ± 18.6 | 15.5 ± 16.9 | 21.5 ± 5.9 | 15.0 ± 10.4 | 15.0 ± 18.2 |

Table 2 shows the analysis of PSA expression levels from tumor tissue via ELISA in intact male mice bearing LNCaP-AR tumors, and injected with $^{89}$Zr-5A10. Mice were injected with $^{89}$Zr-5A10, and at the indicated time point post injection, were sacrificed for PSA analysis. Tumor tissues were surgically excised. fPSA and total PSA ("tPSA") were determined with PSA-directed ELISA, and the values were normalized to total protein concentration. fPSA concentrations are reported as average ng/ml (a), total PSA ("tPSA") concentrations are reported as ng/mL (b), and total protein concentrations are reported as ng/mg (c). ELISAs were conducted as follows for PSA detection in serum and tumor tissues. fPSA and tPSA were measured with a dual-label immunofluorometric assay (DELFIA Prostatus™ PSA Free/Total PSA; Perkin-Elmer Life Sciences) according to manufacturer's recommendations. This assay measured fPSA and complexed PSA (cPSA) in an equimolar fashion[8], and the cross-reactivity of PSA-ACT for fPSA was <0.2% [9]. The lower limits of detection were 0.05 μg/L for tPSA (CV=5.0% at 2.32 μg/L) and 0.04 μg/L for fPSA (CV=5.9% at 0.25 μg/L). For detection, the 1235 automatic immunoassay system from Perkin-Elmer Life Sciences was used. cPSA concentrations were calculated by subtracting fPSA from tPSA.

TABLE 2

| Mouse # | Notes | Average fPSA$^a$ | Average tPSA$^b$ | f/t PSA Ratio | Total Protein$^c$ | fPSA/ tProtein | tPSA/ tProtein |
|---|---|---|---|---|---|---|---|
| 1.00 | 4 h | 171.81 | 239.75 | 0.72 | 6.20 | 27.72 | 38.68 |
| 2.00 | | 134.54 | 175.90 | 0.76 | 5.35 | 25.14 | 32.88 |
| 3.00 | | 355.69 | 537.93 | 0.66 | 6.65 | 53.48 | 80.88 |
| 5.00 | 12 h | 282.14 | 420.15 | 0.67 | 6.30 | 44.75 | 66.64 |
| 6.00 | | 28.22 | 37.33 | 0.76 | 5.03 | 5.61 | 7.42 |
| 7.00 | | 114.51 | 147.79 | 0.77 | 4.92 | 23.29 | 30.06 |
| 8.00 | | 87.30 | 113.79 | 0.77 | 6.24 | 13.98 | 18.23 |
| 9.00 | 24 h | 158.19 | 212.62 | 0.74 | 6.15 | 25.74 | 34.60 |
| 10.00 | | 96.50 | 125.22 | 0.77 | 5.43 | 17.78 | 23.07 |
| 11.00 | | 106.40 | 146.10 | 0.73 | 6.21 | 17.13 | 23.52 |
| 12.00 | | 264.55 | 355.14 | 0.74 | 6.10 | 43.38 | 58.23 |
| 13.00 | 48 h | 252.67 | 339.09 | 0.75 | 5.54 | 45.64 | 61.25 |
| 14.00 | | 337.09 | 494.87 | 0.68 | 6.25 | 53.94 | 79.19 |
| 15.00 | | 80.$^{89}$ | 99.39 | 0.81 | 5.80 | 13.94 | 17.13 |
| 16.00 | | 237.97 | 365.96 | 0.65 | 5.83 | 40.83 | 62.78 |
| 17.00 | 72 h | 178.$^{89}$ | 253.99 | 0.70 | 5.96 | 30.03 | 42.64 |
| 18.00 | | 324.82 | 477.48 | 0.68 | 6.71 | 48.43 | 71.19 |
| 19.00 | | 140.96 | 229.85 | 0.61 | 6.57 | 21.44 | 34.96 |
| 20.00 | | 248.42 | 326.42 | 0.76 | 5.20 | 47.80 | 62.81 |
| 21.00 | 96 h | 228.56 | 329.97 | 0.69 | 5.61 | 40.76 | 58.85 |
| 22.00 | | 171.25 | 225.05 | 0.76 | 5.31 | 32.27 | 42.41 |

TABLE 2-continued

| Mouse # | Notes | Average fPSA$^a$ | Average tPSA$^b$ | f/t PSA Ratio | Total Protein$^c$ | fPSA/ tProtein | tPSA/ tProtein |
|---|---|---|---|---|---|---|---|
| 23.00 | | 55.37 | 71.39 | 0.78 | 5.01 | 11.05 | 14.25 |
| 24.00 | | 115.80 | 159.40 | 0.73 | 5.90 | 19.62 | 27.01 |
| 27.00 | | 56.49 | 68.26 | 0.83 | 3.59 | 15.75 | 19.03 |
| 28.00 | | 71.14 | 94.26 | 0.75 | 6.04 | 11.78 | 15.61 |

PET studies showed a region of contrast at the tumor, supportive of the biodistribution data (FIG. 3b). FIG. 3b provides representative transverse (Trans.) and coronal PET slices of intact male mice bearing LNCaPAR xenografts shows localization of $^{89}$Zr-5A10 to the tumor (T) and uptake in the murine liver (L). PET imaging experiments were conducted on a microPET Focus 120 scanner (Concorde Microsystems). In repeated studies (n=4) mice were administered formulations of $^{89}$Zr-5A10 (10.4-12.6 MBq, [280-340 μCi], 53.1-64.5 μg of protein, in 200 μL sterile saline for injection) via i.v. tail-vein injection. Approximately 5 min prior to recording PET images, mice were anesthetized by inhalation of 1-2% isoflurane (Baxter Healthcare, Deerfield, Ill.)/oxygen gas mixture and placed on the scanner bed. PET images were recorded at various time-points between 1-120 h post-injection. List-mode data were acquired for between 10 and 30 min. using a γ-ray energy window of 350-750 keV, and a coincidence timing window of 6 ns. For all static images, scan time was adjusted to ensure a minimum of 20 million coincident events were recorded. Data were sorted into 2-dimensional histograms by Fourier re-binning, and transverse images were reconstructed by filtered back-projection (FBP) into a 128×128×63 (0.72×0.72×1.3 mm) matrix. The reconstructed spatial resolution for $^{89}$Zr was 1.9 mm full-width half maximum (FWHM) at the center of the field-of-view (FOV). The image data were normalized to correct for non-uniformity of response of the PET, dead-time count losses, positron branching ratio, and physical decay to the time of injection but no attenuation, scatter, or partial-volume averaging correction was applied. An empirically determined system calibration factor (in units of [mCi/mL]/[cps/voxel]) for mice was used to convert voxel count rates to activity concentrations. The resulting image data were then normalised to the administered activity to parameterise images in terms of % ID/g. Manually drawn 2-dimensional regions-of-interest (ROIs) or 3-dimensional volumes-of-interest (VOIs) were used to determined the maximum and mean % ID/g (decay corrected to the time of injection) in various tissues. Images were analyzed by using ASIPro VM™ software (Concorde Microsystems).

Figure 5:
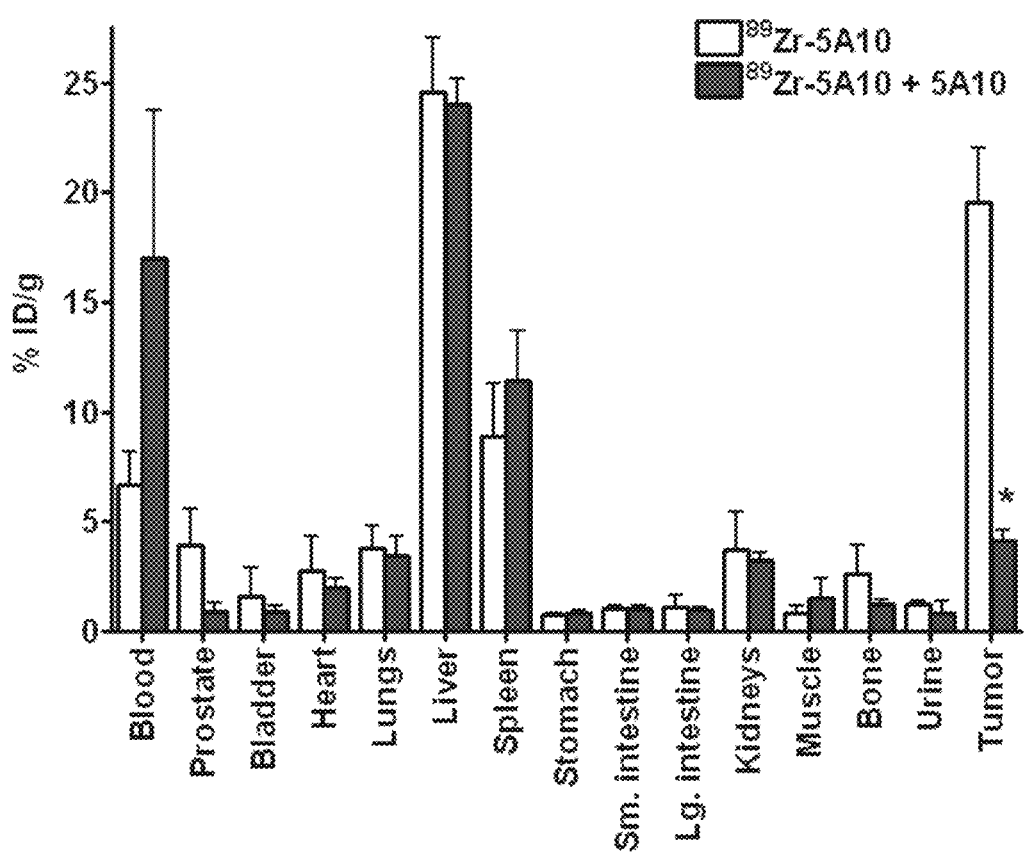
FIG. 5 depicts a biodistribution plot of intact male mice bearing LNCaP-AR xenografts injected with $^{89}$Zr-5A10 and excess unlabeled 5A10. Tumor-bearing mice were co-treated with $^{89}$Zr-5A10 and excess 5A10 (1 mg/mouse), and at 24 h post injection, were sacrificed and blood and tissues were harvested for biodistribution studies. Data are reported as mean % ID/g±one standard deviation. *P<0.01 for the intratumoral uptake of $^{89}$Zr-5A10 in the animals receiving unlabeled 5A10 compared to tracer alone.

Using 100-fold excess of unlabeled 5A10 to compete $^{89}$Zr-5A10 uptake, the specificity of the biological interaction between $^{89}$Zr-5A10 and LNCaP-AR was confirmed (FIG. 3c, FIG. 5, Table 3, and Table 4). Tumor-bearing mice were co-treated with $^{89}$Zr-5A10 and excess 5A10 (1 mg/mouse), and at 24 h post injection, were sacrificed and blood and tissues were harvested for biodistribution studies. FIG. 3c provides biodistribution data showing tumor associated $^{89}$Zr-5A10 in multiple s.c. PCa models and several treatment conditions in intact male mice. The localization of $^{89}$Zr-5A10 to LNCaPAR was entirely competed by co-injection with excess unlabeled 5A10 (1 mg unlabeled mAb). The non-specific radiotracer $^{89}$Zr-IgG did not localize to LNCaP-AR, and $^{89}$Zr-5A10 did not localize to PC3, an AR- and PSA-null model of prostate cancer. Intermediate localization of $^{89}$Zr-5A10 to CWR22Rv1 xenografts was observed, consistent with the lower basal expression of PSA in this model compared to LNCaP-AR. *P<0.01 compared to all conditions. "P<0.01 compared to PC3. Table 3 shows the biodistribution data for $^{89}$Zr-5A10 uptake in intact mice bearing LNCaP-AR tumors, co-injected with excess unlabeled 5A10. Ex vivo biodistribution data for $^{89}$Zr-5A10 (n=4) at multiple time points post-i.v. administration, and co-injection of 1 mg 5A10, in intact male SCID mice bearing subcutaneous LNCaP-AR tumors in the right shoulder. The data are expressed as the mean % ID/g±one standard deviation (S.D.). Errors for the ratios are calculated as the geometric mean of the standard deviations.

TABLE 3

| Organ | Biodistribution | | Tumor-to-tissue ratio | | Tissue-to-muscle ratio | |
|---|---|---|---|---|---|---|
| | Sham 24 h (n = 4) | Block 24 h (n = 4) | Sham 24 h (n = 4) | Block. 24 h (n = 4) | Sham 24 h (n = 4) | Block 24 h (n = 4) |
| Blood | 6.67 ± 3.0 | 17.0 ± 13.4 | 2.9 ± 1.5 | 0.2 ± 0.2 | | |
| Bladder | 1.59 ± 1.8 | 0.93 ± 0.3 | 12.3 ± 14.9 | 4.4 ± 2 | 1.9 ± 2.6 | 0.6 ± 0.7 |
| Heart | 2.74 ± 2.8 | 2.03 ± 0.7 | 7.1 ± 7.6 | 2.0 ± 0.9 | 3.2 ± 4.1 | 1.3 ± 1.5 |
| Lungs | 3.79 ± 2.0 | 3.47 ± 1.7 | 5.2 ± 3.1 | 1.2 ± 0.6 | 4.4 ± 4.2 | 2.2 ± 2.7 |
| Liver | 24.56 ± 4.9 | 24.0 ± 2.3 | 0.8 ± 0.3 | 0.2 ± 0 | 28.7 ± 22.9 | 15.4 ± 16.7 |
| Spleen | 8.90 ± 4.1 | 11.43 ± 4.51 | 2.2 ± 1.2 | 0.4 ± 0.2 | 10.4 ± 9.4 | 7.3 ± 8.4 |
| Stomach | 0.75 ± 0.11 | 0.86 ± 0.2 | 25.9 ± 7.7 | 4.8 ± 1 | 0.9 ± 0.7 | 0.6 ± 0.6 |
| Sm. Intestine | 1.07 ± 0.2 | 1.04 ± 0.2 | 18.2 ± 6.0 | 4.0 ± 1 | 1.3 ± 1.0 | 0.7 ± 0.7 |
| Lg. intestine | 1.14 ± 1.04 | 1.00 ± 0.2 | 17.1 ± 16.2 | 1.3 ± 0.4 | 1.3 ± 1.6 | 0.6 ± 0.7 |
| Kidney | 3.74 ± 3.4 | 3.26 ± 0.7 | 5.2 ± 5.0 | 2.7 ± 3 | 4.4 ± 5.2 | 2.1 ± 2.3 |
| Muscle | 0.86 ± 0.6 | 1.56 ± 1.6 | 22.8 ± 18 | 3.2 ± 1 | | |
| Bone | 2.63 ± 2.2 | 1.27 ± 0.3 | 7.4 ± 6 | 1.0 ± 0.3 | 3.1 ± 3.4 | 1.0 ± 1.5 |
| Tumor | 19.54 ± 4.9 | 4.12 ± 0.9 | | | 22.8 ± 26.5 | 0.8 ± 0.9 |

Table 4 contains tumor measurements of PSA in intact male mice bearing LNCaP-AR xenografts, and co-injected with 89Zr-5A10 and excess unlabeled 5A10. Mice were injected with 89Zr-5A10 and excess unlabeled 5A10 (1 mg), and at the indicated time point post injection, were sacrificed for PSA analysis. Tumor tissues were surgically excised. fPSA and tPSA were determined with PSA-directed ELISA (as above), and the values were normalized to total protein concentration. afPSA concentrations are reported as ng/ml, btotal PSA concentrations are reported as ng/mL, ctotal protein concentrations are reported as ng/mg. Abbreviations: fPSA, fPSA; tPSA, total PSA

TABLE 4

| Mouse # | Sample | fPSA[a] | tPSA[b] | f/t PSA Ratio | tProtein[c] | fPSA/tProtein | tPSA/tProtein |
|---|---|---|---|---|---|---|---|
| 1.0 | Tumor | 10.1 | 250.4 | 0.0 | 5.2 | 1.9 | 47.8 |
| 2.0 | Tumor | 9.7 | 220.6 | 0.0 | 6.1 | 1.6 | 36.2 |
| 3.0 | Tumor | 15.7 | 613.0 | 0.0 | 6.2 | 2.5 | 98.1 |
| 4.0 | Tumor | 11.5 | 483.4 | 0.0 | 6.1 | 1.9 | 78.9 |

Figure 6:
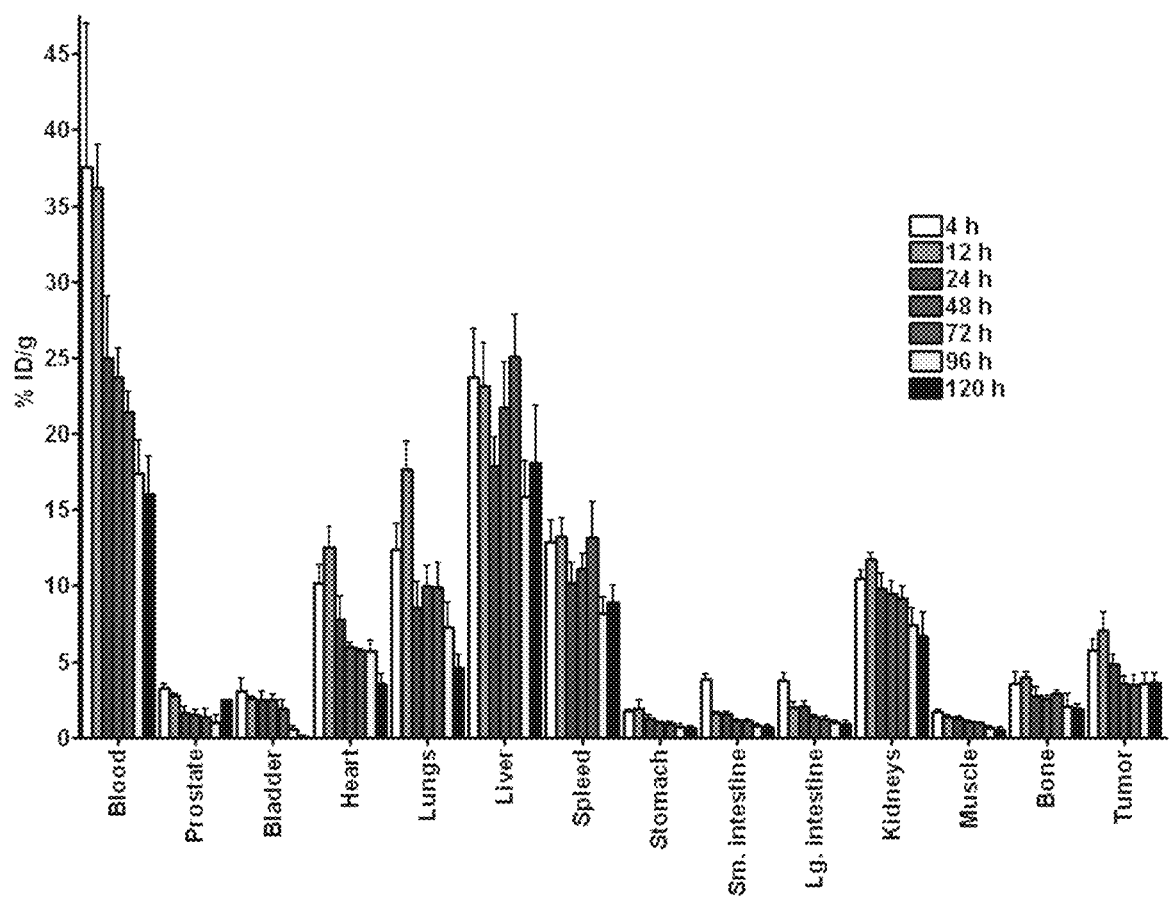
FIG. 6 depicts a biodistribution plot of intact male mice bearing LNCaP-AR xenografts injected with $^{89}$Zr-IgG. Tumor-bearing mice were treated with $^{89}$Zr-IgG, and at the indicated time post injection, were sacrificed and blood and tissues were harvested for biodistribution studies. Data are reported as mean % ID/g±one standard deviation.

Moreover, there was little incorporation of the non-specific radiotracer $^{89}$Zr-labelled mouse IgG in LNCaP-AR at 24 h p.i. (FIG. 3c, FIG. 6, Table 5, and Table 6). FIG. 6 shows a biodistribution plot of intact male mice bearing LNCaP-AR, PC3, or CWR22Rv1 xenografts injected with $^{89}$Zr-5A10. Tumor-bearing mice were treated with $^{89}$Zr-5A10, and at 24 h post-injection, were sacrificed and blood and tissues were harvested for biodistribution studies. Data are reported as mean % ID/g±one standard deviation. Table 5 shows biodistribution data for $^{89}$Zr-IgG uptake in intact mice bearing LNCaP-AR tumors. Ex vivo biodistribution data for $^{89}$Zr-IgG (n=4) at multiple time points post-i.v. administration in intact male SCID mice bearing subcutaneous LNCaP-AR tumors in the right shoulder. The data are expressed as the mean % ID/g±one standard deviation (S.D.). Errors for the ratios are calculated as the geometric mean of the standard deviations.

TABLE 5

| Tissue | 4 h (n = 4) | 12 h (n = 4) | 24 h (n = 4) | 48 h (n = 4) | 72 h (n = 4) | 96 h (n = 4) | 120 h (n = 4) |
|---|---|---|---|---|---|---|---|
| Blood | 37.55 ± 16.43 | 36.17 ± 5.68 | 24.96 ± 8.14 | 23.71 ± 3.79 | 21.54 ± 2.64 | 17.39 ± 4.42 | 16.04 ± 4.89 |
| Prostate | 3.25 ± 0.57 | 2.76 ± 0.25 | 1.66 ± 0.86 | 1.49 ± 0.72 | 1.31 ± 1.24 | 1.01 ± 0.69 | 2.51 |
| Bladder | 10.16 ± 2.45 | 12.53 ± 2.73 | 7.73 ± 3.12 | 5.95 ± 0.67 | 5.69 ± 0.35 | 5.68 ± 1.51 | 3.52 ± 1.40 |
| Heart | 12.35 ± 3.43 | 17.64 ± 3.76 | 8.51 ± 3.46 | 9.98 ± 2.73 | 9.88 ± 3.32 | 7.23 ± 3.39 | 4.60 ± 1.77 |
| Lungs | 23.73 ± 6.35 | 23.12 ± 5.80 | 17.88 ± 3.77 | 21.73 ± 6.01 | 25.09 ± 5.59 | 15.91 ± 4.64 | 18.10 ± 7.46 |
| Liver | 12.86 ± 2.86 | 13.26 ± 2.36 | 10.15 ± 2.75 | 11.07 ± 2.24 | 13.16 ± 4.74 | 8.21 ± 2.04 | 8.87 ± 2.29 |
| Spleen | 1.76 ± 0.21 | 1.92 ± 1.18 | 1.30 ± 0.41 | 0.99 ± 0.18 | 0.89 ± 0.32 | 0.73 ± 0.30 | 0.66 ± 0.24 |
| Stomach | 3.83 ± 0.71 | 1.64 ± 0.13 | 1.57 ± 0.26 | 1.13 ± 0.16 | 1.10 ± 0.21 | 0.74 ± 0.32 | 0.77 ± 0.22 |
| Sm. Intestine | 3.77 ± 0.98 | 2.00 ± 0.69 | 2.04 ± 0.76 | 1.31 ± 0.31 | 1.21 ± 0.40 | 0.98 ± 0.31 | 0.94 ± 0.37 |
| Lg. intestine | 10.44 ± 1.20 | 11.76 ± 0.84 | 9.79 ± 2.07 | 9.43 ± 1.79 | 9.18 ± 1.63 | 7.41 ± 2.30 | 6.70 ± 3.16 |
| Kidney | 1.66 ± 0.42 | 1.37 ± 0.18 | 1.26 ± 0.28 | 1.08 ± 0.09 | 0.97 ± 0.10 | 0.65 ± 0.18 | 0.50 ± 0.35 |
| Muscle | 3.55 ± 1.40 | 3.94 ± 0.85 | 2.74 ± 1.25 | 2.53 ± 0.41 | 2.94 ± 0.39 | 2.06 ± 1.75 | 1.89 ± 0.56 |
| Bone | 5.74 ± 1.43 | 7.04 ± 2.45 | 4.80 ± 1.31 | 3.52 ± 1.13 | 3.45 ± 1.37 | 3.56 ± 1.44 | 3.65 ± 1.16 |
| Tumor | 3.05 ± 1.68 | 2.55 ± 0.24 | 2.49 ± 1.14 | 2.52 ± 0.61 | 1.89 ± 1.12 | 0.59 ± 0.36 | 0.09 ± 0.08 |
| Tumor-to-tissue ratio | | | | | | | |
| Blood | 0.2 ± 0.1 | 0.2 ± 0.0 | 0.2 ± 0.1 | 0.1 ± 0.0 | 0.2 ± 0.1 | 0.2 ± 0.1 | 0.2 ± 0.1 |
| Prostate | 1.8 ± 0.4 | 2.5 ± 0.3 | 2.9 ± 1.6 | 2.4 ± 1.2 | 2.6 ± 2.6 | 3.5 ± 2.5 | 1.5 |
| Bladder | 1.9 ± 1.1 | 2.8 ± 0.3 | 1.9 ± 1.0 | 1.4 ± 0.4 | 1.8 ± 1.3 | 6.1 ± 3.9 | 42.5 ± 19.1 |
| Heart | 0.6 ± 0.1 | 0.6 ± 0.1 | 0.6 ± 0.3 | 0.6 ± 0.1 | 0.6 ± 0.2 | 0.6 ± 0.2 | 1.0 ± 1.0 |
| Lungs | 0.5 ± 0.1 | 0.4 ± 0.1 | 0.6 ± 0.3 | 0.4 ± 0.1 | 0.3 ± 0.2 | 0.5 ± 0.3 | 0.8 ± 0.4 |
| Liver | 0.2 ± 0.1 | 0.3 ± 0.1 | 0.3 ± 0.1 | 0.2 ± 0.1 | 0.1 ± 0.1 | 0.2 ± 0.1 | 0.2 ± 0.1 |
| Spleen | 0.4 ± 0.1 | 0.5 ± 0.1 | 0.5 ± 0.2 | 0.3 ± 0.1 | 0.3 ± 0.1 | 0.4 ± 0.1 | 0.4 ± 0.2 |
| Stomach | 3.3 ± 0.5 | 3. ± 2.3 | 3.7 ± 1.4 | 3.6 ± 1.0 | 3.9 ± 2.0 | 4.9 ± 2.2 | 5.6 ± 2.3 |
| Sm. Intestine | 1.5 ± 0.3 | 4.3 ± 0.4 | 3.1 ± 0.7 | 3.1 ± 0.8 | 3.1 ± 1.3 | 4.8 ± 2.3 | 5.0 ± 2.4 |
| Lg. intestine | 1.5 ± 0.4 | 3.5 ± 1.2 | 2.4 ± 1.0 | 2.7 ± 0.8 | 2.8 ± 1.4 | 3.6 ± 1.3 | 3.9 ± 1.7 |
| Kidney | 3.5 ± 0.9 | 0.6 ± 0.0 | 0.5 ± 0.1 | 0.4 ± 0.1 | 0.4 ± 0.2 | 0.5 ± 0.2 | 0.5 ± 0.3 |
| Muscle | 1.6 ± 0.7 | 5.2 ± 0.7 | 3.8 ± 1.1 | 3.3 ± 0.7 | 3.6 ± 1.3 | 5.5 ± 1.9 | 7.3 ± 4.2 |
| Bone | 1.66 ± 0.42 | 1.8 ± 0.4 | 1.8 ± 0.9 | 1.4 ± 0.4 | 1.2 ± 0.4 | 1.7 ± 1.5 | 1.9 ± 1.5 |
| Tissue-to-muscle ratio | | | | | | | |
| Prostate | 2.0 ± 0.6 | 2.0 ± 0.3 | 1.3 ± 0.7 | 1.4 ± 0.7 | 1.4 ± 1.3 | 1.6 ± 1.2 | 5 |
| Bladder | 3.5 ± 1.2 | 5.2 ± 1.9 | 3.8 ± 1.3 | 3.3 ± 1.1 | 3.6 ± 1.5 | 5.5 ± 2.7 | 7.3 ± 5.6 |
| Heart | 1.8 ± 1.1 | 1.9 ± 0.3 | 2.0 ± 1.0 | 2.3 ± 0.6 | 2.0 ± 1.2 | 0.9 ± 0.6 | 0.2 ± 0.2 |
| Lungs | 6.1 ± 2.1 | 9.2 ± 2.3 | 6.2 ± 2.8 | 5.5 ± 0.8 | 5.9 ± 0.7 | 8.7 ± 3.4 | 7.1 ± 5.7 |
| Liver | 7.4 ± 2.8 | 12.9 ± 3.2 | 6.8 ± 3.1 | 9.2 ± 2.6 | 10.2 ± 3.6 | 11.1 ± 6.1 | 9.2 ± 7.3 |
| Spleen | 14.3 ± 5.2 | 16.9 ± 4.8 | 14.2 ± 4.4 | 20.1 ± 5.8 | 25.9 ± 6.4 | 24.5 ± 9.9 | 36.2 ± 29.4 |
| Stomach | 7.7 ± 2.6 | 9.7 ± 2.2 | 8.1 ± 2.8 | 10.3 ± 2.1 | 13.6 ± 5.1 | 12.7 ± 4.7 | 17.7 ± 13.2 |
| Sm. Intestine | 1.1 ± 0.3 | 1.4 ± 0.9 | 1.0 ± 0.4 | 0.9 ± 0.2 | 0.9 ± 0.4 | 1.1 ± 0.6 | 1.3 ± 1.0 |
| Lg. intestine | 2.3 ± 0.7 | 1.2 ± 0.2 | 1.3 ± 0.3 | 1.0 ± 0.2 | 1.1 ± 0.3 | 1.1 ± 0.6 | 1.5 ± 1.1 |
| Kidney | 2.3 ± 0.8 | 1.5 ± 0.5 | 1.6 ± 0.7 | 1.2 ± 0.3 | 1.3 ± 0.4 | 1.5 ± 0.6 | 1.9 ± 1.5 |
| Bone | 6.3 ± 1.7 | 8.6 ± 1.3 | 7.8 ± 2.4 | 8.7 ± 1.8 | 9.5 ± 2.0 | 11.4 ± 4.8 | 13.4 ± 11.3 |
| Tumor | 2.1 ± 1.0 | 2.9 ± 0.7 | 2.2 ± 1.1 | 2.3 ± 0.4 | 3.0 ± 0.5 | 3.2 ± 2.8 | 3.8 ± 2.9 |

Table 6 shows tumor analysis of PSA expression levels via ELISA in intact male mice bearing LNCaP-AR tumors, and injected with $^{89}$Zr-IgG. Mice were injected with $^{89}$Zr-IgG, and at the indicated time point post injection, were sacrificed for PSA analysis. Tumor tissues were surgically excised. fPSA and tPSA were determined with PSA-directed ELISA (as above), and in the case of intratumoral PSA, the values were normalized to total protein concentration. [a]fPSA concentrations are reported as ng/ml, [b]total PSA concentrations are reported as ng/mL, [c]total protein concentrations are reported as ng/mg. Abbreviations: fPSA, fPSA; tPSA, total PSA.

TABLE 6

| Mouse | Notes | fPSA[a] | tPSA[b] | f/t PSA Ratio | Total Protein[c] | fPSA/ tProtein | tPSA/ tProtein |
|---|---|---|---|---|---|---|---|
| 1 | 4 h | 132.6 | 180.2 | 74% | 5.6 | 23.7 | 32.2 |
| 2 | | 71.2 | 94.0 | 76% | 4.8 | 14.7 | 19.4 |
| 3 | | 114.6 | 155.5 | 74% | 6.7 | 17.1 | 23.2 |
| 4 | | 61.4 | 78.5 | 78% | 5.4 | 11.3 | 14.5 |
| 5 | 12 h | 174.2 | 250.4 | 70% | 6.9 | 25.1 | 36.1 |
| 6 | | 59.3 | 79.1 | 75% | 4.7 | 12.6 | 16.8 |

TABLE 6-continued

| Mouse | Notes | fPSA[a] | tPSA[b] | f/t PSA Ratio | Total Protein[c] | fPSA/ tProtein | tPSA/ tProtein |
|---|---|---|---|---|---|---|---|
| 7 |  | 161.7 | 232.2 | 70% | 6.3 | 25.6 | 36.8 |
| 8 |  | 259.8 | 369.5 | 70% | 7.1 | 36.6 | 52.1 |
| 9 | 24 h | 105.2 | 140.0 | 75% | 6.2 | 16.9 | 22.5 |
| 10 |  | 147.4 | 214.9 | 69% | 6.9 | 21.4 | 31.3 |
| 11 |  | 141.3 | 199.3 | 71% | 6.1 | 23.2 | 32.7 |
| 12 |  | 115.9 | 155.2 | 75% | 5.5 | 21.2 | 28.4 |
| 13 | 48 h | 55.5 | 75.8 | 73% | 5.9 | 9.4 | 12.8 |
| 14 |  | 73.1 | 87.0 | 84% | 6.3 | 11.5 | 13.7 |
| 15 |  | 39.4 | 47.4 | 83% | 3.7 | 10.7 | 12.8 |
| 16 |  | 40.9 | 53.1 | 77% | 4.5 | 9.1 | 11.8 |
| 17 | 72 h | 110.9 | 152.9 | 73% | 6.2 | 17.9 | 24.6 |
| 18 |  | 114.5 | 145.2 | 79% | 6.7 | 17.2 | 21.8 |
| 19 |  | 203.5 | 277.8 | 73% | 7.2 | 28.1 | 38.4 |
| 20 |  | 93.5 | 124.8 | 75% | 7.2 | 13.0 | 17.3 |
| 21 | 96 h | 22.6 | 30.7 | 74% | 3.1 | 7.4 | 10.0 |
| 22 |  | 116.4 | 147.7 | 79% | 7.4 | 15.8 | 20.0 |
| 23 |  | 95.8 | 123.4 | 78% | 6.6 | 14.5 | 18.7 |
| 24 |  | 189.4 | 251.8 | 75% | 6.8 | 28.0 | 37.2 |
| 25 | 120 h | 101.9 | 135.3 | 75% | 6.6 | 15.3 | 20.4 |
| 26 |  | 87.0 | 112.5 | 77% | 5.9 | 14.8 | 19.1 |
| 27 |  | 214.4 | 304.4 | 70% | 7.5 | 28.7 | 40.7 |
| 28 |  | 132.0 | 179.4 | 74% | 6.2 | 21.2 | 28.7 |
| 29 | Not injected | 217.9 | 303.8 | 72% | 7.7 | 28.2 | 39.3 |
| 30 | Not injected | 157.2 | 215.3 | 73% | 7.1 | 22.0 | 30.1 |
| 31 | Not injected | 183.0 | 239.7 | 76% | 6.0 | 30.5 | 39.9 |
| 32 | Not injected | 49.7 | 63.0 | 79% | 4.3 | 11.6 | 14.7 |

Figure 7:
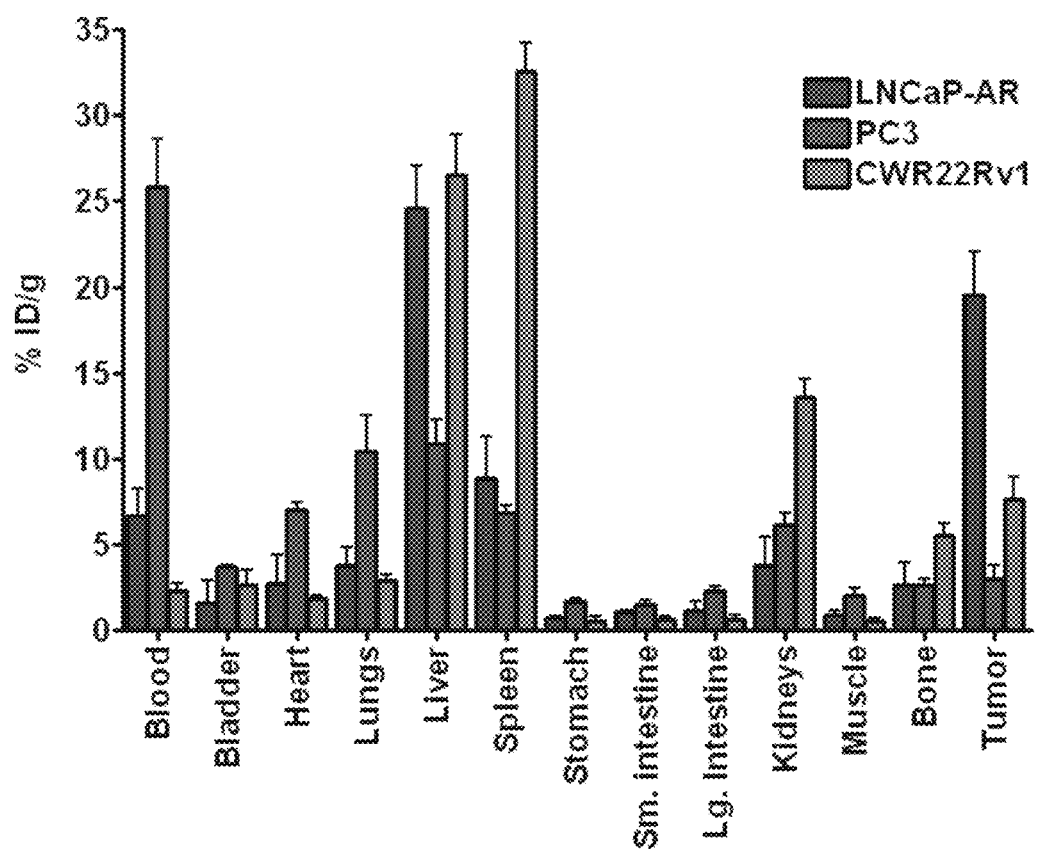
FIG. 7 depicts a biodistribution plot of intact male mice bearing LNCaP-AR, PC3, or CWR22Rv1 xenografts injected with $^{89}$Zr-5A10. Tumor-bearing mice were treated with $^{89}$Zr-5A10, and at 24 h post injection, were sacrificed and blood and tissues were harvested for biodistribution studies. Data are reported as mean % ID/g±one standard deviation.

As expected, PC3 xenografts, an AR- and PSA-negative model of human PCa, showed little avidity for [89]Zr-5A10 at 24 h p.i. (FIG. 3c, FIG. 7 and Table 7). In FIG. 7, tumor-bearing mice were treated with [89]Zr-5A10, and at 24 h post injection, were sacrificed and blood and tissues were harvested for biodistribution studies. Data are reported as mean % ID/g± one standard deviation.

Table 7 shows biodistribution data for [89]Zr-5A10 uptake in intact male mice bearing PC3 tumors. Ex vivo biodistribution data for [89]Zr-5A10 uptake in intact male mice (n=4) with subcutaneous PC3 tumors. Data was acquired 24 h post-i.v. administration. Data are expressed as the mean % ID/g±one standard deviation (S.D.). Errors for the ratios are calculated as the geometric mean of the standard deviations.

TABLE 7

| Biodistribution | | Tumor-to-tissue ratio | | Tissue-to-muscle ratio | |
|---|---|---|---|---|---|
| Organ | 24 h (n = 4) | Organ | 24 h (n = 4) | Organ | 24 h (n = 4) |
| Blood | 25.86 ± 5.5 | Blood | 0.1 ± 0.1 | Prostate | 0.8 ± 0.5 |
| Prostate | 1.71 ± 0.8 | Prostate | 1.7 ± 1.3 | Bladder | 1.5 ± 0.9 |
| Bladder | 2.99 ± 1.5 | Bladder | 0.8 ± 0.6 | Heart | 1.8 ± 0.7 |
| Heart | 3.68 ± 0.2 | Heart | 0.4 ± 0.2 | Lungs | 3.4 ± 1.4 |
| Lungs | 7.00 ± 0.9 | Lungs | 0.3 ± 0.1 | Liver | 5.1 ± 2.8 |
| Liver | 10.43 ± 4.2 | Liver | 0.3 ± 0.2 | Spleen | 5.3 ± 2.4 |
| Spleen | 10.90 ± 2.7 | Spleen | 0.4 ± 0.2 | Stomach | 3.3 ± 1.3 |
| Stomach | 6.83 ± 0.9 | Stomach | 1.8 ± 1.0 | Sm. Intestine | 0.8 ± 0.4 |
| Sm. Intestine | 1.64 ± 0.3 | Sm. Intestine | 2.0 ± 1.1 | Lg. intestine | 0.7 ± 0.4 |
| Lg. intestine | 1.50 ± 0.5 | Lg. intestine | 1.3 ± 0.8 | Kidney | 1.1 ± 0.5 |
| Kidney | 2.28 ± 0.6 | Kidney | 0.5 ± 0.3 | Bone | 3.0 ± 1.3 |
| Muscle | 6.18 ± 1.3 | Muscle | 1.5 ± 0.8 | Tumor | 1.3 ± 0.6 |
| Bone | 2.04 ± 0.7 | Bone | 1.1 ± 0.7 | | |
| Tumor | 2.68 ± 0.5 | | | | |

Finally, s.c. CWR22Rv1 xenografts were avid for [89]Zr-5A10, another AR- and PSA-positive PCa model (FIG. 3c, FIG. 7 and Table 8). Table 8 provides biodistribution data for [89]Zr-5A10 uptake in intact male mice bearing CWR22Rv1 tumors. Ex vivo biodistribution data for [89]Zr-5A10 uptake in intact male mice (n=4) bearing subcutaneous CWR22Rv1 tumors. Data was acquired 24 h post-i.v. administration. Data are expressed as the mean % ID/g±one standard deviation (S.D.). Errors for the ratios are calculated as the geometric mean of the standard deviations.

TABLE 8

| Biodistribution | | Tumor-to-tissue ratio | | Tissue-to-muscle ratio | |
|---|---|---|---|---|---|
| Organ | 24 h (n = 4) | Organ | 24 h (n = 4) | Organ | 24 h (n = 4) |
| Blood | 2.53 ± 0.9 | Blood | 3.4 ± 1.5 | Bladder | 4.6 ± 4.0 |
| Bladder | 2.94 ± 2.1 | Bladder | 2.9 ± 2.2 | Heart | 3.2 ± 1.5 |
| Heart | 2.05 ± 0.1 | Heart | 4.2 ± 1.0 | Lungs | 4.8 ± 2.6 |
| Lungs | 3.06 ± 0.8 | Lungs | 2.8 ± 1.0 | Liver | 41.2 ± 21.2 |
| Liver | 26.11 ± 5.7 | Liver | 0.3 ± 0.1 | Spleen | 50.2 ± 24.1 |
| Spleen | 31.84 ± 3.6 | Spleen | 0.3 ± 0.1 | Stomach | 1.0 ± 0.9 |
| Stomach | 0.64 ± 0.5 | Stomach | 13.3 ± 10.7 | Sm. Intestine | 1.1 ± 0.8 |
| Sm. Intestine | 0.67 ± 0.4 | Sm. Intestine | 12.7 ± 8.4 | Lg. intestine | 1.1 ± 1.1 |

TABLE 8-continued

| Biodistribution | | Tumor-to-tissue ratio | | Tissue-to-muscle ratio | |
|---|---|---|---|---|---|
| Organ | 24 h (n = 4) | Organ | 24 h (n = 4) | Organ | 24 h (n = 4) |
| Lg. intestine | 0.72 ± 0.6 | Lg. intestine | 11.9 ± 11 | Kidney | 22.8 ± 10.8 |
| Kidney | 14.44 ± 1.3 | Kidney | 0.6 ± 0.2 | Bone | 9.5 ± 0.7 |
| Muscle | 0.63 ± 0.3 | Muscle | 13.5 ± 7.1 | Tumor | 13.5 ± 7.1 |
| Bone | 6.01 ± 0.3 | Bone | 1.4 ± 0.4 | | |
| Tumor | 8.59 ± 2.0 | | | | |

Figure 8:
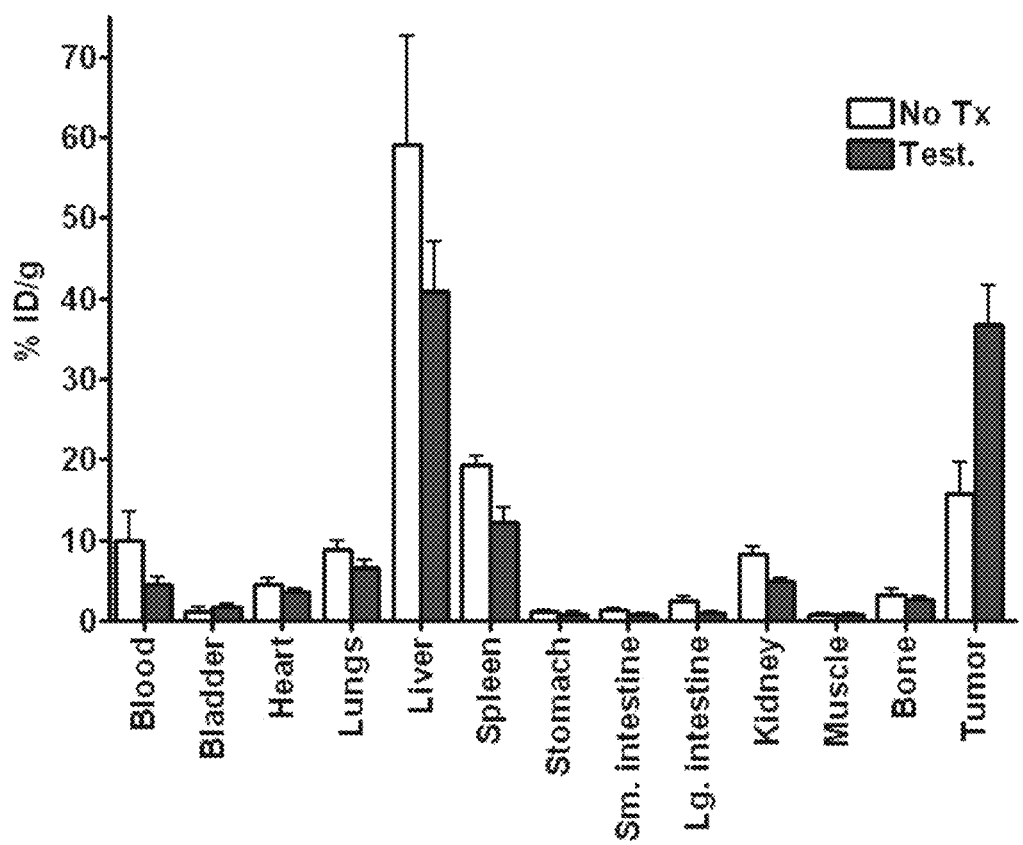
FIG. 8 depicts a biodistribution plot of castrate male mice bearing LNCaP-AR xenografts, with or without a subcutaneous testosterone pellet, injected with $^{89}$Zr-5A10. Six days post surgical implantation of a testosterone pellet or no manipulation (No Tx), tumor-bearing mice were treated with $^{89}$Zr-5A10, and at 24 h post injection, were sacrificed and blood and tissues were harvested for biodistribution studies. Data are reported as mean % ID/g±one standard deviation. *P<0.01 for the intratumoral uptake of $^{89}$Zr-5A10 in the animals exposed to testosterone compared to No Tx.
Figure 9:
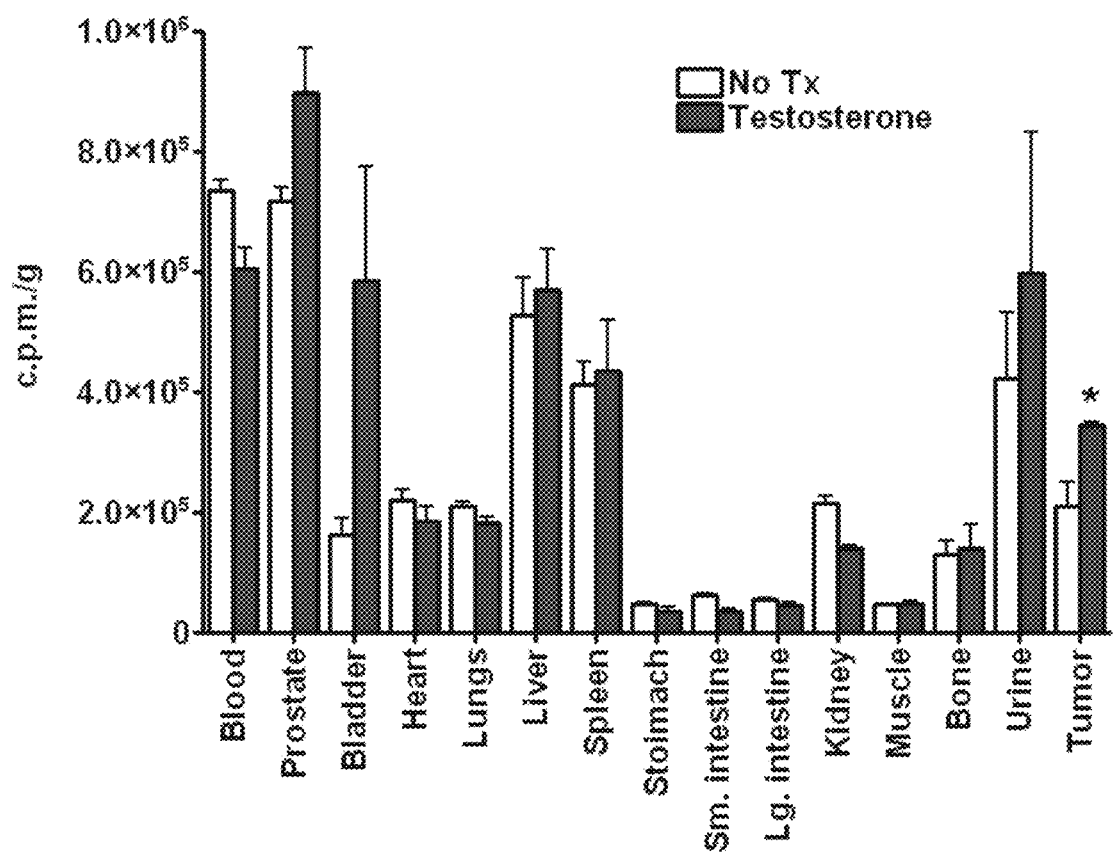
FIG. 9 depicts biodistribution plot of castrated male mice bearing CWR22Rv1 xenografts, with or without a subcutaneous testosterone pellet, injected with $^{89}$Zr-5A10. Six days post surgical implantation of a testosterone pellet or no manipulation (No Tx), tumor-bearing mice were treated with $^{89}$Zr-5A10, and at 24 h post injection, were sacrificed and blood and tissues were harvested for biodistribution studies. Data are reported as mean cpm/g±one standard deviation. *P<0.05 for the intratumoral uptake of $^{89}$Zr-5A10 in the animals exposed to testosterone compared to No Tx.

Example 3: $^{89}$Zr-5A10 Detection of Androgen-Regulated Elevations in fPSA Expression The following example demonstrates that $^{89}$Zr-5A10 can detect androgen-regulated elevations in fPSA expression. Castrate male mice were inoculated with LNCaP-AR, and after tumor formation, animals received no manipulation or a surgically implanted s.c. testosterone pellet. $^{89}$Zr-5A10 was administered 7 d post manipulation, and biodistribution studies were conducted 24 h p.i. $^{89}$Zr-5A10 localization was significantly higher in LNCaP-AR xenografts exposed to testosterone compared to control (FIG. 3d, FIG. 8, and Table 9). FIG. 8 shows a biodistribution plot of castrate male mice bearing LNCaP-AR xenografts, with or without a subcutaneous testosterone pellet, injected with $^{89}$Zr-5A10. Six days post surgical implantation of a testosterone pellet or no manipulation (No Tx), tumor-bearing mice were treated with $^{89}$Zr-5A10, and at 24 h post injection, were sacrificed and blood and tissues were harvested for biodistribution studies. Data are reported as mean % ID/g+ one standard deviation. *P<0.01 for the intratumoral uptake of $^{89}$Zr-5A10 in the animals exposed to testosterone compared to No Tx. As showin in Table 9, $^{89}$Zr-5A10 biodistribution uptake in castrate male mice bearing LNCaP-AR tumor is significantly elevated with androgen treatment. Ex vivo biodistribution data showing the uptake of $^{89}$Zr-5A10 in castrate male mice bearing LNCaP-AR xenografts. Animals (n=4) received no manipulation (No Tx) or a subcutaneous testosterone pellet (Test.). After 7 d, animals were injected with $^{89}$Zr-5A10, and biodistribution data was acquired 24 h post-i.v. administration of the radiotracer. Data are expressed as the mean % ID/g±one standard deviation (S.D.) Errors for the ratios are calculated as the geometric mean of the standard deviations.

tions in castrate male mice bearing LNCaP-AR xenografts, receiving either no manipulation, or a subcutaneous testosterone pellet. Castrate male mice bearing LNCaP-AR xenografts received no treatment (VEH #) or a subcutaneous testosterone pellet (TEST #), and 6 days post manipulation, were injected with $^{89}$Zr-5A10. Twenty four hours post injection, mice were sacrificed for PSA analysis. Tumor tissues were surgically excised. fPSA and tPSA were determined with PSA-directed ELISA (as above), and in the case of intratumoral PSA, the values were normalized to total protein concentration. $^{a}$fPSA concentrations are reported as ng/ml, $^{b}$total PSA concentrations are reported as ng/mL, $^{c}$ total protein concentrations are reported as ng/mg. Abbreviations: fPSA, fPSA; tPSA, total PSA.

TABLE 10

| Mouse | fPSA | tPSA | f/t PSA Ratio | Total Protein | fPSA/ tProtein | tPSA/ tProtein |
|---|---|---|---|---|---|---|
| VEH1 | 91.37 | 139.75 | 0.65 | 8.31 | 10.99 | 16.81 |
| VEH2 | 96.19 | 125.86 | 0.76 | 6.86 | 14.03 | 18.36 |
| VEH3 | 285.18 | 419.60 | 0.68 | 7.68 | 37.15 | 54.66 |
| VEH4 | 159.43 | 198.58 | 0.80 | 8.38 | 19.02 | 23.69 |
| TEST2 | 566.42 | 2765.37 | 0.20 | 8.51 | 66.60 | 325.14 |
| TEST3 | 147.77 | 183.28 | 0.81 | 6.51 | 22.69 | 28.14 |
| TEST4 | 424.31 | 707.52 | 0.60 | 8.23 | 51.56 | 85.98 |
| TEST5 | 384.89 | 551.47 | 0.70 | 5.88 | 65.44 | 93.77 |

Similar results were observed with CWR22Rv1 xenografts (FIG. 8, Table 11, and Table 12). In FIG. 8, six days post surgical implantation of a testosterone pellet or no manipulation (No Tx), tumor-bearing mice were treated with $^{89}$Zr-5A10, and at 24 h post injection, were sacrificed and blood and tissues were harvested for biodistribution studies. Data are reported as mean cpm/g+ one standard deviation.

TABLE 9

| | Biodistribution | | Tumor-to-tissue ratio | | Tissue-to-muscle ratio | |
|---|---|---|---|---|---|---|
| | No Tx | Test. | No Tx | Test. | No Tx | Test. |
| Organ | 24 h (n = 4) | 24 h (n = 4) | 24 h (n = 4) | 24 h (n = 4) | 24 h (n = 4) | 24 h (n = 4) |
| Blood | 9.85 ± 7.36 | 4.57 ± 1.78 | 2.3 ± 1.9 | 7.7 ± 4.2 | | |
| Bladder | 1.22 ± 0.87 | 1.75 ± 0.78 | 18.7 ± 9.6 | 20.2 ± 10.7 | 1.5 ± 1.2 | 2.2 ± 1.3 |
| Heart | 4.41 ± 1.59 | 3.57 ± 1.03 | 5.2 ± 4.1 | 9.9 ± 5.7 | 5.5 ± 2.9 | 4.5 ± 2.2 |
| Lungs | 8.83 ± 2.13 | 6.63 ± 2.07 | 2.6 ± 1.3 | 5.3 ± 2.5 | 11.0 ± 5.1 | 8.3 ± 4.2 |
| Liver | 59.08 ± 27.03 | 40.79 ± 14.15 | 0.4 ± 0.2 | 0.9 ± 0.4 | 73.7 ± 44.3 | 51.3 ± 27.3 |
| Spleen | 19.36 ± 2.12 | 12.19 ± 4.09 | 1.2 ± 0.7 | 2.9 ± 1.5 | 24.2 ± 9.8 | 15.3 ± 8.0 |
| Stomach | 1.14 ± 0.27 | 0.68 ± 0.85 | 20.0 ± 7.6 | 52.2 ± 26.2 | 1.4 ± 0.6 | 0.9 ± 1.1 |
| Sm. Intestine | 1.31 ± 0.44 | 0.83 ± 0.18 | 17.4 ± 7.5 | 42.5 ± 55.6 | 1.6 ± 0.8 | 1.0 ± 0.5 |
| Lg. intestine | 2.49 ± 0.97 | 1.00 ± 0.17 | 9.2 ± 4.6 | 35.5 ± 15.4 | 3.1 ± 1.7 | 1.3 ± 0.5 |
| Kidney | 8.32 ± 1.90 | 4.79 ± 0.96 | 2.7 ± 1.5 | 7.4 ± 3.0 | 10.4 ± 4.7 | 6.0 ± 2.7 |
| Muscle | 0.80 ± 0.31 | 0.79 ± 0.32 | 28.4 ± 12.2 | 44.5 ± 18.8 | | |
| Bone | 3.16 ± 1.42 | 2.65 ± 0.76 | 7.2 ± 3.8 | 13.3 ± 7.3 | 3.9 ± 2.3 | 2.2 ± 1.3 |
| Tumor | 22.75 ± 8.28 | 35.33 ± 13.15 | | | 28.4 ± 15.1 | 44.5 ± 24.4 |

Intratumoral PSA levels also increased, as expected (Table 10). Table 10 provides intratumoral PSA concentra-

*P<0.05 for the intratumoral uptake of $^{89}$Zr-5A10 in the animals exposed to testosterone compared to No Tx. Table 11 provides ex vivo biodistribution data showing the uptake of $^{89}$Zr-5A10 in castrate male mice bearing CWR22Rv1 xenografts. Seven days prior to administration of $^{89}$Zr-5A10, animals (n=4) were unmanipulated (No Tx), or received a subcutaneous testosterone pellet (Test.). Biodistribution data was acquired 24 h post-i.v. administration of the radiotracer. Data are expressed as the mean % ID/g±one standard deviation (S.D.). Errors for the ratios are calculated as the geometric mean of the standard deviations.

Zr5A10 PET using the antiandrogen MDV3100, whose clinical activity is correlated with responses in the LNCaP-AR model.

MDV3100 was dissolved in DMSO so that the final DMSO concentration when administered to animals would be 5%. The formulation of the vehicle is 1% carboxymethyl cellulose, 0.1% Tween-80 and 5% DMSO. MDV3100 or vehicle was administered daily via gavage. Tumor volume (V/mm3) was estimated by external vernier caliper mea-

TABLE 11

| Organ | Biodistribution | | Tumor-to-tissue ratio | | Tissue-to-muscle ratio | |
|---|---|---|---|---|---|---|
| | No Tx 24 h (n = 4) | Test. 24 h (n = 4) | No Tx 24 h (n = 4) | Test. 24 h (n = 4) | No Tx 24 h (n = 4) | Test. 24 h (n = 4) |
| Blood | 7.35 ± 0.35 | 6.04 ± 0.59 | 0.3 ± 0.1 | 0.6 ± 0.1 | 15.4 ± 1.8 | 18.3 ± 3.8 |
| Prostate | 7.18 ± 0.42 | 8.97 ± 1.29 | 0.3 ± 0.1 | 0.4 ± 0.1 | 4.5 ± 1.8 | 7.0 ± 1.0 |
| Bladder | 1.62 ± 0.55 | 5.84 ± 3.3 | 1.3 ± 0.7 | 0.6 ± 0.0 | 3.5 ± 1.2 | 11.9 ± 7.0 |
| Heart | 2.19 ± 0.38 | 1.86 ± 0.42 | 1.0 ± 0.5 | 1.9 ± 1.0 | 4.7 ± 0.9 | 3.8 ± 1.0 |
| Lungs | 2.09 ± 0.16 | 1.83 ± 0.15 | 1.0 ± 0.4 | 1.9 ± 0.4 | 4.5 ± 0.6 | 3.7 ± 0.6 |
| Liver | 5.28 ± 1.21 | 5.70 ± 1.17 | 0.4 ± 0.2 | 0.6 ± 0.1 | 11.3 ± 2.8 | 11.6 ± 2.9 |
| Spleen | 4.12 ± 0.77 | 4.34 ± 1.49 | 0.5 ± 0.2 | 0.8 ± 0.2 | 8.8 ± 1.9 | 8.9 ± 3.3 |
| Stomach | 0.48 ± 0.06 | 0.35 ± 0.11 | 4.4 ± 1.8 | 9.6 ± 3.3 | 1.0 ± 0.2 | 0.7 ± 0.2 |
| Sm. Intestine | 0.63 ± 0.03 | 0.35 ± 0.09 | 3.4 ± 1.3 | 9.8 ± 3.0 | 1.3 ± 0.2 | 0.7 ± 0.2 |
| Lg. intestine | 0.54 ± 0.05 | 0.45 ± 0.09 | 3.9 ± 1.5 | 7.5 ± 2.1 | 1.2 ± 0.2 | 0.9 ± 0.2 |
| Kidney | 2.16 ± 0.23 | 1.40 ± 0.08 | 1.0 ± 0.4 | 2.5 ± 0.5 | 4.6 ± 0.7 | 2.9 ± 0.4 |
| Muscle | 0.46 ± 0.04 | 0.49 ± 0.07 | 4.5 ± 1.8 | 7.0 ± 0.5 | 2.8 ± 1.0 | 2.9 ± 1.5 |
| Bone | 1.31 ± 0.46 | 1.39 ± 0.69 | 1.6 ± 0.6 | 2.5 ± 0.4 | | |
| Tumor | 2.10 ± 0.78 | 3.44 ± 0.09 | | | | |

Table 12 provides tumor analysis of PSA expression levels via ELISA in castrate male mice bearing 22Rv1 tumors, and injected with $^{89}$Zr-5A10. Castrate male mice bearing 22Rv1 xenografts received no treatment (VEH #) or a subcutaneous testosterone pellet (TEST #), and 6 days post manipulation, were injected with $^{89}$Zr-5A10. Twenty four hours post-injection, mice were sacrificed for PSA analysis. Tumor tissues were surgically excised. fPSA and tPSA were determined with PSA-directed ELISA (as above), and the values were normalized to total protein concentration. $^a$ FPSA concentrations are reported as ng/ml, $^b$total PSA concentrations are reported as ng/mL, $^c$total protein concentrations are reported as ng/mg. Abbreviations: fPSA, fPSA; tPSA, total PSA

TABLE 12

| Mouse | fPSA$^a$ | tPSA$^b$ | Total Protein$^c$ | fPSA/ tProtein | tPSA/ tProtein |
|---|---|---|---|---|---|
| VEH 1 | 4.83 | 13.93 | 5.88 | 0.82 | 2.44 |
| VEH 2 | 7.37 | 22.91 | 8.47 | 0.87 | 2.62 |
| VEH 3 | 10.87 | 20.84 | 7.74 | 1.40 | 2.62 |
| VEH 4 | 4.32 | 16.12 | 8.38 | 0.52 | 1.93 |
| VEH 5 | 10.0 | 27.42 | 7.94 | 1.27 | 3.41 |
| TEST 1 | 32.9 | 67.20 | 7.86 | 4.19 | 8.37 |
| TEST 2 | 31.0 | 69.52 | 8.62 | 3.60 | 8.12 |
| TEST 4 | 26.8 | 71.43 | 9.47 | 2.84 | 7.50 |
| TEST 5 | 29.8 | 61.42 | 8.67 | 3.44 | 6.78 |

Collectively, these results showed that $^{89}$Zr-5A10 can faithfully reflect intratumoral AR signaling.

Example 4: In Vivo Quantification of Androgen Receptor Signaling In Vivo with $^{89}$Zr-5A10

The following example demonstrated the capabilities of fPSA-specific monoclonal antibodies to quantitate androgen receptor signaling in vivo. In this particular example, pharmacological inhibition of AR was quantified in vivo with $^{89}$ surements in accordance with previously reported methods (Holland, J. P. et al., Measuring the pharmacokinetic effects of a novel Hsp90 inhibitor on HER2/neu expression in mice using $^{89}$Zr-DFO-trastuzumab. PLoS ONE, 2010, 5 (1), e8859).

Figure 10:
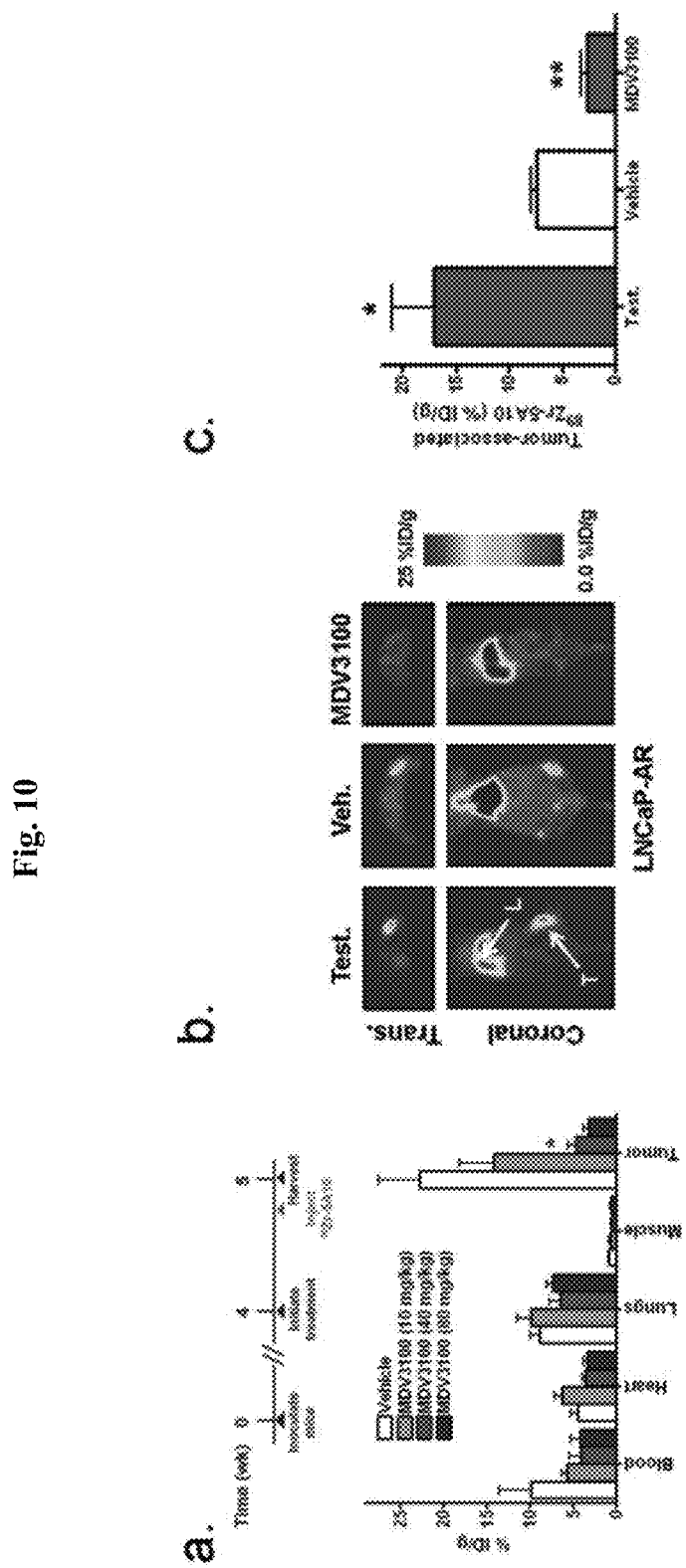
FIG. 10 depicts $^{89}$Zr-5A10 detecting pharmacological inhibition of androgen receptors ("AR") in vivo.
Figure 11:
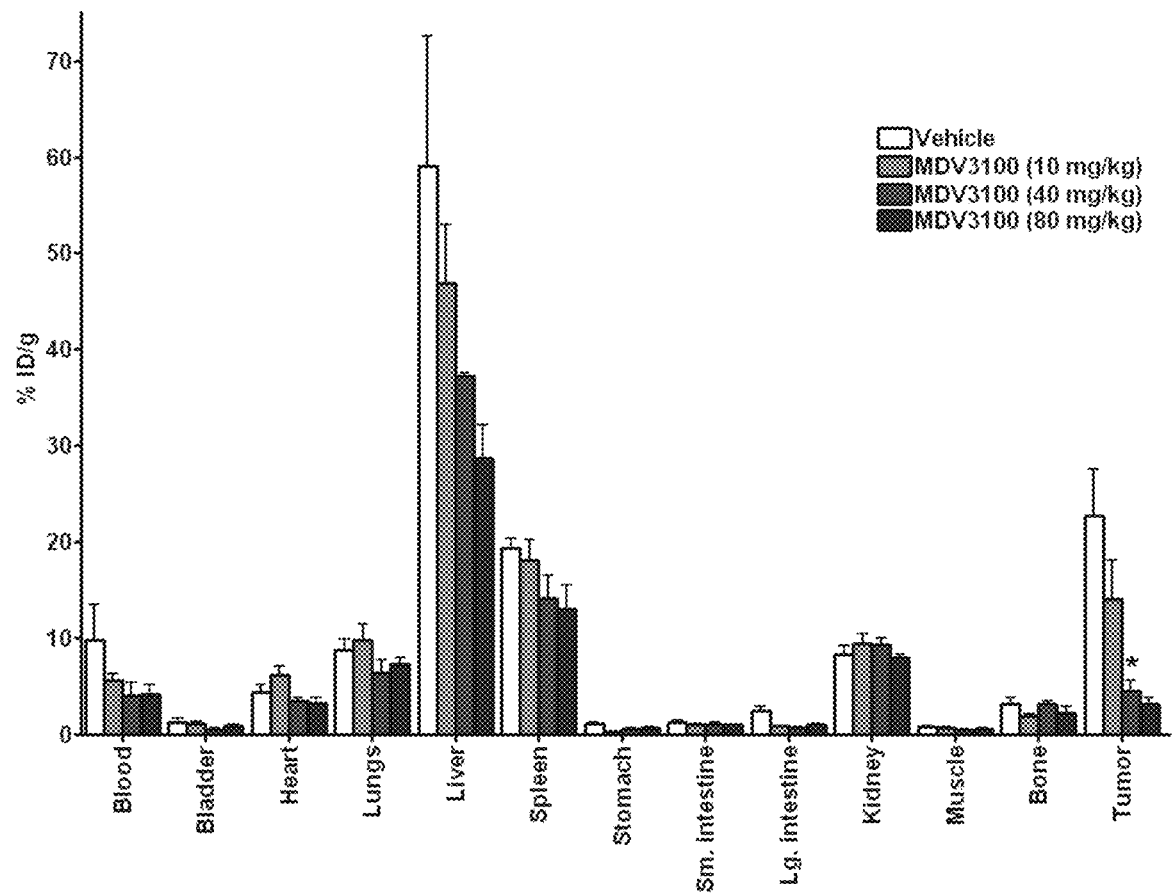
FIG. 11 depicts biodistribution plot of castrate male mice bearing LNCaP-AR xenografts, treated with vehicle or MDV3100, and injected with $^{89}$Zr-5A10. Tumor-bearing castrate mice were treated with vehicle, or the indicated dose of MDV3100 (daily oral gavage). On day 6, mice were injected with $^{89}$Zr-5A10, and 24 h post injection, were sacrificed and blood and tissues were harvested for biodistribution studies. Data are reported as mean % ID/g±one standard deviation. *P<0.01 for MDV3100 40 mg/kg and 80 mg/kg with respect to vehicle. P<0.05 for 40 and 80 mg/kg doses with respect to the 10 mg/kg dose of MDV3100.

Castrate male mice were inoculated with s.c. LNCaPAR xenografts, and tumor-bearing mice were randomized into groups receiving a daily oral gavage of vehicle, or MDV3100 at 10, 40, or 80 mg/kg. Seven days post initiation of treatment, $^{89}$Zr-5A10 was administered, and biodistribution studies were conducted 24 h p.i (FIG. 10a, FIG. 11 and Table 13). In FIG. 10a, biodistribution data from castrate male mice bearing LNCaP-AR xenografts shows that MDV3100 inhibits localization of $^{89}$Zr-5A10 to tumor. Animals were treated with vehicle, or the indicated dose of MDV3100 for 7 d, at which time $^{89}$Zr-5A10 was injected, and animals were harvested for biodistribution studies 24 p.i. *P<0.01 for the 40 mg/kg and 80 mg/kg dose of MDV3100 compared to vehicle or 10 mg/kg MDV3100. FIG. 11, a biodistribution plot of castrate male mice bearing LNCaP-AR xenografts, treated with vehicle or MDV3100, and injected with $^{89}$Zr-5A10, likewise shows that MDV3100 inhibits $^{89}$Zr-5A10 localization to prostate cancer in a dose-dependent manner. Tumor-bearing castrate mice were treated with vehicle, or the indicated dose of MDV3100 (daily oral gavage). On day 6, mice were injected with $^{89}$Zr-5A10, and 24 h post injection, were sacrificed and blood and tissues were harvested for biodistribution studies. Data are reported as mean % ID/g±one standard deviation. *P<0.01 for MDV3100 40 mg/kg and 80 mg/kg with respect to vehicle. P<0.05 for 40 and 80 mg/kg doses with respect to the 10 mg/kg dose of MDV3100. Table 13 shows ex vivo biodistribution data showing the uptake of $^{89}$Zr-5A10 in castrate male mice bearing LNCaP-AR xenografts. Animals (n=4) were treated with vehicle or the indicated dose of MDV3100 (MDV) via daily oral gavage. On day 6, $^{89}$Zr-5A10 was administered i.v. Biodistribution data was acquired 24 h post-i.v. administration of the radiotracer.

TABLE 13

| Tissue | Vehicle 24 h (n = 4) | MDV (10 mg/kg) 24 h (n = 4) | MDV (40 mg/kg) 24 h (n = 4) | MDV (80 mg/kg) 24 h (n = 4) |
|---|---|---|---|---|
| Blood | 9.85 ± 7.36 | 5.70 ± 1.17 | 4.08 ± 2.25 | 4.13 ± 2.49 |
| Bladder | 1.22 ± 0.87 | 1.14 ± 0.53 | 0.50 ± 0.22 | 0.94 ± 0.17 |
| Heart | 4.41 ± 1.59 | 6.21 ± 1.87 | 3.52 ± 0.64 | 3.32 ± 1.14 |
| Lungs | 8.83 ± 2.13 | 9.80 ± 3.28 | 6.37 ± 2.41 | 7.31 ± 1.60 |
| Liver | 59.08 ± 27.03 | 46.95 ± 12.13 | 37.21 ± 0.67 | 28.66 ± 7.94 |
| Spleen | 19.36 ± 2.12 | 18.08 ± 4.45 | 14.18 ± 4.03 | 13.05 ± 5.66 |
| Stomach | 1.14 ± 0.27 | 0.31 ± 0.03 | 0.53 ± 0.33 | 0.69 ± 0.31 |
| Sm. Intestine | 1.31 ± 0.44 | 0.99 ± 0.29 | 0.98 ± 0.41 | 0.99 ± 0.15 |
| Lg. intestine | 2.49 ± 0.97 | 0.89 ± 0.17 | 0.67 ± 0.18 | 0.99 ± 0.39 |
| Kidney | 8.32 ± 1.90 | 9.44 ± 2.17 | 9.32 ± 1.17 | 7.95 ± 0.96 |
| Muscle | 0.80 ± 0.31 | 0.65 ± 0.31 | 0.47 ± 0.29 | 0.58 ± 0.35 |
| Bone | 3.16 ± 1.42 | 1.91 ± 0.42 | 3.13 ± 0.69 | 2.31 ± 1.39 |
| Tumor | 22.75 ± 8.28 | 14.12 ± 8.0 | 4.57 ± 1.78 | 3.19 ± 1.4 |
| Tumor-to-tissue ratio | | | | |
| Blood | 2.3 ± 1.9 | 2.5 ± 1.5 | 1.1 ± 0.8 | 0.8 ± 0.6 |
| Bladder | 18.7 ± 9.6 | 12.4 ± 9.9 | 9.1 ± 5.0 | 3.4 ± 2.1 |
| Heart | 5.2 ± 4.1 | 2.3 ± 1.7 | 1.3 ± 0.8 | 1.0 ± 0.5 |
| Lungs | 2.6 ± 1.3 | 1.4 ± 0.9 | 0.7 ± 0.3 | 0.4 ± 0.2 |
| Liver | 0.4 ± 0.2 | 0.3 ± 0.2 | 0.1 ± 0.1 | 0.1 ± 0.1 |
| Spleen | 1.2 ± 0.7 | 0.8 ± 0.5 | 0.3 ± 0.1 | 0.2 ± 0.1 |
| Stomach | 20.0 ± 7.6 | 45.7 ± 28.2 | 8.6 ± 4.2 | 4.6 ± 2.9 |
| Sm. Intestine | 17.4 ± 7.5 | 14.3 ± 8.2 | 4.7 ± 3.4 | 3.2 ± 2.0 |
| Lg. intestine | 9.2 ± 4.6 | 15.9 ± 10.2 | 6.8 ± 3.9 | 3.2 ± 1.5 |
| Kidney | 2.7 ± 1.5 | 1.5 ± 0.9 | 0.5 ± 0.2 | 0.4 ± 0.2 |
| Muscle | 28.4 ± 12.2 | 21.8 ± 13.4 | 9.7 ± 4.0 | 5.5 ± 2.5 |
| Bone | 7.2 ± 3.8 | 7.4 ± 5.5 | 1.5 ± 1.1 | 1.4 ± 1.0 |
| Tissue-to-muscle ratio | | | | |
| Bladder | 1.5 ± 1.2 | 21.8 ± 16.1 | 9.7 ± 7.0 | 5.5 ± 4.1 |
| Heart | 5.5 ± 2.9 | 1.8 ± 1.2 | 1.1 ± 0.8 | 1.6 ± 1.0 |
| Lungs | 11.0 ± 5.1 | 9.6 ± 5.4 | 7.5 ± 4.8 | 5.7 ± 4.0 |
| Liver | 73.7 ± 44.3 | 15.2 ± 8.8 | 13.6 ± 9.7 | 12.6 ± 8.0 |
| Spleen | 24.2 ± 9.8 | 72.6 ± 39.1 | 79.2 ± 48.3 | 49.4 ± 32.6 |
| Stomach | 1.4 ± 0.6 | 28.0 ± 14.9 | 30.2 ± 20.3 | 22.5 ± 16.6 |
| Sm. Intestine | 1.6 ± 0.8 | 0.5 ± 0.2 | 1.1 ± 1.0 | 1.2 ± 0.9 |
| Lg. intestine | 3.1 ± 1.7 | 1.5 ± 0.9 | 2.1 ± 1.5 | 1.7 ± 1.0 |
| Kidney | 10.4 ± 4.7 | 1.4 ± 0.7 | 1.4 ± 1.0 | 1.7 ± 1.2 |
| Bone | 3.9 ± 2.3 | 14.6 ± 7.7 | 19.8 ± 12.4 | 13.4 ± 8.4 |
| Tumor | 28.4 ± 15.1 | 3.0 ± 1.5 | 6.7 ± 4.3 | 4.0 ± 3.4 |

As expected, each dose of MDV3100 inhibited AR signaling and fPSA synthesis (Table 14). Table 14 provides data regarding tumor analysis of PSA expression levels via ELISA in castrate male mice bearing LNCaP-AR tumors treated with antiandrogens. Castrate male mice bearing LNCaP-AR xenografts received a daily oral gavage of vehicle (VEH #), 10 mg/kg (MDV10 #), 40 mg/kg (MDV 40 #), or 80 mg/kg (MDV80 #). Six days post manipulation, mice were injected with $^{89}$Zr-5A10. Twenty four hours post injection, mice were sacrificed for PSA analysis. Tumor tissues were surgically excised. fPSA and tPSA were determined with PSA-directed ELISA (as above), and in the case of intratumoral PSA, the values were normalized to total protein concentration. [a] fPSA concentrations are reported as ng/ml, [b] total PSA concentrations are reported as ng/mL, [c] total protein concentrations are reported as ng/mg. Abbreviations: fPSA, fPSA; tPSA, total PSA.

TABLE 14

| Mouse | fPSA[a] | tPSA[b] | f/t PSA Ratio | Total Protein[c] | fPSA/ tProtein | tPSA/ tProtein |
|---|---|---|---|---|---|---|
| VEH1 | 91.37 | 139.75 | 0.65 | 8.31 | 10.99 | 16.81 |
| VEH2 | 96.19 | 125.86 | 0.76 | 6.86 | 14.03 | 18.36 |
| VEH3 | 285.18 | 419.60 | 0.68 | 7.68 | 37.15 | 54.66 |
| VEH4 | 159.43 | 198.58 | 0.80 | 8.38 | 19.02 | 23.69 |
| MDV10 1 | 474.40 | 690.48 | 0.69 | 9.20 | 51.57 | 75.06 |
| MDV10 2 | 19.12 | 26.21 | 0.73 | 5.82 | 3.29 | 4.50 |
| MDV10 4 | 48.98 | 86.72 | 0.56 | 6.92 | 7.07 | 12.52 |
| MDV10 5 | 3.96 | 6.64 | 0.60 | 4.50 | 0.88 | 1.48 |
| MDV40 1 | 71.24 | 79.60 | 0.89 | 6.13 | 11.61 | 12.98 |
| MDV40 3 | 43.25 | 51.09 | 0.85 | 7.04 | 6.14 | 7.25 |
| MDV40 4 | 98.26 | 122.15 | 0.80 | 6.50 | 15.13 | 18.81 |
| MDV80 3 | 5.97 | 10.55 | 0.57 | 5.05 | 1.18 | 2.09 |
| MDV80 4 | 77.83 | 112.53 | 0.69 | 7.52 | 10.34 | 14.96 |
| MDV80 5 | 57.31 | 97.80 | 0.59 | 5.74 | 9.99 | 17.05 |

Accordingly, tumor-associated $^{89}$Zr-5A10 was significantly decreased by a 40 and 80 mg/kg dose of MDV3100 (FIG. 10a).

Remarkably, we also observed statistical changes in tumor-associated $^{89}$Zr-5A10 by PET between groups of animals receiving a daily oral gavage of vehicle or 80 mg/kg MDV3100 (FIGS. 10b and 10c, Table 16). FIG. 10b shows representative transverse (Trans.) and coronal PET slices of intact male mice bearing LNCaP-AR xenografts on the right flank, and imaged with $^{89}$Zr-5A10 24 h p.i. after manipulation with an s.c. testosterone pellet, or a daily oral gavage of vehicle or MDV3100 (80 mg/kg) for 7 d. Clear visual differences in tumor-associated $^{89}$Zr5A10 can be seen between the groups. Arrows indicate the position of the tumor (T) and the murine liver (L). In FIG. 10c, region-of-interest analysis of the tumors from the PET study shows statistically significant changes in tumor-associated $^{89}$Zr-5A10. *P<0.01 compared to vehicle. "P<0.05 compared to vehicle. Error bars represent the standard deviation from mean. Table 16 provides a list of the SUV$_{mean}$ values determined from region-of-interest analysis of subcutaneous LNCaP-AR tumors.

TABLE 16

| Vehicle<br>24 h (n = 4) | MDV (80<br>mg/kg)<br>24 h (n = 4) | Testosterone<br>24 h (n = 3) |
|---|---|---|
| 2.54 ± 0.8 | 8.62 ± 1.2 | 19.28 ± 8.0 |
| 2.89 ± 0.6 | 5.25 ± 1.2 | 19.75 ± 7.5 |
| 2.09 ± 0.93 | 7.16 ± 0.8 | 12.07 ± 5.0 |
| 3.23 ± 1.4 | 8.54 ± 1.6 | |

In addition, a significant increase in tumor-associated $^{89}$Zr-5A10 was observed in a separate treatment arm of mice receiving s.c. testosterone pellets.

Collectively, these results highlight the ability of $^{89}$Zr-5A10 to measure pharmacologically triggered changes in intratumoral AR signaling.

Example 5: $^{89}$Zr-5A10 can Distinguish Skeletal Prostate Cancer Lesions

As discussed above, a significant limitation of conventional prostate cancer diagnostics has been an inability to distinguish between true skeletal metastatic disease and nearby bone remodeling, which is either unrelated to metastatic disease or separated in time from treatment to such an extent that analysis is hindered. In the present example, it was demonstrated that fPSA monoclonal antibodies have the ability to distinguish true skeletal prostate cancer lesions.

Osseous tumors were established in intact male mice via injection of LNCaP-AR in the tibia of the left hindlimb as follows. Prior to surgery, castrate male SCID mice were anesthetized with ketamine, and an incision was be made in the left hind limb. The tibia was punctured using a bone drill, and 1×10$^5$ cells (22Rv1 or LNCaP-AR) injected into the marrow. The puncture was closed with bone wax, the incision sutured, and animals received a palliative dose of carprofen (5 mg/kg) once daily for three days post surgery. Tumor development was followed with bioluminescence imaging, and confirmed with MRI. The bone fracture model was prepared similar to the osseous tumor model, excluding injection of cells and application of bone wax.

Figure 12:
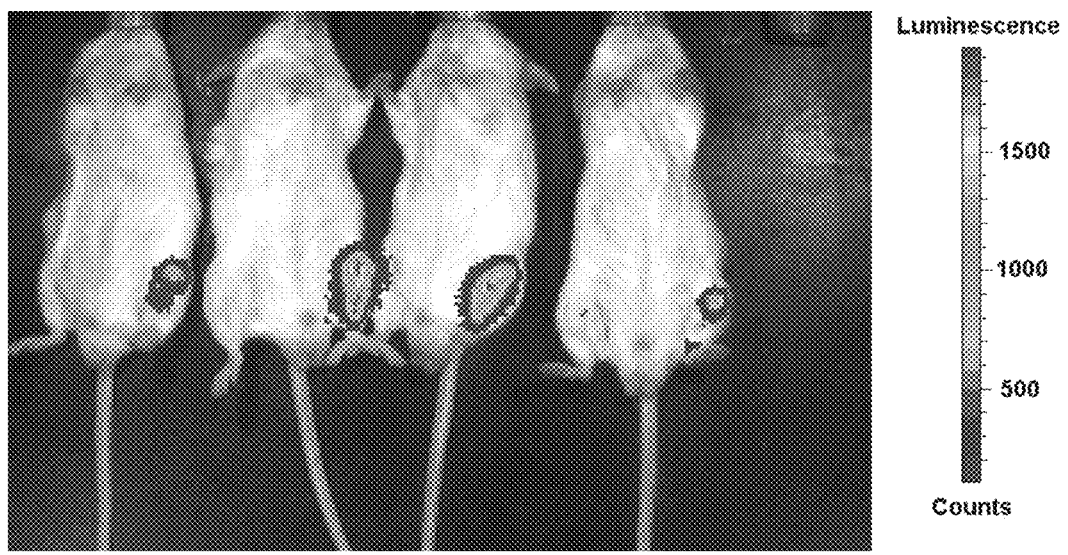
FIG. 12 depicts representative bioluminescence images of mice inoculated with LNCaP-AR in the left tibia. Intact male mice were inoculated with LNCaP-AR in the tibia, progression was monitored by bioluminescence, and tumor development was confirmed by MRI and serum PSA analysis (see text). A typical image of a cohort of tumor bearing mice at 5 weeks post inoculation is shown. These animals had confirmed disease.
Figure 13:
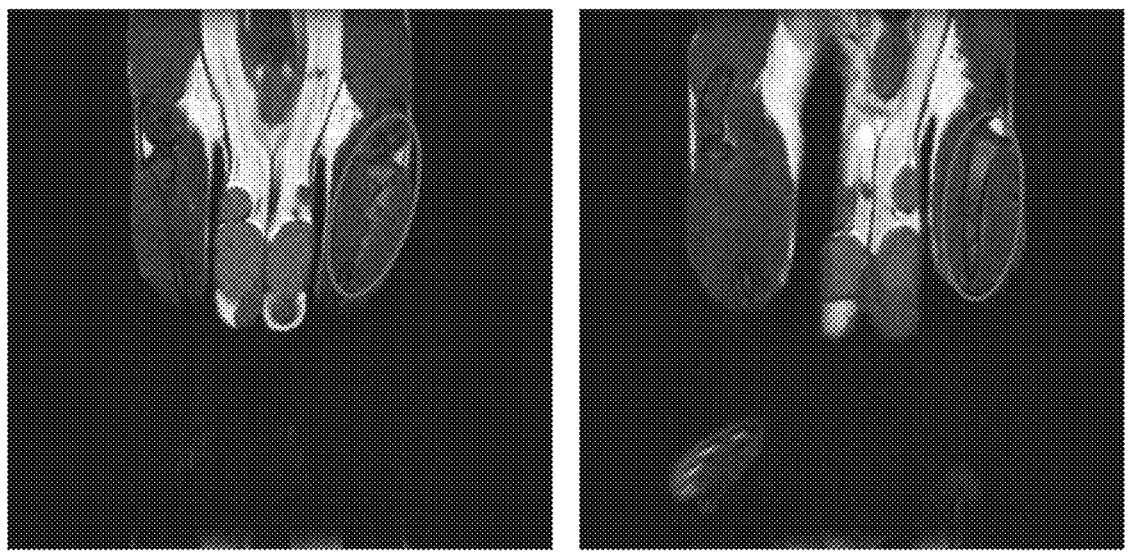
FIG. 13 depicts representative MRI slices showing tumor involvement of bone. Intact male mice were inoculated with LNCaP-AR in the tibia, and tumor development was confirmed visually with MRI and serum PSA analysis. Regions of contrast in the left hindlimb (oriented on the right side of the MRI slice) indicating a tumor mass are circumscribed in red.

Tumor development was confirmed by MRI after 7 weeks (FIG. 12 and FIG. 13). FIG. 12 shows representative bioluminescence images of mice inoculated with LNCaP-AR in the left tibia. Intact male mice were inoculated with LNCaP-AR in the tibia, progression was monitored by bioluminescence, and tumor development was confirmed by MRI and serum PSA analysis. A typical image of a cohort of tumor bearing mice at 5 weeks post inoculation is shown. These animals had confirmed disease and positive bioluminescence.

Mouse magnetic resonance images were acquired on a Bruker 4.7T Biospec scanner operating at 200 MHz and equipped with a 400 mT/m ID 12 cm gradient coil (Bruker Biospin MRI GmbH, Ettlingen, Germany). A custom-built quadrature birdcage resonator with ID of 32 mm was used for RF excitation and acquisition (Stark Contrast MRI Coils Research Inc., Erlangen, Germany). Mice were anaesthetized with oxygen and 1% isoflurane gas. Animal breathing was monitored by using a small animal physiological monitoring system (SA Instruments, Inc., Stony Brook, N.Y.). T2 weighted scout images along three orthogonal orientations were first acquired for animal positioning. The T2-weighted fast spin-echo RARE sequence (Rapid Acquisition with Relaxation Enhancement) was used to acquire axial mouse pelvic images with a slice thickness of 0.8 mm, FOV 30 mm×34 mm with a spatial resolution of 117×133 m. The following acquisition parameters, TR=4.5 s, TE=40 ms, RARE factor 8, and an acquisition time of 20 minutes were used.

FIG. 13 presents representative MRI slices showing tumor involvement of bone. Intact male mice were inoculated with LNCaP-AR in the tibia, and tumor development was confirmed visually with MRI and serum PSA analysis. Regions of contrast in the left hindlimb (oriented on the right side of the MRI slice) indicating a tumor mass are circumscribed in red.

Figure 14:
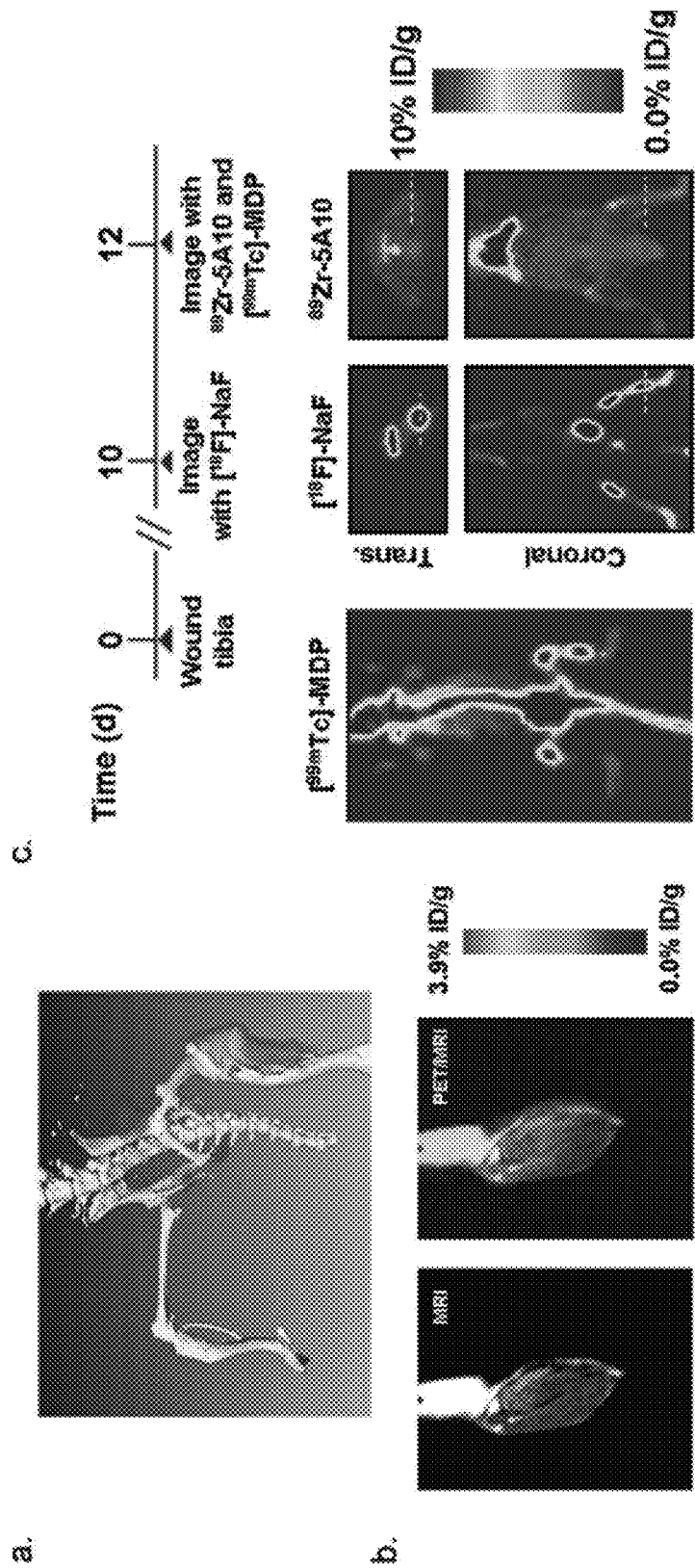
FIG. 14 depicts $^{89}$Zr-5A10 specifically targeting prostate cancer in the bone microenvironment in vivo.

PET/CT studies showed high contrast in the tumor-bearing hindlimb, compared to the contralateral limb (FIG. 14a). For PET/CT studies, computed tomography (CT) images were acquired on a small-animal Siemens/CTI microCAT II (Siemens Medical Solutions, Malvern, Pa.) scanner with an 8.5 cm axial by 5.0 cm transaxial FOV. Co-registered PET/CT images were recorded and mapped to a matrix in accordance with previously reported methods. In FIG. 14a, a co-registered three dimensional, volume rendered PET/CT image shows that $^{89}$Zr5A10 localizes to an osseous LNCaP-AR graft located in the left tibia of an intact male mouse. The PET data, rendered in a blue-green color scale, shows a greater amount of activity on the animal's left (tumor-bearing) tibia compared to the right (normal) tibia.

Figure 15:
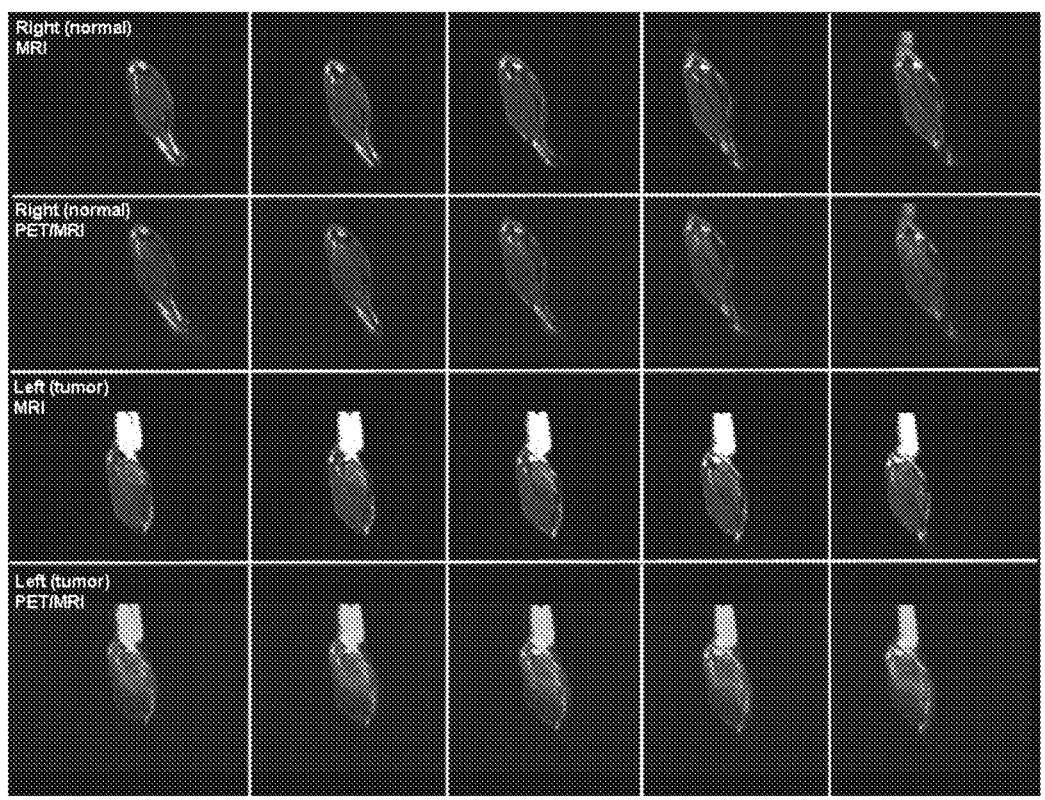
FIG. 15 depicts co-registered PET/MRI slices showing co-alignment of $^{89}$Zr-5A10 with tumor in the tibia. Intact male mice were inoculated with LNCaP-AR in the tibia, and tumor development was confirmed visually with MRI and serum PSA analysis. A co-registered PET/MRI image was acquired 24 h post injection of $^{89}$Zr-5A10. The images from the right (normal) hindlimb are presented for comparison.

Consistent with this observation, co-registered PET/MRI images showed an alignment of the PET and MRI contrast in the tibia (FIG. 14b and FIG. 15). In FIG. 14b, a co-registered PET/MRI image shows the co-localization of positron emissions from $^{89}$Zr-5A10 with the tumor-associated contrast detected by MRI. FIG. 15 show co-registered PET/MRI slices showing co-alignment of $^{89}$Zr-5A10 with tumor in the tibia. Intact male mice were inoculated with LNCaP-AR in the tibia, and tumor development was confirmed visually with MRI and serum PSA analysis. A co-registered PET/MRI image was acquired 24 h post injection of $^{89}$Zr-5A10. The images from the right (normal) hindlimb are presented for comparison.

Figure 16:
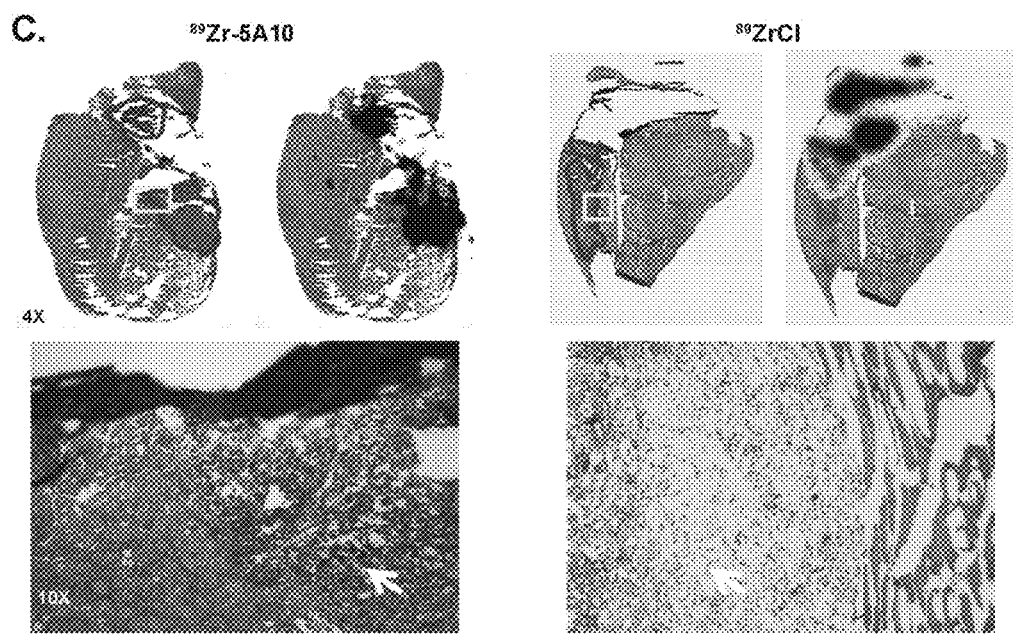
FIG. 16 depicts histology and overlaid autoradiography of mice bearing an osseous LNCaP-AR graft treated with $^{89}$Zr-5A10 (left) and $^{89}$ZrCl (right), and shows that $^{89}$Zr-5A10 localizes to tumor tissue, while $^{89}$ZrCl localizes to normal bone. Tumor tissue was distinguished by visual inspection of histology (defined by H&E staining), and is circumscribed in blue at 4×, and highlighted with an arrow at 10×. The region of tissue selected for a higher magnification view is outlined in yellow.

Post-mortem autoradiography of a surgically excised tibia showed that positron emissions from $^{89}$Zr-5A1 0 co-aligned with the topography of the LNCaP-AR lesion, defined by histology (FIG. 16). Procedures were conducted as follows: After mice were sacrificed, the tibia, including the tumor, was surgically excised and embedded in OCT (Miles Inc., Elkhart, Ind.) and snap frozen on dry ice in a cryo-mold. Sets of ten contiguous 5 μm thick tissue sections were cut using a Microm HM500 cryostat microtome (Microm International, Walldorf, Germany) and arrayed onto poly-L-lysine coated glass microscope slides. Tissue sections were fixed in 10% phosphate-buffered formalin for 5 min, washed twice, air dried and stained with hematoxylin and eosin (H&E). Stained tissue sections were placed in a film cassette against a Fuji film BAS-MS2325 imaging plate (Fuji Photo Film Co, Tokyo, Japan) to acquire digital autoradiograms (DAR). The slides were exposed for 48 h, ~168 h after injection of $^{89}$ZrCl or $^{89}$Zr-5A10. Exposed phosphor plates were read by a Fujifilm BAS-180011 bio-imaging analyzer (Fuji Photo Film Co, Tokyo, Japan) generating digital images with 50 μm pixel dimensions. Digital images were obtained with an Olympus BX60 System Microscope (Olympus America Inc, Melville, N.Y.) equipped with a motorized stage (Prior Scientific Inc, Rockland, Mass.). Subsequently, H&E images were acquired to the same resolution as the DAR data. DAR images were manually aligned to the H&E images using rigid planar transforms.

In FIG. 16, histology and overlaid autoradiography of mice bearing an osseous LNCaP-AR graft treated with $^{89}$Zr-5A10 (left) and $^{89}$ZrCl (right) shows that $^{89}$Zr-5A10 localizes to tumor tissue, while $^{89}$ZrCl localizes to normal bone. Tumor tissue was distinguished by visual inspection of histology (defined by H&E staining), and is circumscribed in blue at 4×, and highlighted with an arrow at 10×. The region of tissue selected for a higher magnification view is outlined in yellow.

To further confirm that $^{89}$Zr-5A1 0 does not cross-react with bone remodeling, bone fractures were induced surgically in a separate cohort of mice by puncturing the tibia in the right hindlimb. Both 18FNaF and 99mTc-MDP readily localized to the site of repair, while $^{89}$Zr-5A1 0 did not (FIG. 14c). In FIG. 14c, intact male mice received a fracture in the tibia, and ten days post surgery, bone remodeling was evaluated with $^{18}$F-NaF. A clear region of contrast was identified in the fractured tibia by PET. Two days after the first image, animals received a coinjection of 99mTc-MDP and $^{89}$Zr-5A10. SPECT imaging showed that 99mTc-MDP also localized to the region of healing bone, as expected. In contrast, PET imaging showed no detectable $^{89}$Zr5A10 at the wound site, pointing to the high specificity of this reagent for PCa compared to contemporary clinical radiotracers.

Collectively, these results highlighted the unique specificity of $^{89}$Zr-5A1 0 for prostate cancer-derived tumors in the bone.

Example 6: Summary and Comparative Data

It has been Demonstrated that Changes in the Expression of PSA, an Androgen receptor-regulated, prostate-specific gene product, can be measured non-invasively with the novel radiotracers linked to monoclonal antibodies specific for fPSA. In support of suitability for quantifying androgen receptor signaling, $^{89}$Zr-5A10 readily localized to multiple androgen receptor- and PSA-positive prostate cancers models, and quantitatively measured declines in fPSA synthesis induced by antiandrogen therapy in a clinically validated xenograft model of prostate cancer. Since $^{89}$Zr5A10 specifically targets prostate cancers cells rather than the non-malignant skeletal pathologies that phenocopy the changes induced by cancers on bone scans, radiotracers of the invention offer the opportunity for more accurate staging and better treatment selection. In this regard, embodiments of the invention provide an unprecedented opportunity to study individual lesions in a heterogeneous disease to improve our understanding of tumor biology.

Figure 17:
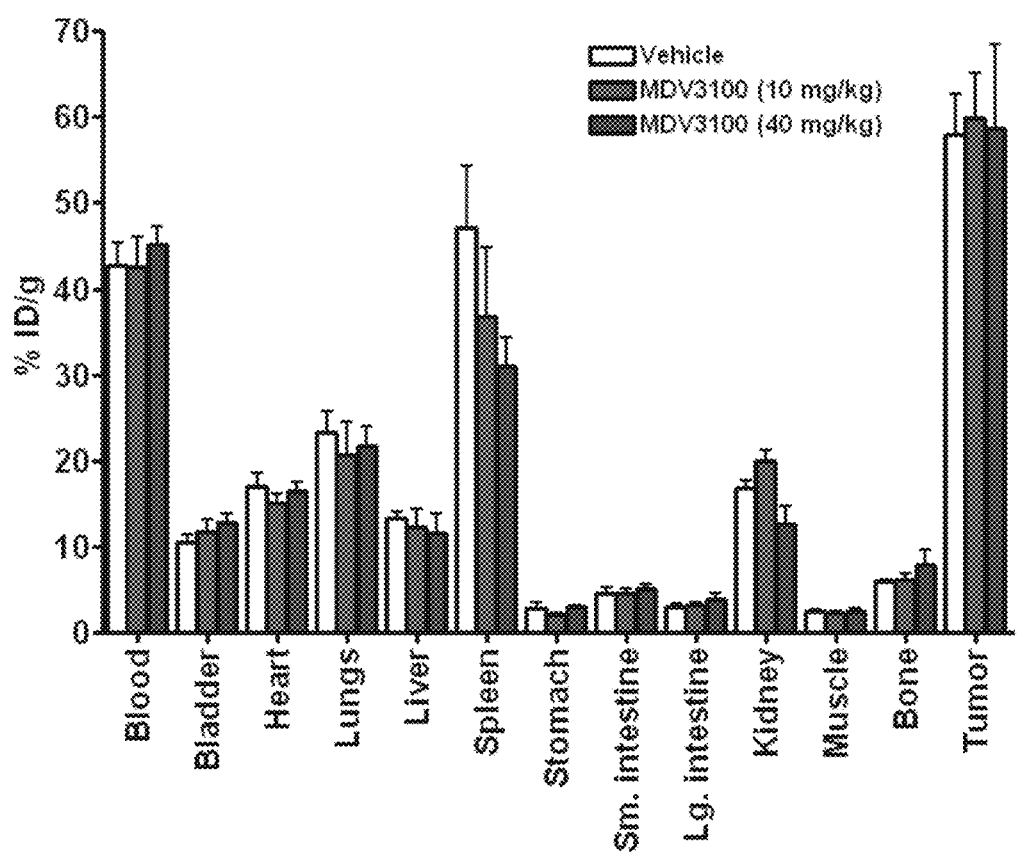
FIG. 17 depicts a biodistribution plot of castrate male mice bearing LNCaP-AR xenografts, treated with vehicle or MDV3100, and injected with $^{89}$Zr-J591. Tumor-bearing castrate mice were treated with vehicle, or the indicated dose of MDV3100 (daily oral gavage). On day 6, mice were injected with $^{89}$Zr-J591, and 24 h post injection, were sacrificed and blood and tissues were harvested for biodistribution studies. Data are reported as mean % ID/g±one standard deviation.

It has previously reported that changes in prostate-specific membrane antigen (PSMA), a cell surface protein whose expression is suppressed by androgen receptor signaling, can also serve as a noninvasive marker for imaging of androgen receptor signaling. However, PSMA expression is not prostate-specific, and the clinical impact of androgen receptor-directed therapy on PSMA expression is not known. Also, a formal comparison in LNCaP-AR xenografts showed that $^{89}$Zr-5A10 PET resulted in a more compelling change in tumor localization post-therapy than identically labeled monoclonal antibodies against PSMA ($^{89}$Zr-J591) (FIG. 17). FIG. 17 is a biodistribution plot of castrate male mice bearing LNCaP-AR xenografts, treated with vehicle or MDV3100, and injected with $^{89}$Zr-J591. Tumor-bearing castrate mice were treated with vehicle, or the indicated dose of MDV3100 (daily oral gavage). On day 6, mice were injected with $^{89}$Zr-J591, and 24 h post injection, were sacrificed and blood and tissues were harvested for biodistribution studies. Data are reported as mean % ID/g±one standard deviation. As can be clearly seen in FIG. 17, monoclonal antibodies against PMSA fail to demonstrate any statistically significant difference in tumor localization post-therapy, thereby demonstrating the superior and unexpected results of embodiments of the present invention.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description. Likewise, those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims.

In the claims articles such as "a", "an" and "the" may mean one or more than one unless indicated to the contrary or otherwise evident from the context. Thus, for example, reference to "an antibody" includes a plurality of such antibodies, and reference to "the cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are presenting, employed in, or otherwise relevant to a given product or process. Furthermore, it is to be understood that the invention encompasses all variations, combinations, and permutations in which one or more limitation, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for anyone of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understand of one of ordinary skill in the art, values that are expressed as ranges can assume any specific value or sub-range within the state ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

What is claimed is:

1. A method of monitoring response to a prostate cancer treatment to a subject with a prostate tumor, the method comprising:
   administering radiolabeled 5A10 antibody to a subject who has received the prostate cancer treatment; and
   imaging the administered radiolabeled 5A10 antibody in situ in the subject so that a first post-treatment level of fPSA in the prostate tumor or tissue of the subject is determined; and comparing the first post-treatment level of fPSA in the tumor or tissue with a pre-treatment level of fPSA in the tumor or tissue of the subject, wherein a decrease in the first post-treatment level of fPSA when compared to the pre-treatment level of fPSA is indicative that the treatment is effective.

2. The method of claim 1, wherein the method further comprises:
   repeating the steps of administering and imaging so that at least a second post-treatment level of fPSA in the prostate tumor or tissue of the subject is determined;
   continuing the prostate cancer treatment if the at least one second post-treatment level is the same or lower than the first post-treatment level, and discontinuing or changing treatment if the at least one second post-treatment level is higher than the first post-treatment level.

---

SEQUENCE LISTING

```
<160> NUMBER OF SEQ ID NOS: 4

<210> SEQ ID NO 1
<211> LENGTH: 15
<212> TYPE: DNA
<213> ORGANISM: Homo sapiens

<400> SEQUENCE: 1
agcacttgct gttct                                                      15

<210> SEQ ID NO 2
<211> LENGTH: 7
<212> TYPE: PRT
<213> ORGANISM: Homo sapiens

<400> SEQUENCE: 2

Ser Trp Gly Ser Glu Pro Cys
1               5

<210> SEQ ID NO 3
<211> LENGTH: 4
<212> TYPE: PRT
<213> ORGANISM: Homo sapiens

<400> SEQUENCE: 3

Ser Trp Gly Ser
1

<210> SEQ ID NO 4
<211> LENGTH: 5
<212> TYPE: PRT
<213> ORGANISM: Homo sapiens

<400> SEQUENCE: 4

His Pro Gln Lys Val
1               5
```

3. The method of claim 1, wherein the prostate cancer treatment is selected from the group consisting of photosensitizers, nucleic acids, radiosensitizers, radioisotopes, superantigens, prodrugs, prodrug-activating enzymes, anti-angiogenic agents and anti-androgen therapies.

4. The method of claim 1, wherein the prostate cancer treatment is anti-androgen therapy.

5. The method of claim 1, wherein the prostate cancer treatment is selected from the group consisting of MDV3100, ARN-509 and doxorubicin.

6. The method of claim 1, wherein the prostate cancer treatment is selected from a group consisting of castration, RU58642, LG120907, LG105, RD162, MDV3100, BMS-641988, CH5137291, ataric acid, N-butylbenzenesulfonamide, cyproterone acetate, hydroxyflutamide, bicalutamide, nilutamide, TAK700, ARN-509, cabozantimib, ipilimumab, custirsen, BPX-101, alpharadin, denosumab and Protsvac-VF.

7. The method of claim 1, wherein the radiolabeled 5A10 antibody comprises a radiolabel selected from the group consisting of zirconium-89 ($^{89}$Zr), iodine-124 ($^{124}$I), iodine-131 ($^{131}$I), iodine-125 ($^{125}$I), bismuth-212 ($^{212}$Bi), bismuth-213 ($^{213}$Bi), astatine-221 ($^{211}$At), (copper-67 ($^{67}$Cu), copper-64 ($^{64}$Cu), rhenium-186($^{186}$Re), rhenium-186 ($^{188}$Re), phosphorus-32 ($^{32}$P), samarium-153 ($^{153}$Sm), lutetium-177 ($^{117}$Lu), technetium-99m ($^{99m}$Tc), gallium-67 ($^{67}$Ga), indium-I11($^{111}$In) and thallium-201 ($^{201}$Tl).

8. The method of claim 1, wherein the imaging step comprises detection by Single Photon Emission Computed Tomography (SPECT), Position Emission Tomography (PET), or Magnetic Resonance Imaging (MRI).

* * * * *